US011730804B1

(12) United States Patent
Wang et al.

(10) Patent No.: US 11,730,804 B1
(45) Date of Patent: Aug. 22, 2023

(54) COMPOSITIONS AND METHODS FOR THE PREVENTION AND TREATMENT OF RABIES VIRUS INFECTION

(71) Applicant: Replicate Bioscience, Inc., San Diego, CA (US)

(72) Inventors: Nathaniel Stephen Wang, San Diego, CA (US); Shigeki Joseph Miyake-Stoner, San Diego, CA (US); Parinaz Aliahmad, San Diego, CA (US); Andrew Geall, San Diego, CA (US)

(73) Assignee: Replicate Bioscience, Inc., San Diego, CA (US)

( * ) Notice: Subject to any disclaimer, the term of this patent is extended or adjusted under 35 U.S.C. 154(b) by 0 days.

(21) Appl. No.: 17/720,002

(22) Filed: Apr. 13, 2022

(51) Int. Cl.

| | |
|---|---|
| ***C12N 15/86*** | (2006.01) |
| ***C07K 7/00*** | (2006.01) |
| ***A61K 39/12*** | (2006.01) |
| ***C12N 7/00*** | (2006.01) |
| *A61K 39/00* | (2006.01) |

(52) U.S. Cl.
CPC ................ *A61K 39/12* (2013.01); *C12N 7/00* (2013.01); *C12N 15/86* (2013.01); *A61K 2039/5256* (2013.01); *A61K 2039/5258* (2013.01); *C12N 2770/36122* (2013.01); *C12N 2770/36134* (2013.01); *C12N 2770/36143* (2013.01); *C12N 2770/36145* (2013.01); *C12N 2770/36162* (2013.01)

(58) Field of Classification Search
None
See application file for complete search history.

(56) References Cited

U.S. PATENT DOCUMENTS 9,441,247 B2 * 9/2016 Rayner .................. C12N 15/86

FOREIGN PATENT DOCUMENTS

CN 11064632 A * 1/2020
EP WO 2019/086645 A1 * 5/2019

OTHER PUBLICATIONS

Lou et al., Journal of Controlled Release, 2020, 325:370-379. (Year: 2020).*

Geall et al., PNAS, Sep. 4, 2012, 109(36):14604-14609 plus supporting information, pp. 1-6. (Year: 2012).*

Giesen et al., Expert Review of Vaccines, 2015, 14(3):351-367. (Year: 2015).*

Perri et al., Journal of Virology, Oct. 2003, 77(19):10394-10403. (Year: 2003).*

Paessler et al., Journal of Virology, Sep. 2003, 77(17):9278-9286. (Year: 2003).*

English Translation of CN 110643632 A to Zhang et al, Clarivate Analytics, 2022, 14 pages. (Year: 2022).*

Benmansour, A. et al. (Aug. 1991). "Antigenicity of Rabies Virus Glycoprotein," *J. Virol.* 65(8):4198-4203.

Bunschoten, H. et al. (Feb. 1989). "Characterization of a new virus-neutralizing epitope that denotes a sequential determinant on the rabies virus glycoprotein," *J. Gen. Virol.* 70(Pt. 2):291-298.

Coulon, P. et al. (Jan. 1998). "An avirulent mutant of rabies virus is unable to infect motoneurons in vivo and in vitro," *J. Virol.* 72(1):273-278.

Dietzschold, B. et al. (Jan. 1983). "Characterization of an antigenic determinant of the glycoprotein that correlates with pathogenicity of rabies virus," *Proc. Natl. Acad. Sci. USA* 80(1):70-74.

Luo, T.R. et al. (Sep. 1997). "A virus-neutralizing epitope on the glycoprotein of rabies virus that contains Trp251 is a linear epitope," *Virus Res.* 51(1):35-41.

Ni, Y. et al. (1995). "Mapping and characterization of a sequential epitope on the rabies virus glycoprotein which is recognized by a neutralizing monoclonal antibody, RG719," *Microbiol. Immunol.* 39(9):693-702.

Prosniak, M. et al. (Jul. 1, 2003). "Development of a cocktail of recombinant-expressed human rabies virus-neutralizing monoclonal antibodies for postexposure prophylaxis of rabies," *J. Infect. Dis.* 188(1):53-56.

Seif, I. et al. (Mar. 1985). "Rabies virulence: effect on pathogenicity and sequence characterization of rabies virus mutations affecting antigenic site III of the glycoprotein," *J. Virol.* 53(3):926-934.

* cited by examiner

*Primary Examiner* — Stacy B Chen
(74) *Attorney, Agent, or Firm* — Mintz, Levin, Cohn, Ferris, Glovsky and Popeo, P.C.

(57) ABSTRACT

The present disclosure relates generally to the field of molecular virology, and particularly relates to nucleic acid molecules encoding a modified alphavirus virus viral genome or self-replicating RNA (srRNA) construct, recombinant cells and pharmaceutical compositions containing the same, as well as the use of such nucleic acid molecules, recombinant cells and compositions for production of desired products in cell cultures or in a living body. Also provided are methods for eliciting an immune response in a subject in need thereof, as well as methods for preventing and/or treating rabies virus infection.

26 Claims, 4 Drawing Sheets

Specification includes a Sequence Listing.

COMPOSITIONS AND METHODS FOR THE PREVENTION AND TREATMENT OF RABIES VIRUS INFECTION

INCORPORATION BY REFERENCE OF SEQUENCE LISTING

The instant application contains a Sequence Listing which has been submitted electronically in ASCII format and is hereby incorporated by reference in its entirety. Said ASCII copy, created on Mar. 31, 2022, is named 058462_510F01US_SequenceListing.txt and is 82,022 bytes in size.

FIELD

The present disclosure relates to the field of molecular virology and immunology, and particularly relates to nucleic acid molecules encoding modified alphavirus viral genomes or self-replicating RNA (srRNA), recombinant cells, and pharmaceutical compositions containing the same, as well as the use of such nucleic acid molecules, recombinant cells, and compositions for production of desired products in cell cultures or in a living body. Also provided are methods for eliciting an immune response in a subject in need thereof, as well as methods for preventing and/or treating rabies virus infection.

BACKGROUND

Rabies is a viral zoonosis, endemic in more than 100 countries and territories, and poses a threat to more than 3 billion people. The disease is invariably fatal following the onset of clinical symptoms occurring in the absence of postexposure prophylaxis (WHO epidemiological record 2010. No. 32 (85):309-320. Rabies vaccine: WHO position paper). The WHO assumes 55000 rabies related deaths and the postexposure treatment (PET) of more than 10 million people each year.

Currently available rabies vaccines include the most widely used but highly risk-prone nerve tissue vaccines, or the safer but more costly cell culture and embryonated egg vaccines (CCEEVs). Risks associated with nerve tissue vaccines include induction of autoimmune central nervous system disease due to their inherent myelin content; the need for multiple injections; and unreliable efficacy. The WHO does not recommend the use of nerve tissue vaccines and strongly encourages the increased supply of modern and high-quality vaccines to poor populations. Avian embryo vaccines and cell culture vaccines contain inactivated purified virus, free from nerve protein. Although safer and more immunogenic than nerve tissue vaccines, cell culture production methods are time-consuming and resource-intensive and the associated cost burden largely restricts the use to the developed world despite of WHO current recommendations.

Pre-exposure prophylaxis (PrEP) with cell culture vaccine is safe and is recommended for individuals at increased risk (e.g., laboratory staff, veterinarians, animal handlers, wildlife workers and travelers to rabies-endemic areas), but it is largely restricted for reasons of cost to the developed world. Furthermore, the anti-rabies vaccine is recommended for people travelling to countries in Africa and Asia, where rabies is endemic.

A current problem is a shortage of these vaccines, which are, at certain times, only available for postexposure prophylaxis and not for prophylactic vaccination. Prophylactic vaccination is, however, important for travelers visiting developing countries where rabies virus Ig for postexposure prophylaxis may not be available.

Therefore there is a need for a safe and effective rabies vaccine which can be delivered at any time.

The disclosure provided here provides solutions to the problems existing with previous attempts to generate rabies vaccines and potentially offers improved methods for rabies infection treatment and prevention.

SUMMARY

The present disclosure relates generally to the development of immuno-therapeutics, such as recombinant nucleic acid constructs and pharmaceutical compositions including the same for use in the prevention and management of rabies virus infection. In particular, as described in greater detail below, some embodiments of the disclosure provide nucleic acid constructs containing sequences that encode a modified alphavirus genome or self-replicating RNA (srRNA) where at least a portion of the nucleic acid sequence encoding the viral structural proteins of the modified alphavirus genome or srRNA has been replaced by a coding sequence for a polypeptide construct comprising an envelope glycoprotein G of a rabies virus (RABV-G), a variant thereof, or an antigenic determinant of either thereof. Also disclosed are recombinant cells that have been engineered to include one or more of the nucleic acid constructs disclosed herein, methods for producing a molecule of interest, and pharmaceutical compositions including one or more of the following: (a) a nucleic acid construct of the disclosure, (b) a recombinant cell of the disclosure, or (c) a pharmaceutical composition of the disclosure. Further provided in particular aspects of the disclosure are compositions and methods for eliciting an immune response in a subject in need thereof, and/or for the prevention and/or treatment of rabies virus infection. The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

In one aspect of the disclosure, provided herein are nucleic acid constructs including a nucleic acid sequence encoding a modified alphavirus genome or self-replicating RNA (srRNA), wherein at least a portion of the nucleic acid sequence encoding the viral structural proteins of the modified alphavirus genome or srRNA has been replaced by a coding sequence for a polypeptide construct comprising an envelope glycoprotein G of a rabies virus (RABV-G), a variant thereof, or an antigenic determinant of either thereof.

In some embodiments, the antigenic determinant resides within the N-terminal half of the RABV-G.

In some embodiments, the antigenic determinant resides within the C-terminal half of the RABV-G.

In some embodiments, the antigenic determinant comprises antigenic site I, antigenic site II, antigenic site III, antigenic site IV, antigenic site minor A of the RABV-G, or a combination of any thereof.

In some embodiments, the envelope glycoprotein G is of a virulent rabies virus strain or an avirulent rabies virus strain.

In some embodiments, the envelope glycoprotein G is of a rabies virus strain selected from a Flury LEP strain, a Flury LEP-C strain, a Flury HEP strain, a 1088 strain, a AT6 strain, a CQ92 strain, a CVS-11 strain, a CVS-26 strain, a CVS-26(G-N204S) strain, a CYN1009D strain, a CYN1026D strain, a CYN1029D strain, a CYN1138D strain, a CYN1140D strain, a CYN1141D strain, a CYN1242H strain, a CYN1243D strain, a CYN1244D strain, a CYN1245D strain, a CYN1247D strain, a CYN1249D strain, a CYN1250D strain, a CYN1251D strain, a CYN1252D strain, a CYN1253D strain, a CYN1255D strain, a CYN1256D strain, a CYN1257D strain, a CYN1259D strain, a CYN1260D strain, a CYN1261D strain, a GX4 strain, a H-08-1320 strain, a H-1413-09 strain, a IP 1586/10 strain, a IP 2990/13 strain, a IP 2991/13 strain, a IP 2992/13 strain, a IP 3176/09 strain, a IP 4005/12 strain, a IP 412/10 strain, a IP 542/10 strain, a IP 7941/09 strain, a J strain, a JX-08-47 strain, a JX08-48 strain, a Kyoto strain, a Kyoto(G-S204N) strain, a N·HL strain, a RC·HL strain, a rHEP5.0-CVSG strain, a RRV ON-99-2 strain, a SAD-B19 strain, a SH06 strain, a SHRBV-18 strain, a SNK-CTN strain, a SRV9 strain, a Street Alabama Dufferin (HCP-SAD) strain, a VRC-RZ2 strain, a ZJ-LA strain, and a ZJ-QZ strain. In some embodiments, the envelope glycoprotein G is of a Flury LEP strain.

In some embodiments, the polypeptide construct comprises a molecular alteration that stabilizes the RABV-G, variant thereof, or antigenic determinant of either thereof.

In some embodiments, the modified alphavirus genome or srRNA comprises no nucleic acid sequence encoding viral structural proteins.

In some embodiments, the nucleic acid sequence encoding the polypeptide construct is operably linked to a promoter sequence. In some embodiments, the promoter sequence is a 26S subgenomic (sg) promoter.

In some embodiments, the modified alphavirus genome or srRNA is of an alphavirus belonging to the VEEV/EEEV group, or the SFV group, or the SINV group. In some embodiments, the alphavirus is Venezuelan equine encephalitis virus (VEEV), Eastern equine encephalitis virus (EEEV), Chikungunya virus (CHIKV), Western equine encephalitis virus (WEEV), or Sindbis virus (SINV).

In some embodiments, the nucleic acid sequence has at least 80%, at least 85%, at least 90%, at least 95%, at least 96%, at least 97%, at least 98%, at least 99%, or 100% sequence identity to a nucleic acid sequence selected from the group consisting of SEQ ID NOS: 6-11.

In one aspect, provided herein are recombinant cells including a nucleic acid construct as disclosed herein. In some embodiments, the recombinant cell is a mammalian cell or an insect cell.

In yet another aspect, provided herein are pharmaceutical compositions including a pharmaceutically acceptable excipient and a nucleic acid construct of the disclosure.

In some embodiments, the composition is formulated is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof. In some embodiments, the lipid is present in mass ratio of lipid to RNA from about 100:1 to about 4:1. In some embodiments, the lipid-based nanoparticles have an average diameter of about 25 nm to about 1000 nm. In some embodiments, the composition is formulated as a vaccine or an adjuvant. In some embodiments, the composition is formulated for intramuscular administration.

In another aspect, provided herein are methods for inducing an immune response or treating rabies infection in a subject in need thereof. The method includes administering to the subject a composition comprising a nucleic acid construct of the disclosure. In some embodiments, the method is a method for inducing an immune response. In some embodiments, the immune response is a neutralizing antibody response. In some embodiments, the neutralizing antibody response comprises a neutralizing antibody titer of equal to or greater than 0.5 IU/mL. In some embodiments, the composition is administered to the subject individually as a single prophylaxis or therapy (monotherapy) or as a first therapy in combination with at least one additional therapies.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 3 shows the results as well as corresponding statistics on wildtype RABV-G. (**<0.01).

DETAILED DESCRIPTION OF THE DISCLOSURE

Figure 1:
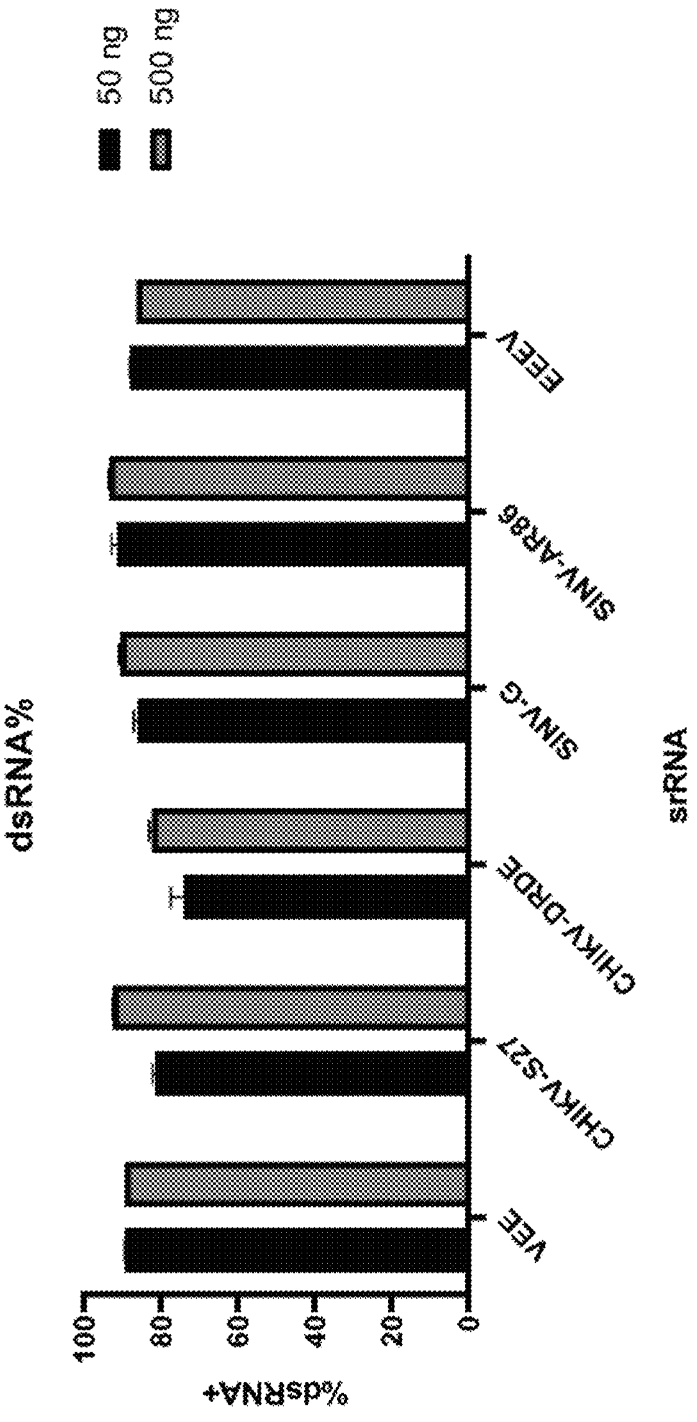
FIG. 1 is a bar chart that shows RNA replication from different srRNA vectors that encode rabies virus glycoprotein (RABV-G). srRNA was transfected at 50 or 500 ng into 7.7E5 BHK-21 cells by nucleofection and 15 hours later cells were collected and stained with an AF488-conjugated anti-dsRNA antibody. The frequency of dsRNA-positive cells was determined by flow cytometry (FC).

The present disclosure relates generally to nucleic acid constructs expressing variants or antigenic determinants of RABV-G for the purposes of both prophylactic and therapeutic treatment of rabies virus infection. These constructs address the problem with current rabies vaccines, due to the requirement of a 3-dose regimen within a short time frame to elicit immune protection and the need for regular boosters due to poor durability of immune responses. Provided herein are, inter alia, gene expression systems with superior expression potential which are suitable for expressing a coding sequence for a polypeptide construct comprising an envelope glycoprotein G of a rabies virus (RABV-G), a variant thereof, or an antigenic determinant of either thereof in recombinant cells. For example, some embodiments of the disclosure relate to nucleic acid constructs such as, e.g. expression constructs and vectors, containing a modified genome or srRNA of an alphavirus in which at least a portion of the nucleic acid sequence encoding the viral structural proteins of the modified alphavirus genome or srRNA has been replaced by a coding sequence for a polypeptide construct comprising an envelope glycoprotein G of a rabies virus (RABV-G), a variant thereof, or an antigenic determinant of either thereof. Further provided are recombinant cells that are genetically engineered to include one or more of the nucleic acid molecules disclosed herein. Biomaterials and recombinant products derived from such recombinant cells are also within the scope of the application. Also provided are compositions and methods useful for eliciting an immune response or treating rabies infection in a subject in need thereof.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The terms "administration" and "administering", as used herein, refer to the delivery of a bioactive composition or formulation by an administration route comprising, but not limited to, intranasal, transdermal, intravenous, intra-arterial, intramuscular, intranodal, intraperitoneal, subcutaneous, intramuscular, oral, intravaginal, and topical administration, or combinations thereof. The term includes, but is not limited to, administering by a medical professional and self-administering.

The terms "cell", "cell culture", and "cell line" refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the original cell, cell culture, or cell line.

The term "construct" refers to a recombinant molecule, e.g., recombinant nucleic acid or polypeptide, including one or more nucleic acid sequences or amino acid sequences from heterologous sources. For example, polypeptide constructs can be chimeric polypeptide molecules in which two or more amino acid sequences of different origin are operably linked to one another in a single polypeptide construct. Similarly, nucleic acid constructs can be chimeric nucleic acid molecules in which two or more nucleic acid sequences of different origin are assembled into a single nucleic acid molecule. Representative nucleic acid constructs can include any recombinant nucleic acid molecules, linear or circular, single stranded or double stranded DNA or RNA nucleic acid molecules, derived from any source, such as a plasmid, cosmid, virus, autonomously replicating polynucleotide molecule, phage, capable of genomic integration or autonomous replication, comprising a nucleic acid molecule where one or more nucleic acid sequences have been operably linked. Two or more nucleic acid constructs can be contained within a single nucleic acid molecule, such as a single vector, or can be containing within two or more separate nucleic acid molecules, such as two or more separate vectors.

The term "effective amount", "therapeutically effective amount", or "pharmaceutically effective amount" of a composition of the disclosure, e.g., nucleic acid constructs, srRNAs, recombinant cells, and/or pharmaceutical compositions, generally refers to an amount sufficient for the composition to accomplish a stated purpose relative to the absence of the composition (e.g., achieve the effect for which it is administered, stimulate an immune response, prevent or treat a disease, or reduce one or more symptoms of a disease, disorder, infection, or health condition). An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy,* 20th Edition, 2003, Gennaro, Ed., Lippincott, Williams & Wilkins).

The term "naked" as used herein when referencing nucleic acids that are substantially free of other macromolecules, such as lipids, polymers, and proteins. A "naked" nucleic acid, such as a self-replicating RNA, is not formulated with other macromolecules to improve cellular uptake. Accordingly, a naked nucleic acid is not encapsulated in, absorbed on, or bound to a liposome, a microparticle, a nanoparticle, a cationic emulsion, and the like.

The term "operably linked", as used herein, denotes a physical or functional linkage between two or more elements, e.g., polypeptide sequences or polynucleotide sequences, which permits them to operate in their intended fashion. For example, the term "operably linked" when used in context of the nucleic acid molecules described herein or the coding sequences and promoter sequences in a nucleic acid molecule means that the coding sequences and promoter sequences are in-frame and in proper spatial and distance away to permit the effects of the respective binding by transcription factors or RNA polymerase on transcription.

It should be understood that operably linked elements may be contiguous or non-contiguous (e.g., linked to one another through a linker). In the context of polypeptide constructs, "operably linked" refers to a physical linkage (e.g., directly or indirectly linked) between amino acid sequences (e.g., different segments, portions, regions, or domains) to provide for a described activity of the constructs. Operably linked segments, portions, regions, and domains of the polypeptides or nucleic acid molecules disclosed herein may be contiguous or non-contiguous (e.g., linked to one another through a linker).

The term "portion" as used herein refers to a fraction. With respect to a particular structure such as a polynucleotide sequence or an amino acid sequence or protein the term "portion" thereof may designate a continuous or a discontinuous fraction of said structure. For example, a portion of an amino acid sequence comprises at least 1%, at least 5%, at least 10%, at least 20%, at least 30%, at least 40%, at least 50%, at least 60%, at least 70%, at least 80%, and at least 90% of the amino acids of said amino acid sequence. In addition or alternatively, if the portion is a discontinuous fraction, said discontinuous fraction is composed of 2, 3, 4, 5, 6, 7, 8, or more parts of a structure (e.g., domains of a protein), each part being a continuous element of the structure. For example, a discontinuous fraction of an amino acid sequence may be composed of 2, 3, 4, 5, 6, 7, 8, or more, for example not more than 4 parts of said amino acid sequence, wherein each part comprises at least 1, at least 2, at least 3, at least 4, at least 5 continuous amino acids, at least 10 continuous amino acids, at least 20 continuous amino acids, or at least 30 continuous amino acids of the amino acid sequence.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI website at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, Nucleic Acids Res. 12:387, 1984), BLASTP, BLASTN, FASTA (Atschul et al., J Mol Biol 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "pharmaceutically acceptable excipient" as used herein refers to any suitable substance that provides a pharmaceutically acceptable carrier, additive, or diluent for administration of a compound(s) of interest to a subject. As such, "pharmaceutically acceptable excipient" can encompass substances referred to as pharmaceutically acceptable diluents, pharmaceutically acceptable additives, and pharmaceutically acceptable carriers. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics and additional therapeutic agents) can also be incorporated into the compositions.

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a health condition of interest (e.g., rabies infection) and/or one or more symptoms of the health condition. The subject can also be an individual who is diagnosed with a risk of the health condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

It is understood that aspects and embodiments of the disclosure described herein include "comprising", "consisting", and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In some embodiments, the genes, nucleic acid sequences, amino acid sequences, peptides, polypeptides and proteins are human. The term "gene" is also intended to include variants thereof.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Alphaviruses

Alphaviruses are small, enveloped RNA viruses with a single-stranded, positive-sense RNA genome. The alphavirus genus includes, inter alia, the Sindbis virus (SINV), the Semliki Forest virus (SFV), the Ross River virus (RRV), Venezuelan equine encephalitis virus (VEEV), and Eastern equine encephalitis virus (EEEV), which are all closely related and are able to infect various vertebrates such as mammalians, rodents, fish, avian species, and larger mammals such as humans and horses as well as invertebrates such as insects. In particular, the Sindbis and the Semliki Forest viruses have been widely studied and the life cycle, mode of replication, etc., of these viruses are well characterized.

The alphavirus genome is approximately 12 Kb long, and it consists of two open reading frames (ORFs): a 7 Kb frame encoding the nonstructural proteins (nsPs) and a 4 Kb frame encoding the structural polyprotein. The non-structural polyprotein (nsP) is cleaved into four different proteins (nsP1, nsP2, nsP3, and nsP4) which are necessary for the transcription and translation of viral mRNA inside the cytoplasm of host cells.

The nsP1 protein is an mRNA capping enzyme that possesses both guanine-7-methyltransferase (MTase) and guanylyltransferase (GTase) activities, where they direct the methylation and capping of newly synthesized viral genomic and subgenomic RNAs. The MTase motif in the N-terminal domain of nsP1 catalyzes the transfer of the methyl group from S-adenosylmethionine (AdoMet) to the N7 position of a GTP molecule (m7Gppp). GTase then binds the m7Gppp, forming a covalent link with a catalytic histidine (m7Gp-GTase) and releasing PPi. The GTase then transfers the m7Gp molecule to the 5'-diphosphate RNA to create m7GpppNp-RNA. The resulting cap structure is essential for viral mRNA translation and prevents the mRNA from being degraded by cellular 5' exonucleases. Following the N-terminal domain are features that allow the association of the nsP1 protein to cellular membranes. The presence of α-helical amphipathic loop and palmitoylation sites allow the nsP1 protein and nsP1-containing replication complex to anchor onto the plasma membrane, possibly through nsP1 interaction with the membrane's anionic phospholipids.

The nsP2 protein possesses numerous enzymatic activities and functional roles. The N-terminal region contains a helicase domain that has seven signature motif of Superfamily 1 (SF1) helicases. It functions as an RNA triphosphatase that performs the first of the viral RNA capping reactions. It also functions as a nucleotide triphosphatase (NTPase), fueling the RNA helicase activity. The C-terminal region of nsP2 contains a papain-like cysteine protease, which is responsible for processing the viral non-structural polyprotein. The protease recognizes conserved motifs within the polyprotein. This proteolytic function is highly regulated and is modulated by other domains of nsP2. The alphavirus nsP2 protein has also been described as a virulence factor responsible for the transcriptional and translational shutoff in infected host cells and the inhibition of interferon (IFN) mediated antiviral responses contributing to the controlling of translational machinery by viral factors.

The precise role(s) of alphavirus nsP3 protein in the replication complex is less clear. The nsP3 protein has three recognized domains: the N-terminal macrodomain with phosphatase activity and nucleic acid binding ability, the alphavirus unique domain (AUD) and the C-terminal hypervariable domain. It has been demonstrated that the deletion of this domain in SFV nsP3 resulted in low viral pathogenicity, suggesting its importance in viral RNA transcription regulation.

The nsP4 polymerase is the most highly conserved protein in alphaviruses, with the most divergent being >50% identical in amino acid sequence when compared with other alphaviral nsP4s. The nsP4 contains the core RNA-dependent RNA polymerase (RdRp) domain at the C-terminal end, determined to be solely responsible for the RNA synthetic properties of the viral replication complex. The RdRp participates in replicating the genomic RNA via a negative strand RNA and transcribing the 26S subgenomic RNA. The N-terminal domain is alphavirus-specific and can be partially disordered structurally.

The 5' two-thirds of the alphavirus genome encodes a number of non-structural proteins (nsPs) necessary for transcription and replication of viral RNA. These proteins are translated directly from the RNA and together with cellular proteins form the RNA-dependent RNA polymerase essential for viral genome replication and transcription of sgRNA. Four nsPs (nsP1-4) are produced as a single polyprotein constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises sgRNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The sgRNA is transcribed from the p26S subgenomic promoter present at the 3' end of the RNA sequence encoding the nsp4 protein. The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface.

Alphavirus replication has been reported to take place on membranous surfaces within the host cell. In the first step of the infectious cycle, the 5' end of the genomic RNA is translated into a polyprotein (nsP1-4) with RNA polymerase activity that produces a negative strand complementary to the genomic RNA. The sequence at the 3' end of the genomic RNA plays an important role in the initiation negative-strand synthesis, where a minimum number of adenylate residues has been identified to be essential for replication to occur. In particular, it has been previously reported that for alphavirus genomes to replicate, there must be at least 11 residues in the poly(A) tail following the 3' UTR to efficiently initiate minus-strand synthesis, and therefore replication to occur. It has also been previously reported that lengthening the poly(A) tail to 25 residues results in enhanced replication, but no further enhancement of replication was observed when the poly(A) was lengthened further to 34 residues. In addition, internal non-A residues in the poly(A) are most often deleterious to replication, which suggests that enzymatic poly(A) tailing would not benefit srRNA that did not exclusively contain 3' adenylate residues following the 3' UTR. It has been previously reported that there is no enhancement of minus-strand synthesis on RNA templates with greater than 25 adenylate residues in the poly(A) tail. In a second step of replication, the negative strand is used as a template for the production of two RNAs, respectively: (1) a positive genomic RNA corresponding to the genome of the secondary viruses producing, by translation, other nsPs and acting as a genome for the virus; and (2) sgRNA encoding the structural proteins of the virus forming the infectious particles. The positive genomic RNA/sgRNA ratio is regulated by proteolytic autocleavage of the polyprotein to nsP1, nsP2, nsP3 and nsP4. In practice, the viral gene expression takes place in two phases. In a first phase, there is main synthesis of positive genomic strands and of negative strands. During the second phase, the synthesis of sgRNA is virtually exclusive, thus resulting in the production of large amount of structural protein.

Self-Replicating RNA

As will be appreciated by the skilled artisan, the term "self-replicating RNA" refers to RNA molecule that contains all of the genetic information required for directing its own self-amplification or self-replication within a permissive cell. To direct its own replication, the srRNA generally (1) encodes polymerase, replicase, or other proteins which may interact with viral or host cell-derived proteins, nucleic acids or ribonucleoproteins to catalyze the RNA amplification process; and (2) contain cis-acting RNA sequences required for replication and transcription of the subgenomic RNA (sgRNA). These sequences may be bound during the process of replication to its self-encoded proteins, or non-self-encoded cell-derived proteins, nucleic acids or ribonucleoproteins, or complexes between any of these components. In some embodiments of the disclosure, an alphavirus srRNA construct generally contains the following elements: 5' viral or defective-interfering RNA sequence(s) required in cis for replication, sequences coding for biologically active alphavirus non-structural proteins (e.g., nsP1, nsP2, nsP3, and nsP4), a subgenomic promoter (sg) for the sgRNA, 3' viral sequences required in cis for replication, and optionally a polyadenylate tract (poly(A)). In some instances, a subgenomic promoter (sg) that directs expression of a heterologous sequence can be included in the srRNA construct of the disclosure.

Further, the term srRNA generally refers to a molecule of positive polarity, or "message" sense, and the srRNA may be of length different from that of any known, naturally-occurring alphavirus. In some embodiments of the present disclosure, the srRNA does not contain at least a portion of the coding sequence for one or more of the alphavirus structural proteins; and/or sequences encoding structural genes can be substituted with heterologous sequences. In those instances, where the srRNA is to be packaged into a recombinant alphavirus particle, it can contain one or more sequences, so-called packaging signals, which serve to initiate interactions with alphavirus structural proteins that lead to particle formation.

The srRNA constructs of the disclosure generally have a length of at least about 2 kb. For example, the srRNA can have a length of at least about 2 kb, at least about 3 kb, at least about 4 kb, at least about 5 kb, at least about 6 kb, at least about 7 kb, at least about 8 kb, at least about 9 kb, at least about 10 kb, at least about 11 kb, at least about 12 kb or more than 12 kb. In some embodiments, the srRNA can have a length of about 4 kb to about 20 kb, about 4 kb to about 18 kb, about 5 kb to about 16 kb, about 6 kb to about 14 kb, about 7 kb to about 12 kb, about 8 kb to about 16 kb, about 9 kb to about 14 kb, about 10 kb to about 18 kb, about 11 kb to about 16 kb, about 5 kb to about 18 kb, about 6 kb to about 20 kb, about 5 kb to about 10 kb, about 5 kb to about 8 kb, about 5 kb to about 7 kb, about 5 kb to about 6 kb, about 6 kb to about 12 kb, about 6 kb to about 11 kb, about 6 Kb to about 10 kb, about 6 Kb to about 9 Kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb. In some embodiments, the srRNA can have a length of about 6 kb to about 14 kb. In some embodiments, the srRNA can have a length of about 6 kb to about 16 kb.

Rabies Virus Envelope Glycoprotein G (RABV-G)

Rabies virus is bullet shaped with a length of about 180 nm and a diameter of 75 nm. The genome is non-segmented with negative sense single stranded RNA. The genome encodes five structural proteins 3' N-P-M-G-L 5'; N (nucleoprotein), P (phosphoprotein), M (matrix protein), G (glycoprotein) and L (RNA dependent RNA polymerase). The leader and trailer untranslated regions at the 3' and 5' ends of the genome flank the structural genes and between the protein encoding regions there are non-coding intergenic sequences; N-P, P-M, M-G, G-L.

Among the five structural proteins, G is present on the envelope and is the only protein exposed out. Glycoproteins are proteins which are covalently bonded with sugar units. Rabies virus glycoprotein (RABV-G) is a trimeric type I trans-membrane protein which are single pass type with extracellular N-terminus and cytoplasmic C-terminus for cell membrane. The precursor RABV-G is 524 amino acid (aa) in length (522 aa in Mokola virus), consisting of a signal peptide of 19 aa in the N terminal. The mature protein has N-terminal ectodomain (439 aa), a transmembrane segment (22 aa) and a cytoplasmic tail/endodomain/ENDO (44 aa). As the G protein covers the outer surface of the virion envelope and is the only target antigen, which is able to induce virus-neutralizing antibodies.

Compositions of the Disclosure

As described in greater detail below, one aspect of the present disclosure relates to nucleic acid constructs containing sequences that encode a modified alphavirus genome or srRNA where at least a portion of the nucleic acid sequence encoding the viral structural proteins of the modified alphavirus genome or srRNA has been replaced by an coding sequence for a polypeptide construct comprising an envelope glycoprotein G of a rabies virus (RABV-G), a variant thereof, or an antigenic determinant of either thereof. Also provided are recombinant cells and cell cultures that have been engineered to include a nucleic acid construct as disclosed herein.

Nucleic Acid Constructs

As described in greater detail below, one aspect of the present disclosure relates to nucleic acid constructs including a nucleic acid sequence encoding a modified genome or srRNA of an alphavirus where at least a portion of the nucleic acid sequence encoding the viral structural proteins of the modified alphavirus genome or srRNA has been replaced by a coding sequence for a polypeptide construct comprising an envelope glycoprotein G of a rabies virus (RABV-G), a variant thereof, or an antigenic determinant of either thereof. In some embodiments, the sequence encoding the nucleic acid construct can be operably linked, e.g., placed under the control of elements required for expression (e.g., promoter sequences), which allow expression of the srRNA construct in a host cell, in a subject, or in an ex-vivo cell-free expression system.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Non-limiting exemplary embodiments of the methods of the disclosure can include one or more of the following features. In some embodiments, the alphavirus srRNA vector is devoid of at least a portion of the nucleic acid sequence encoding one or more of the viral structural proteins CP, E1, E2, E3, and 6K of the alphavirus srRNA vector. In some embodiments, the alphavirus srRNA vector is devoid of a portion of or the entire sequence encoding CP. In some embodiments, the alphavirus srRNA vector is devoid of a portion of or the entire sequence encoding E1. In some embodiments, the alphavirus srRNA vector is devoid of a portion of or the entire sequence encoding E2. In some embodiments, the alphavirus srRNA vector is devoid of a portion of or the entire sequence encoding E3. In some embodiments, the alphavirus srRNA vector is devoid of a portion of or the entire sequence encoding 6K. In some embodiments, the alphavirus srRNA vector is devoid of a portion of or the entire sequence encoding a combination of CP, E1, E2, E3, and 6K. In some embodiments of the disclosure, the coding sequence for nonstructural proteins nsP1, nsP2, nsP3, and nsP4 of the alphavirus srRNA vector is present, however at least a portion of or the entire sequence encoding one or more structural proteins (e.g., CP, E1, E2, E3, and 6K) of the alphavirus srRNA vector is absent.

In some embodiments, the alphavirus srRNA vector is devoid of a substantial portion of the nucleic acid sequence encoding one or more viral structural proteins. The skilled artisan will understand that a substantial portion of a nucleic acid sequence encoding a viral structural polypeptide can include enough of the nucleic acid sequence encoding the viral structural polypeptide to afford putative identification of that polypeptide, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993). Accordingly, a substantial portion of a nucleotide sequence comprises enough of the sequence to afford specific identification and/or isolation of a nucleic acid fragment comprising the sequence. For example, a substantial portion of a nucleic acid sequence can include at least about 20%, for example, about 30%, about 40%, about 50%, about 60%, about 70%, about 80%, about 90%, about 95% of the full length nucleic acid sequence.

In some embodiments, the alphavirus srRNA vector is devoid of the entire sequence encoding viral structural proteins, e.g., the alphavirus srRNA vector includes no nucleic acid sequence encoding the viral structural proteins.

The nucleic acid constructs of the disclosure further include a coding sequence for a polypeptide construct that replaces at least a portion of the nucleic acid sequence encoding the viral structural proteins of the modified alphavirus genome or srRNA. In principle, the nucleic acid constructs disclosed herein can generally include any number of coding sequences for a polypeptide construct. In some embodiments, the nucleic acid constructs disclosed herein can include at least one, at least two, at least three, at least four, at least five, or at least six coding sequences for a polypeptide constructs. A coding sequence for a polypeptide construct can be a construct of genetic material that contains coding sequences and enough regulatory information to direct proper transcription and/or translation of the coding sequences in a cell, in vivo and/or ex vivo. The coding sequence for a polypeptide construct can be inserted into a vector for targeting to a desired host cell and/or into a subject. Accordingly, in some embodiments, the term "coding sequence for a polypeptide construct" can be used interchangeably with the term "expression construct." In some embodiments, a coding sequence for a polypeptide construct can be a nucleic acid construct that includes a gene encoding a protein or functional RNA operably linked to regulatory elements such as, for example, a promoter and/or a termination signal, and optionally, any or a combination of other nucleic acid sequences that affect the transcription or translation of the gene.

The nucleic acid constructs described herein include a coding sequence for an envelope glycoprotein G of a rabies virus (RABV-G), a variant thereof, or an antigenic determinant of either thereof, which encode polypeptides containing epitopes that are able to elicit an immune response. The variants of RABV-G can encompass coding sequences for polypeptides having an amino acid sequence that is the same or essentially the same as that of the reference protein (e.g., RABV-G) except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein. The terms "variant", when used in reference to a nucleic acid sequence, refer to a nucleic acid sequence that differs by one or more nucleotides from another, usually related nucleotide acid sequence. As such, the term "variant" can refer to a change of one or more nucleotides of a reference nucleic acid which includes the insertion of one or more new nucleotides, deletion of one or more nucleotides, and substitution of one or more existing nucleotides. A variant can also include a point mutation, multiple mutation, single nucleotide polymorphism (SNP), deletion, insertion, and translocation. Thus, variants of the coding sequences described herein include nucleic acids that encode polypeptides that can be, for example, full length, mutated, truncated, inactivated, peptide/epitopes or combinations thereof of RABV-G.

The nucleic acid constructs described herein can also include a coding sequence for an envelope glycoprotein G of a rabies virus (RABV-G), or an antigenic determinant thereof. In some embodiments, the antigenic determinant resides within the N-terminal half of rabies virus G glycoprotein. Other particular antigenic determinants reside within the C-terminal half of rabies virus. Such antigenic determinants can reside, for example, within amino acids 1-50, 50-100, 100-150, 150-200, 200-250, 250-300, 300-350, 350-400, 400-450, 450-500, 500-524 of rabies virus G glycoprotein, or any interval, portion or range thereof. In one embodiment, the antigenic determinant resides within the N-terminal half of rabies virus G glycoprotein, i.e., between about amino acid residues 19-422. In another embodiment, the antigenic determinant resides within the C-terminal half of the rabies virus G glycoprotein, i.e., between about amino acid residues 1-19. In another embodiment, the antigenic determinant of the rabies G glycoprotein comprises amino acid residues 336-442. In one embodiment, the rabies G glycoprotein comprises amino acid residue 336 as well as alterations thereof, such as substitutions or deletions.

In some embodiments, the rabies G glycoprotein antigenic determinant comprises one or more epitopes. Non-limiting examples of epitopes include linear epitope, conformational epitope, discontinuous epitope, or combinations of such epitopes. One skilled in the art will understand that the term "epitope" refers to an antigenic determinant that interacts with a specific antigen-binding site of an antigen-binding polypeptide, e.g., a variable region of an antibody molecule, known as a paratope. A single antigen can have more than one epitope. Thus, different antibodies may bind to different areas on an antigen and may have different biological effects. The term "epitope" also refers to a site on an antigen to which B cells respond. It also refers to a region of an antigen that is bound by an antibody. Epitopes can be defined as structural or functional. Functional epitopes are generally a subset of the structural epitopes and have those residues that directly contribute to the affinity of the interaction. Epitopes can be linear or conformational, that is, composed of non-linear amino acids. In certain embodiments, epitopes can include determinants that are chemically active surface groupings of molecules such as amino acids, sugar side chains, phosphoryl groups, or sulfonyl groups, and, in certain embodiments, can have specific three-dimensional structural characteristics, and/or specific charge characteristics.

In another related embodiment, the rabies G glycoprotein antigenic determinant comprises or consists of antigenic site I, antigenic site II, antigenic site III, antigenic site IV, antigenic site minor A, or combinations of such antigenic sites, for example, antigenic site III and minor site A. Antigenic sites of rabies virus have been identified using panels of monoclonal antibodies and their respective monoclonal antibody-resistant virus variants. The majority of rabies virus-neutralizing monoclonal antibodies are directed against antigenic site II (Benmansour et al., "Antigenicity of Rabies Virus Glycoprotein," *J. Virol.* 65:4198-4203 (1991), which is hereby incorporated by reference), which is a discontinuous conformational epitope comprising aa 34 to 42 and aa 198 to 200 (Prosniak, et al. 2003. Development of a cocktail of recombinant-expressed human rabies virus-neutralizing monoclonal antibodies for postexposure prophylaxis of rabies. J. Infect. Dis. 188:53-56). Antigenic site III is a continuous conformational epitope at aa 330 to 338 and harbors two charged residues, K330 and R333, that affect viral pathogenicity (Coulon et al 1998. An avirulent mutant of rabies virus is unable to infect motoneurons in vivo and in vitro. J. Virol. 72:273-278; Dietzschold et al. 1983. Characterization of an antigenic determinant of the glycoprotein that correlates with pathogenicity of rabies virus. Proc. Natl. Acad. Sci. USA 80:70-74; Seif et al. 1985. Rabies virulence: effect on pathogenicity and sequence characterization of rabies virus mutations affecting antigenic site III of the glycoprotein. J. Virol. 53:926-934). The conformational antigenic site I was defined by only one monoclonal antibody, 509-6, located at aa 231 (Benmansour et al., "Antigenicity of Rabies Virus Glycoprotein," *J. Virol.* 65:4198-4203 (1991); Lafon et al. 1983. Antigenic sites on the CVS rabies virus glycoprotein: analysis with monoclonal antibodies. J. Gen. Virol. 64:843-8451). Antigenic site IV is known to harbor overlapping linear epitopes (Bunschoten et al., 1989. Characterization of a new virus-neutralizing epitope that denotes a sequential determinant on the rabies virus glycoprotein. J. Gen. Virol. 70:291-298; Luo et al. 1997. A virus-neutralizing epitope on the glycoprotein of rabies virus that contains Trp251 is a linear epitope. Virus Res. 51:35-41; Ni et al. 1995. Mapping and characterization of a sequential epitope on the rabies virus glycoprotein which is recognized by a neutralizing monoclonal antibody, RG719. Microbiol. Immunol. 39:693-702). Benmansour et al. also described the presence of a minor site located at position 342 to 343, which is distinct from antigenic site III despite its close proximity.

The RABV-G of the nucleic acid constructs described herein can be from a virulent rabies virus strain or an avirulent rabies virus strain.

The anti-rabies vaccines currently in use are either vaccines made from inactivated viruses or vaccines consisting of viral strains with attenuated virulence or recombinant viruses.

Viruses can be inactivated by a variety of methods, in particular chemical methods such as treatment with formaldehyde or 3-propiolactone.

The attenuation of the virulence of viral strains is well known; for example, it may be carried out by successive passages of viral strains on a different host, vector type (e.g. rabbit or mouse) or in cell cultures. Thus, strains are poorly adapted to the host source and therefore less pathogenic to the host, while maintaining their vaccination capacity.

Avirulent rabies strains often include one or more mutations in the envelope glycoprotein G (see, e.g., Flamand et al., "Avirulent Mutants of Rabies Virus and Their Use as Live Vaccine," Trends Microbiol. 1(8):317-20 (1993); Coulon et al., "An Avirulent Mutant of Rabies Virus is Unable to Infect Motorneurons In Vivo and In Vitro," J. Virol. 72(1): 273-278 (1998)). By way of example, antigenic mutants of RABV-G isolated from either the challenge virus standard strain (CVS), CVS derivatives, or the Street-Alabama-Dufferin (SAD) Bern strain, which have the arginine (Arg) at positon 333 in G replaced by either a glutamine (Gln), a glycine (Gly), a leucine, an isoleucine, a methionine, a cysteine, or a serine, are avirulent (Tuffereau et al., Arginine or lysine in position 333 of ERA and CVS glycoprotein is necessary for rabies virulence in adult mice. *Virology.* 1989; 172: 206-212; Seif et al., Rabies virulence: effect on pathogenicity and sequence characterization of rabies virus mutations affecting antigenic site III of the glycoprotein. *J Virol.* 1985; 53: 926-934). In addition, recombinant viruses that have the Arg at position 333 in G replaced by a glutamic acid are also avirulent (McGettigan et al., Second-generation rabies virus-based vaccine vectors expressing human immunodeficiency virus type 1 gag have greatly reduced pathogenicity but are highly immunogenic. *J Virol.* 2003; 77: 237-244). Thus, in general, RABV becomes avirulent when the Arg or Lys at position 333 in G is changed to other amino acids.

In principle, there are no particular limitations to the rabies virus strains from which the envelope glycoprotein G can be derived from. Non-limiting examples of rabies virus strains suitable for the compositions and methods disclosed herein include a Flury LEP strain, a Flury LEP-C strain, a Flury HEP strain, a 1088 strain, a AT6 strain, a CQ92 strain, a CVS-11 strain, a CVS-26 strain, a CVS-26(G-N204S) strain, a CYN1009D strain, a CYN1026D strain, a CYN1029D strain, a CYN1138D strain, a CYN1140D strain, a CYN1141D strain, a CYN1242H strain, a CYN1243D strain, a CYN1244D strain, a CYN1245D strain, a CYN1247D strain, a CYN1249D strain, a CYN1250D strain, a CYN1251D strain, a CYN1252D strain, a CYN1253D strain, a CYN1255D strain, a CYN1256D strain, a CYN1257D strain, a CYN1259D strain, a CYN1260D strain, a CYN1261D strain, a GX4 strain, a H-08-1320 strain, a H-1413-09 strain, a IP 1586/10 strain, a IP 2990/13 strain, a IP 2991/13 strain, a IP 2992/13 strain, a IP 3176/09 strain, a IP 4005/12 strain, a IP 412/10 strain, a IP 542/10 strain, a IP 7941/09 strain, a J strain, a JX-08-47 strain, a JX08-48 strain, a Kyoto strain, a Kyoto (G-S204N) strain, a N·HL strain, a RC·HL strain, a rHEP5.0-CVSG strain, a RRV ON-99-2 strain, a SAD-B19 strain, a SH06 strain, a SHRBV-18 strain, a SNK-CTN strain, a SRV9 strain, a Street Alabama Dufferin (HCP-SAD) strain, a VRC-RZ2 strain, a ZJ-LA strain, and a ZJ-QZ strain. In some embodiments, the envelope glycoprotein G is of a Flury LEP strain.

The full-length amino acid sequence of a non-limiting RABV-G protein is set forth in SEQ ID NO: 1 as follows:

MVPQVLLFVPLLGFSLCFGKFPIYTIPDKLGPWSPIDIHHLSCPNNLVVEDEGCTNLSE FSYMELKVGYISAIKVNGFTCTGVVTEAETYTNFVGYVTTTFKRKHFRPTPDACRAA YNWKMAGDPRYEESLHNPYPDYHWLRTVKTTKESLVIISPSVTDLDPYDKSLHSRV FPGGNCSGITVSSTYCSTNHDYTIWMPENLRLGTSCDIFTNSRGKRASKGGKTCGFVDERGLYKSLKGACKLKLCGVLGLRLMDGTWVAMQTSDETKWCPPGQLVNLHDFR SDEIEHLVVEELVKKREECLDALESIMTTKSVSFRRLSHLRKLVPGFGKAYTIFNKTL MEADAHYKSVRTWNEIIPSKGCLRVGGRCHPHVNGVFFNGIILGSDGHVLIPEMQSS LLQQHMELLESSVIPLMHPLADPSTVFKDGDEVEDFVEVHLPDVHEQVSGVELGLPN WGKYVLMIAGALIALMLIIFLMTCCRRVNRPESTQSSLGETGRNVSVTSQSGKVISSWESYKSGGETRL

In some embodiments, the coding sequence for RABV-G in the nucleic acid constructs described herein encodes the amino acid sequence of SEQ ID NO: 1. In some embodiments, the nucleic acid constructs of the disclosure include a nucleic acid sequence encoding a RABV-G having at least 80%, at least 85%, at least 90%, at least 95%, at least 96%, at least 97%, at least 98%, at least 99%, or 100% sequence identity to an amino acid sequence of SEQ ID NO: 1. In some embodiments, the nucleic acid constructs of the disclosure include a nucleic acid sequence encoding a RABV-G having the amino acid sequence of SEQ ID NO: 1, wherein one, two, three, four, or five of the amino acid residues in a SEQ ID NO: 1 is/are substituted by a different amino acid residue. In some embodiments, the coding sequence for RABV-G encodes smaller portions of the amino acid sequence of SEQ ID NO: 1. For example, these smaller portions can include at least 8, 10, 12, 14, 16, 18, 20, 30 or more amino acids of SEQ ID NO: 1.

In some embodiments, the nucleic acid construct as described herein comprises a nucleic acid sequence has at least 80%, at least 85%, at least 90%, at least 95%, at least 96%, at least 97%, at least 98%, at least 99%, or 100% sequence identity to a nucleic acid sequence of SEQ ID NOs: 6-11.

In some embodiments, the coding sequence of RABV-G is redesigned and/or optimized for a desired property, such as increased stability, potency, and expression (e.g., translation efficiency), which in turns can maximize the impact of producing, delivering, and administering biotherapeutic. For example, in some embodiments, the coding sequence is optimized for expression at a level higher than the expression level of a reference coding sequence. With respect to sequence-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the nucleic acid constructs of the present disclosure may also have any base sequence that has been changed from any polynucleotide sequence disclosed herein by substitution in accordance with degeneracy of the genetic code. References describing codon usage are readily publicly available. In some embodiments, polynucleotide sequence variants can be produced for a variety of reasons, e.g., to optimize expression for a particular host (e.g., changing codon usage in the alphavirus mRNA to those preferred by other organisms such as human, non-human primates, hamster, mice, or monkey). Accordingly, in some embodiments, the coding sequence is optimized for expression in a target host cell through the use of codons optimized for expression. The techniques for the construction of synthetic nucleic acid sequences encoding genes using preferred codons optimal for host cell expression may be determined by computational methods analyzing the commonality of codon usage for encoding native proteins of the host cell genome and their relative abundance by techniques well known in the art. The codon usage database (http://www.kazusa.or.jp/codon) may be used for generation of codon optimized sequences in mammalian cell environments. Furthermore, a variety of software tools are available to convert sequences from one organism to the optimal codon usage for a different host organism such as the JCat Codon Optimization Tool (www.jcat.de), Integrated DNA Technologies (IDT) Codon Optimization Tool (https://www.idtdna.com/CodonOpt) or the Optimizer online codon optimization tool (http://genomes.urv.es/OPTIMIZER). Such synthetic sequences may be constructed by techniques known in the art for the construction of synthetic nucleic acid molecules and may be obtained from a variety of commercial vendors.

In some embodiments, the coding sequence is optimized for enhanced RNA stability and/or expression. The stability of RNA generally relates to the "half-life" of RNA. "Half-life" relates to the period of time which is needed to eliminate half of the activity, amount, or number of molecules. In the context of the present disclosure, the half-life of an RNA is indicative for the stability of said RNA. The half-life of RNA may influence the "duration of expression" of the RNA. Additional information regarding principles, strategies, and methods for use in enhancing RNA stability can be found at, for example, Leppek K. et al., *Combinatorial optimization of mRNA structure, stability, and translation for RNA-based therapeutics*. bioRxiv. (Preprint). Mar. 30, 2021. doi: 10.1101/2021.03.29.437587.

Recombinant Cells

The nucleic acid constructs of the present disclosure can be introduced into a host cell to produce a recombinant cell containing the nucleic acid molecule. Accordingly, prokaryotic or eukaryotic cells that contain a nucleic acid construct encoding a modified alphavirus genome as described herein are also features of the disclosure. In a related aspect, some embodiments disclosed herein relate to methods of transforming a cell which includes introducing into a host cell, such as an animal cell, a nucleic acid construct as provided herein, and then selecting or screening for a transformed cell. Introduction of the nucleic acid constructs of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, direct micro-injection, nanoparticle-mediated nucleic acid delivery, and the like.

In one aspect, some embodiments of the disclosure relate to recombinant cells, for example, recombinant animal cells that include a nucleic acid construct described herein. The nucleic acid construct can be stably integrated in the host genome, or can be episomally replicating, or present in the recombinant host cell as a mini-circle expression vector for a stable or transient expression. Accordingly, in some embodiments of the disclosure, the nucleic acid construct is maintained and replicated in the recombinant host cell as an episomal unit. In some embodiments, the nucleic acid construct is stably integrated into the genome of the recombinant cell. Stable integration can be completed using classical random genomic recombination techniques or with more precise genome editing techniques such as using guide RNA directed CRISPR/Cas9 or TALEN genome editing. In some embodiments, the nucleic acid construct present in the recombinant host cell as a mini-circle expression vector for a stable or transient expression.

In some embodiments, the recombinant cell is a prokaryotic cell, such as the bacterium *E. coli*, or a eukaryotic cell, such as an insect cell (e.g., a mosquito cell or a Sf21 cell), or mammalian cells (e.g., COS cells, NIH 3T3 cells, or HeLa cells). In some embodiments, the cell is in vivo. In some embodiments, the cell is ex vivo. In some embodiments, the cell is in vitro. In some embodiments, the recombinant cell is a eukaryotic cell. In some embodiments, the recombinant cell is an animal cell. In some embodiments, the animal cell is a vertebrate animal cell or an invertebrate animal cell. In some embodiments, the recombinant cell is a mammalian cell. Suitable recombinant cells include a monkey kidney CV1 cell transformed by SV40 (COS-7), a human embryonic kidney cell (e.g., HEK 293 or HEK 293 cell), a baby hamster kidney cell (BHK), a mouse sertoli cell (e.g., TM4 cells), a monkey kidney cell (CV1), a human cervical carcinoma cell (HeLa), a canine kidney cell (MDCK), a buffalo rat liver cell (BRL 3A), a human lung cell (W138), a human liver cell (Hep G2), a mouse mammary tumor (MMT 060562), a TRI cell, a FS4 cell, a Chinese hamster ovary cell (CHO cell), an African green monkey kidney cell (Vero cell), a human A549 cell, a human cervix cell, a human CHME5 cell, a human PER.C6 cell, a NS0 murine myeloma cell, a human epidermoid larynx cell, a human fibroblast cell, a human HUH-7 cell, a human MRC-5 cell, a human muscle cell, a human endothelial cell, a human astrocyte cell, a human macrophage cell, a human RAW 264.7 cell, a mouse 3T3 cell, a mouse L929 cell, a mouse connective tissue cell, a mouse muscle cell, and a rabbit kidney cell.

In some embodiments, the recombinant cell is an insect cell, e.g., cell of an insect cell line. In some embodiments, the recombinant cell is a Sf21 cell. Additional suitable insect cell lines include, but are not limited to, cell lines established from insect orders Diptera, Lepidoptera and Hemiptera, and can be derived from different tissue sources. In some embodiments, the recombinant cell is a cell of a lepidopteran insect cell line. In the past few decades, the availability of lepidopteran insect cell lines has increased at about 50 lines per decade. More information regarding available lepidopteran insect cell lines can be found in, e.g., Lynn D. E., *Available lepidopteran insect cell lines*. Methods Mol Biol.

2007; 388:117-38, which is herein incorporated by reference. In some embodiments, the recombinant cell is a mosquito cell, e.g., a cell of mosquito species within *Anopheles* (An.), *Culex* (Cx.) and *Aedes* (Stegomyia) (Ae.) genera. Exemplary mosquito cell lines suitable for the compositions and methods described herein include cell lines from the following mosquito species: *Aedes aegypti, Aedes albopictus, Aedes pseudoscutellaris, Aedes triseriatus, Aedes vexans, Anopheles gambiae, Anopheles stephensi, Anopheles albimanus, Culex quinquefasciatus, Culex theileri, Culex tritaeniorhynchus, Culex bitaeniorhynchus*, and *Toxorhynchites amboinensis*. Suitable mosquito cell lines include, but are not limited to, CCL-125, Aag-2, RML-12, C6/26, C6/36, C7-10, AP-61, A.t. GRIP-1, A.t. GRIP-2, UM-AVE1, Mos.55, Sua1B, 4a-3B, Mos.43, MSQ43, and LSB-AA695BB. In some embodiments, the mosquito cell is a cell of a C6/26 cell line.

In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

The recombinant polypeptides produced by the method disclosed herein are also within the scope of the disclosure.

Non-limiting exemplary embodiments of the disclosed methods for producing a recombinant polypeptide can include one or more of the following features. In some embodiments, the methods for producing a recombinant polypeptide of the disclosure further include isolating and/or purifying the produced polypeptide. In some embodiments, the methods for producing a polypeptide of the disclosure further include structurally modifying the produced polypeptide to increase half-life.

Pharmaceutical Compositions

The nucleic acid constructs, recombinant cells, recombinant polypeptides of the disclosure can be incorporated into compositions, including pharmaceutical compositions. Such compositions generally include one or more of the nucleic acid constructs, recombinant cells, recombinant polypeptides described and provided herein, and a pharmaceutically acceptable excipient, e.g., carrier. In some embodiments, the compositions of the disclosure are formulated for the prevention, treatment, or management of rabies infection. For example, the compositions of the disclosure can be formulated as a prophylactic composition, a therapeutic composition, or a pharmaceutical composition comprising a pharmaceutically acceptable excipient, or a mixture thereof. In some embodiments, the compositions of the present disclosure are formulated for use as a vaccine. In some embodiments, the compositions of the present application are formulated for use as an adjuvant.

Accordingly, in one aspect, provided herein are pharmaceutical compositions including a pharmaceutically acceptable excipient and: a) a nucleic acid construct of the disclosure; b) a recombinant cell of the disclosure; and/or c) a recombinant polypeptide of the disclosure.

Non-limiting exemplary embodiments of the pharmaceutical compositions of the disclosure can include one or more of the following features. The nucleic acid constructs of the disclosure can be used in a naked form or formulated with a delivery vehicle. Exemplary routes, either using in a free form, e.g., inserted into a nucleic acid, e.g., a vector. For example, as described in greater detail below, a nucleic acid construct as described herein can be used as a vaccine.

For use in a pharmaceutical composition of the disclosure, a nucleic acid, or a recombinant cell as described herein can be formulated into or with delivery vehicles. Exemplary delivery vehicles suitable for the compositions and methods of the disclosure include, but are not limited to liposomes (e.g., neutral or anionic liposomes), microspheres, immune stimulating complexes (ISCOMS), lipid-based nanoparticles (LNP), polymer nanoparticles, viral replicon particles (VRPs), or conjugated with bioactive ligands, which can facilitate delivery and/or enhance the immune response. These compounds are readily available to one skilled in the art; for example, see Liposomes: A Practical Approach, RCP New Ed, TRL press (1990). Adjuvants other than liposomes and the like are also used and are known in the art. Adjuvants may protect the antigen (e.g., srRNA construct) from rapid dispersal by sequestering it in a local deposit, or they may contain substances that stimulate the host to secrete factors that are chemotactic for macrophages and other components of the immune system. An appropriate selection can be made by those skilled in the art, for example, from those described below.

Accordingly, in some embodiments, a composition of the disclosure can include one or more of the following: physiologic buffer, a liposome, a lipid-based nanoparticle (LNP), a polymer nanoparticle, a viral replicon particle (VRP), a microsphere, an immune stimulating complex (ISCOM), a conjugate of bioactive ligand, or a combination of any thereof.

In some embodiments, the nucleic acid constructs of the disclosure can be delivered to a cell or a subject by a lipid-based nanoparticle (LNP). LNP are generally less immunogenic than viral particles. While many humans have preexisting immunity to viral particles there is no preexisting immunity to LNP. In addition, adaptive immune response against LNP is unlikely to occur which enables repeat dosing of LNP.

The lipids suitable for the compositions and methods described herein can be cationic lipids, ionizable cationic lipids, anionic lipids, or neutral lipids.

In some embodiments, the LNP of the disclosure can include one or more ionizable lipids. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes lipids that assume a positive charge on pH decrease from physiological pH, and any of a number of lipid species that carry a net positive charge at a selective pH, such as physiological pH. Permanently cationic lipids such as DOTMA have proven too toxic for clinical use. The ionizable lipid can be present in lipid formulations according to other embodiments, preferably in a ratio of about 30 to about 70 Mol %, in some embodiments, about 30 Mol %, in other embodiments, about 40 Mol %, in other embodiments, about 45 Mol % in other embodiments, about 47.5 Mol % in other embodiments, about 50 Mol %, in still other embodiments, and about 60 Mol % in yet others ("Mol %" means the percentage of the total moles that is of a particular component). The term "about" in this paragraph signifies a plus or minus range of 5 Mol %. DODMA, or 1,2-dioleyloxy-3-dimethylaminopropane, is an ionizable lipid, as is DLin-MC3-DMA or 0-(Z,Z,Z,Z-heptatriaconta-6,9,26,29-tetraen-19-yl)-4-(N,N-dimethylamino) ("MC3").

Exemplary ionizable lipids suitable for the compositions and methods of the disclosure includes those described in PCT publications WO2020252589A1 and WO2021000041A1, U.S. Pat. Nos. 8,450,298 and 10,844,028, and Love K. T. et al., *Proc Natl Acad Sci USA*, Feb. 2, 2010 107 (5) 1864-1869, all of which are hereby incorporated by reference in their entirety. Accordingly, in some embodiments, the LNP of the disclosure includes one or more lipid compounds described in Love K. T. et al., 2010 supra, such as C16-96, C14-110, and C12-200. In some embodiments, the LNP includes an ionizable cationic lipid. Suitable ionizable cationic lipids include the group consisting of ALC-0315, C12-200, LN16, MC3, MD1, SM-102, and a combination of any thereof. In some embodiments, the LNP of the disclosure includes C12-200. The structure of C12-200 lipid is known in the art and described in, e.g., U.S. Pat. Nos. 8,450,298 and 10,844,028, which are hereby incorporated by reference in their entirety. In some embodiments the C12-200 is combined with cholesterol, C14-PEG2000, and DOPE. In some embodiments, the C12-200 is combined with DSPC and DMG-PEG2000.

In some embodiments, the LNP of the disclosure includes one or more cationic lipids. Suitable cationic lipids include, but are not limited to, 98N12-5, C12-200, C14-PEG2000, DLin-KC2-DMA (KC2), DLin-MC3-DMA (MC3), XTC, MD1, and 7C1. In some embodiments, the LNP of the disclosure includes one or more neutral lipids. Non-limiting neutral lipids suitable for the compositions and methods of the disclosure include DPSC, DPPC, POPC, DOPE, and SM. In some embodiments, the LNP of the disclosure includes one or more ionizable lipid compounds described in PCT publications WO2020252589A1 and WO2021000041A1, which are hereby incorporated by reference in their entirety.

A number of other lipids or combination of lipids that are known in the art can be used to produce a LNP. Non-limiting examples of lipids suitable for use to produce LNPs include DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Non-limiting examples of cationic lipids include 98N12-5, C12-200, C14-PEG2000, DLin-KC2-DMA (KC2), DLin-MC3-DMA (MC3), XTC, MD1, 7C1, and a combination of any thereof. Non-limiting examples of neutral lipids include DPSC, DPPC, POPC, DOPE, and SM. Non-limiting examples of PEG-modified lipids include PEG-DMG, PEG-CerC14, and PEG-CerC20.

In some embodiments, the LNP of the disclosure includes at least one lipid. Suitable lipids include C12-200, C14-PEG2000, DOPE, DMG-PEG2000, DSPC, DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). In some embodiments the C12-200 is combined with cholesterol, C14-PEG2000, and DOPE. In some embodiments, the C12-200 is combined with DSPC and DMG-PEG2000.

In some embodiments, the mass ratio of lipid to nucleic acid in the LNP delivery system is about 100:1 to about 3:1, about 70:1 to 10:1, or 16:1 to 4:1. In some embodiments, the mass ratio of lipid to nucleic acid in the LNP delivery system is about 16:1 to 4:1. In some embodiments, the mass ratio of lipid to nucleic acid in the LNP delivery system is about 20:1. In some embodiments, the mass ratio of lipid to nucleic acid in the LNP delivery system is about 8:1. In some embodiments, the lipid-based nanoparticles have an average diameter of less than about 1000 nm, about 500 nm, about 250 nm, about 200 nm, about 150 nm, about 100 nm, about 75 nm, about 50 nm, or about 25 nm. In some embodiments, the LNPs have an average diameter ranging from about 70 nm to 100 nm. In some embodiments, the LNPs have an average diameter ranging from about 88 nm to about 92 nm, from 82 nm to about 86 nm, or from about 80 nm to about 95 nm.

In some embodiments, the compositions of the disclosure that formulated in a liposome. In some embodiments, the compositions of the disclosure that formulated in a lipid-based nanoparticle (LNP). In some embodiments, the compositions of the disclosure that formulated in a polymer nanoparticle.

As described above, neural lipids, also known as "structural lipids" or "helper lipids" can also be incorporated into lipid formulations and lipid particles in some embodiments. The lipid formulations and lipid particles can include one or more structural lipids at about 10 to 40 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phosphoethanolamine (trans DOPE).

In another embodiment, the structural lipid can be any lipid that is negatively charged at physiological pH. These lipids include phosphatidylglycerols such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizing agents can be included in lipid formulations embodiments to ensure integrity of the mixtures. Stabilizing agents are a class of molecules which disrupt or help form the hydrophobic-hydrophilic interactions among molecules. Suitable Stabilizing agents include, but are not limited to, polysorbate 80 (also known as Tween 80, 1UPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate), and Brij™ S10 (Polyoxyethylene (10) stearyl ether). Polyethylene glycol conjugated lipids may also be used. The stabilizing agents may be used alone or in combinations with each other.

In some embodiments, the stabilizing agents comprises about 0.1 to 3 Mol % of the overall lipid mixture. In some embodiments, the stabilizing agents comprise about 0.5 to 2.5 Mol % of the overall lipid mixture. In some embodiments, the stabilizing agent is present at greater than 2.5 Mol %. In some embodiments the stabilizing agent is present at 5 Mol %. In some embodiments the stabilizing agent is present at 10 Mol %. In some embodiments, the stabilizing agent is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth. In other embodiments, the stabilizing agent is 2.6-10 Mol % of the lipid mixture. In other embodiments, the stabilizing agents is present at greater than 10 Mol % of the lipid mixture.

Steroids can also be included in the lipid compositions for certain applications, and lipid particles made therefrom include sterols, such as cholesterol and phytosterol.

In some embodiments, the therapeutic compositions described herein, e.g., nucleic acid constructs, recombinant cells, recombinant polypeptides, and/or pharmaceutical compositions are incorporated into therapeutic compositions for use in methods of preventing or treating a subject who has, who is suspected of having a rabies infection. A subject suspected of having a rabies infection can be one bitten by an animal having or suspected of having a rabies infection such as a raccoon, skunk, fox, coyote, bat, dog, cat, etc.

In some embodiments, the compositions are immunogenic compositions, e.g., composition that can stimulate an immune response in a subject. In some embodiments, the immunogenic compositions are formulated as a vaccine. In some embodiments, the pharmaceutical compositions are formulated as an adjuvant. In some embodiments, the immunogenic compositions are formulated as a biotherapeutic, e.g., vehicle for gene delivery of different molecules with bioactivity. Non-limiting examples of biotherapeutic include cytokines, chemokines, and other soluble immunomodulators, enzymes, peptide and protein agonists, peptide and protein antagonists, hormones, receptors, antibodies and antibody-derivatives, growth factors, transcription factors, and gene silencing/editing molecules. In some embodiments, the pharmaceutical compositions are formulated as an adjuvant.

In some embodiments, the immunogenic compositions are substantially non-immunogenic or minimally immunogenic (e.g. compositions that minimally stimulate an immune response in a subject. In some embodiments, the non-immunogenic or minimally immunogenic compositions are formulated as a biotherapeutic. In some embodiments, the pharmaceutical compositions are formulated for one or more of intranasal administration, transdermal administration, intraperitoneal administration, intramuscular administration, intranodal administration, intratumoral administration, intraarticular administration, intravenous administration, subcutaneous administration, intravaginal administration, and oral administration.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS), tris (tromethamine), and HEPES. In these cases, the composition should be sterile and should be fluid to the extent that easy syringability exists. It can be stable under the conditions of manufacture and storage, and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sucrose, trehalose, and/or sodium chloride in the composition. In some embodiments, the composition comprises tris and sucrose. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the composition is formulated for one or more of intranasal administration, transdermal administration, intramuscular administration, intranodal administration, intravenous administration, intraperitoneal administration, oral administration, or intra-cranial administration.

Methods of the Disclosure

Administration of any one of the therapeutic compositions described herein, e.g., nucleic acid constructs, recombinant cells, recombinant polypeptides, and/or pharmaceutical compositions, can be used in the treatment of relevant health conditions, such as rabies virus infection. In some embodiments, the nucleic acid constructs, recombinant cells, recombinant polypeptides, and/or pharmaceutical compositions as described herein can be useful for eliciting an immune response in a subject in need thereof. In some embodiments, the nucleic acid constructs, recombinant cells, recombinant polypeptides, and/or pharmaceutical compositions as described herein can be incorporated into therapeutic agents for use in methods of treating a subject who has, who is suspected of having, or who may be at high risk for developing rabies infection. In some embodiments, the subject is a patient under the care of a physician.

Accordingly, in one aspect, provided herein are methods for inducing an immune response in a subject in need thereof, the method includes administering to the subject a composition including: a) a nucleic acid construct of the disclosure; b) a recombinant cell of the disclosure; c) a recombinant polypeptide of the disclosure; and/or d) a pharmaceutical composition of the disclosure.

In some embodiments, the immune response is a neutralizing antibody response. A neutralizing antibody response is an immune response wherein specialized cells of the immune system recognize the presentation of antigen(s), and launch a specific immune response, which prevents infection of target cells from an agent, for example a virus (e.g., rabies virus). Methods of detecting neutralizing antibody responses are known in the art and may include, for example, assays as described in the Examples herein. For example, neutralizing antibody responses can be measured by Rapid Fluorescent Foci Inhibition Test (RFFIT) 14 days after a single dose of the nucleic acid construct disclosed herein. A neutralizing antibody response can also be demonstrated by injecting animals, e.g., mice or non-human primates, with the srRNA construct described herein and testing the ability of serum from the animal to neutralize the ability of the virus to infect cells. In some embodiments, the neutralizing antibody response comprises a neutralizing antibody titer of equal to or greater than 0.5 IU/mL.

In another aspect, provided herein are methods for preventing and/or treating rabies infection in a subject in need thereof, the method includes prophylactically or therapeutically administering to the subject a composition including: a) a nucleic acid construct of the disclosure; b) a recombinant cell of the disclosure; c) a recombinant polypeptide of the disclosure; and/or d) a pharmaceutical composition of any one of the disclosure.

In some embodiments, the disclosed composition is formulated to be compatible with its intended route of administration. For example, the nucleic acid constructs, recombinant cells, recombinant polypeptides, and/or pharmaceutical compositions of the disclosure may be given orally, by inhalation, or through a parenteral route. Examples of parenteral routes of administration include, for example, intramuscular, intraocular, intravenous, intranodal, intradermal, subcutaneous, transdermal (topical), transmucosal, intravaginal, and rectal administration. In some embodiments, the composition is administered intramuscularly. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates, phosphates, tris, sucrose and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

The therapeutic compositions described herein, e.g., nucleic acid constructs, recombinant cells, recombinant polypeptides, and/or pharmaceutical compositions, can be administered one from one or more times per day to one or more times per week; including once every other day. Treatment of a subject with a therapeutically effective amount of the subject nucleic acid constructs, recombinant cells, recombinant polypeptides, and/or pharmaceutical compositions of the disclosure can include a single treatment or, can include a series of treatments. In some embodiments, the compositions are administered at weekly intervals, e.g., 1 to 2, 2 to 3, or 3 to 4 doses given at 1 to 2, 2 to 3, or 3 to 4 week intervals. This may be followed with an additional administration every 1, 2, 3, or 4 months. In some embodiments, 3 doses can be administered intramuscularly at a 3 to 8 week interval, followed by intramuscular administration every 3, 6, 9, or 12 months. This may be followed with an additional administration every 1, 2, 3, or 4 years. With regard to nucleic acid constructs and recombinant polypeptides, the therapeutically effective amount of a nucleic acid construct or recombinant polypeptide of the disclosure (e.g., an effective dosage) depends on the nucleic acid construct or recombinant polypeptide selected.

As discussed supra, a therapeutically effective amount includes an amount of a therapeutic composition that is sufficient to promote a particular effect when administered to a subject, such as one who has, is suspected of having, or is at risk for a health condition, e.g., a rabies infection. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease.

A treatment is considered effective treatment if at least any one or all of the signs or symptoms of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments, the nucleic acid constructs, recombinant cells, recombinant polypeptides, and/or pharmaceutical compositions of the disclosure can be administered to a subject in a composition having a pharmaceutically acceptable carrier and in an amount effective to stimulate an immune response. Generally, a subject can be immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject. In some embodiments of the disclosed methods, the subject is a mammal. In some embodiments, the mammal is a human subject.

As described above, pharmaceutically acceptable carriers suitable for injectable use include sterile aqueous solutions (where water soluble) or dispersions and sterile powders for the extemporaneous preparation of sterile injectable solutions or dispersions. In these cases, the composition must be sterile and must be fluid to the extent that easy syringeability exists. The composition must further be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, etc.), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

Sterile injectable solutions can be prepared by incorporating the nucleic acid constructs, recombinant cells, and/or recombinant polypeptides in the required mount in an appropriate solvent with one or a combination of ingredients enumerated above, as required, followed by filtered sterilization.

When the nucleic acid constructs, recombinant cells, recombinant polypeptides, and/or pharmaceutical compositions are suitably protected, as described above, they may be orally administered, for example, with an inert diluent or an assimilable edible carrier. The nucleic acid constructs, recombinant cells, recombinant polypeptides, and/or pharmaceutical compositions and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like.

Additional Therapies

In some embodiments, a composition according to the present disclosure is administered to the subject individually as a single prophylaxis or therapy (monotherapy) or as a first therapy in combination with at least one additional therapies (e.g., second therapy). In some embodiments, the second therapy is selected from the group consisting of chemotherapy, radiotherapy, immunotherapy, hormonal therapy, toxin therapy, targeted therapy, and surgery. In some embodiments, the second therapy is selected from the group consisting of chemotherapy, radiotherapy, immunotherapy, hormonal therapy, toxin therapy or surgery. In some embodiments, the first therapy and the second therapy are administered concomitantly. In some embodiments, the first therapy is administered at the same time as the second therapy. In some embodiments, the first therapy and the second therapy are administered sequentially. In some embodiments, the first therapy is administered before the second therapy. In some embodiments, the first therapy is administered after the second therapy. In some embodiments, the first therapy is administered before and/or after the second therapy. In some embodiments, the first therapy and the second therapy are administered in rotation. In some embodiments, the first therapy and the second therapy are administered together in a single formulation.

Kits

Also provided herein are various kits for the practice of a method described herein as well as written instructions for making and using the same. In particular, some embodiments of the disclosure provide kits for eliciting an immune response in a subject. Some other embodiments relate to kits for methods of treating cancer in a subject in need thereof. For example, provided herein, in some embodiments, are kits that include one or more of the nucleic acid constructs, recombinant cells, recombinant polypeptides, and/or pharmaceutical compositions as provided and described herein, as well as written instructions for making and using the same.

In some embodiments, the kits of the disclosure further include one or more means useful for the administration of any one of the provided nucleic acid constructs, recombinant cells, recombinant polypeptides, and/or pharmaceutical compositions to a subject. For example, in some embodiments, the kits of the disclosure further include one or more syringes (including pre-filled syringes) and/or catheters (including pre-filled syringes) used to administer any one of the provided nucleic acid constructs, recombinant cells, recombinant polypeptides, and/or pharmaceutical compositions to a subject. In some embodiments, a kit can have one or more additional therapeutic agents that can be administered simultaneously or sequentially with the other kit components for a desired purpose, e.g., for diagnosing, preventing, or treating a condition in a subject in need thereof.

Any of the above-described kits can further include one or more additional reagents, where such additional reagents can be selected from: dilution buffers; reconstitution solutions, wash buffers, control reagents, control expression vectors, negative controls, positive controls, reagents suitable for in vitro production of the provided nucleic acid constructs, recombinant cells, recombinant polypeptides, and/or pharmaceutical compositions of the disclosure.

In some embodiments, the components of a kit can be in separate containers. In some other embodiments, the components of a kit can be combined in a single container. Accordingly, in some embodiments of the disclosure, the kit includes one or more of the nucleic acid constructs, recombinant cells, recombinant polypeptides, and/or pharmaceutical compositions as provided and described herein in one container (e.g., in a sterile glass or plastic vial) and a further therapeutic agent in another container (e.g., in a sterile glass or plastic vial).

In another embodiment, the kit includes a combination of the compositions described herein, including one or more nucleic acid constructs, recombinant cells, and/or recombinant polypeptides of the disclosure in combination with one or more further therapeutic agents formulated together, optionally, in a pharmaceutical composition, in a single, common container.

If the kit includes a pharmaceutical composition for parenteral administration to a subject, the kit can include a device (e.g., an injection device or catheter) for performing such administration. For example, the kit can include one or more hypodermic needles or other injection devices as discussed above containing one or more nucleic acid constructs, recombinant cells, and/or recombinant polypeptides of the disclosure.

In some embodiments, a kit can further include instructions for using the components of the kit to practice the methods disclosed herein. For example, the kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the disclosure may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and intellectual property information.

The instructions for practicing the methods are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the Applicant reserves the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Additional embodiments are disclosed in further detail in the following examples, which are provided by way of illustration and are not in any way intended to limit the scope of this disclosure or the claims.

EXAMPLES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, N.Y.: Cold Spring Harbor Laboratory and Sambrook, J., & Russel, D. W. (2001). *Molecular Cloning: A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual: The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B. V., the disclosures of which are incorporated herein by reference.

Additional embodiments are disclosed in further detail in the following examples, which are provided by way of illustration and are not in any way intended to limit the scope of this disclosure or the claims.

Example 1

Construction of Alphavirus Vectors

This Example describes the experiments performed to construct base alphavirus vectors (e.g., without a heterologous gene of interest) that were subsequently used for construction of vectors that express a gene of interest (e.g., RABV-G).

EEEV Base Vector

The base EEEV vector (i.e. without a heterologous gene of interest) was constructed as follows: The base EEEV vector was synthesized de novo in four ~4 kb parts (Twist Bioscience) from a reference sequence (Genbank EF151502) with several modifications. Silent mutations G301A, A3550C, G4516A, G5725A, G7399A mutations were incorporated to eliminate restriction enzyme cut sites. A unique restriction enzyme cut site (SpeI, 5'-A'CTAG,T-3') was incorporated in place of the coding sequence of the native EEEV structural genes (where the 5' A matches the location of the structural polyprotein ATG start codon, and the 3' T matches the location of the structural polyprotein stop codon TAA). A 5' adaptor sequence (5'-CTGGAGACGTGGAGGAGAACCCTGGACCT-3'; SEQ ID NO: 2) was inserted upstream of the SpeI site, and a 3' adaptor sequence (5'-GACCGCTACGCCCCAATGACCCGACCAGC-3'; SEQ ID NO: 3) was inserted downstream of the SpeI site for subsequent Gibson Assembly® procedures (Gibson et al., *Nat. Methods* 6, 343-345, 2009). A bacteriophage T7 RNA polymerase promoter (5'-TAATACGACTCACTATAG-3'; SEQ ID NO: 4) was included upstream of the EEEV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 5) followed by a unique restriction enzyme cut site (NotI, 5'-GC'GGCC,GC-3'). The parts were combined in a five-piece Gibson Assembly® reaction: a linearized pYL backbone and the four synthesized fragments to result in the EEEV base vector.

CHIKV Base Vectors

The base CHIKV S27 vector was synthesized de novo in four ~4 kb parts (Twist Bioscience, Thermo Fisher GeneArt) from a reference sequence (Genbank AF369024) with a silent A5366G mutation, and with a unique restriction enzyme cut site (SpeI, 5'-A'CTAG,T-3') in place of the coding sequence of the CHIKV structural genes (where the 5' A matches the location of the structural polyprotein's ATG start codon, and the 3' T matches the location of the structural polyprotein's stop codon TAA). A 5' adaptor sequence (5'-CTGGAGACGTGGAGGAGAACCCTGGACCT-3'; SEQ ID NO: 2) was inserted upstream of the SpeI site, and a 3' adaptor sequence (5'-GACCGCTACGCCCCAATGACCCGACCAGC-3'; SEQ ID NO: 3) was inserted downstream of the SpeI site for subsequent Gibson Assembly® procedures. A bacteriophage T7 RNA polymerase promoter (5'-TAATACGACTCACTATAG-3'; SEQ ID NO: 4) was included upstream of the CHIKV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 5) followed by a unique restriction enzyme cut site (NotI, 5'-GC'GGCC,GC-3'). The parts were combined in a five-piece Gibson Assembly® reaction a linearized pYL backbone and the four synthesized fragments to result in the CHIKV S27 base vector.

The CHIKV DRDE base vector was similarly constructed from a reference sequence (Genbank EF210157), except the S27 3' UTR was used in place of the DRDE 3' UTR.

SINV Base Vectors

The base SINV Girdwood vector was synthesized de novo in four ~4 kb parts (Twist Bioscience, Thermo Fisher GeneArt) from a Girdwood strain reference sequence (Genbank MF459683) with a unique restriction enzyme cut site (SpeI, 5'-A'CTAG,T-3') in place of the coding sequence of the SINV structural genes (where the 5' A is the next nucleotide after a P2A sequence following nucleotide 93 of the structural polyprotein gene, and the 3' T matches the location of the structural polyprotein's stop codon TGA). A bacteriophage T7 RNA polymerase promoter (5'-TAATACGACTCACTATAG-3'; SEQ ID NO: 4) was included upstream of the SINV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 5) followed by a unique restriction enzyme cut site (NotI, 5'-GC'GGCC,GC-3'). The parts were combined in a five-piece Gibson Assembly® reaction (e.g., a linearized pYL backbone and the four synthesized fragments) to result in the SINV Girdwood base vector.

The base SINV AR86 vector was similarly constructed from a reference sequence (Genbank U38305), except the nsP2 coding sequence was derived from the Girdwood reference sequence.

VEE Base Vector

The base VEE vector was synthesized de novo in four ~4 kb parts (Twist Bioscience, Thermo Fisher GeneArt) from a TC-83 strain reference sequence (Genbank L01443) with a silent A2087G mutation, and a unique restriction enzyme cut site (SpeI, 5'-A'CTAG,T-3') in place of the coding sequence of the VEE structural genes (where the 5' A is the next nucleotide after a P2A sequence following nucleotide 93 of the structural polyprotein gene, and the 3' T matches the location of the structural polyprotein's stop codon TGA). A 5' adaptor sequence (5'-CTGGAGACGTGGAGGAGAACCCTGGACCT-3'; SEQ ID NO: 2) was inserted upstream of the SpeI site, and a 3' adaptor sequence (5'-GACCGCTACGCCCCAATGACCCGACCAGC-3'; SEQ ID NO: 3) was inserted downstream of the SpeI site for subsequent Gibson Assembly® procedures. A bacteriophage T7 RNA polymerase promoter (5'-TAATACGACTCACTATAG-3'; SEQ ID NO: 4) was included upstream of the VEE genome sequence, and downstream contained a poly (A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 5) followed by a unique restriction enzyme cut site (NotI, 5'-GC'GGCC,GC-3'). The parts were combined in a five-piece Gibson Assembly® reaction (e.g., a linearized pYL backbone and the four synthesized fragments) to result in the VEE base vector.

The RABV-G transgene was synthesized (IDT) with flanks homologous to the 5' and 3' adaptor sequences, and inserted into the SpeI-linearized base vectors by Gibson Assembly® to result in the final vectors.

Example 2

In Vitro Evaluation of Modified Alphaviral Vectors

This Example describes the results of in vitro experiments performed to evaluate RNA replication and RABV-G expression levels of the synthetic alphaviral srRNA constructs described in Example 1 above, and to investigate any differential behavior thereof (e.g., RNA replication and protein expression).

In vitro transcription: RNA was prepared by in vitro transcription from a SapI-linearized plasmid template with bacteriophage T7 polymerase with either a 5' ARCA cap (HiScribe™ T7 ARCA mRNA Kit, NEB) or by uncapped transcription (HiScribe™ T7 High Yield RNA Synthesis Kit, NEB) followed by addition of a 5' cap 1 (Vaccinia Capping System, mRNA Cap 2'-O-Methyltransferase, NEB). RNA was then purified using phenol/chloroform extraction, or column purification (Monarch® RNA Cleanup Kit, NEB). RNA concentration was determined by absorbance at 260 nm (Nanodrop, Thermo Fisher Scientific).

RNA replication: RNA was transformed by electroporation into BHK-21 or Vero cells (e.g., 4D-Nucleofector™, Lonza). At 15-22 hours following transformation, the cells were fixed and permeabilized (eBioscience™ Foxp3/Transcription Factor Staining Buffer Set, Invitrogen) and stained using a PE-conjugated anti-dsRNA mouse monoclonal antibody (J2, Scions) to quantify the frequency of dsRNA+ cells and the mean fluorescence intensity (MFI) of dsRNA in individual cells by fluorescence flow cytometry. Results are shown in FIG. 1.

Figure 2:
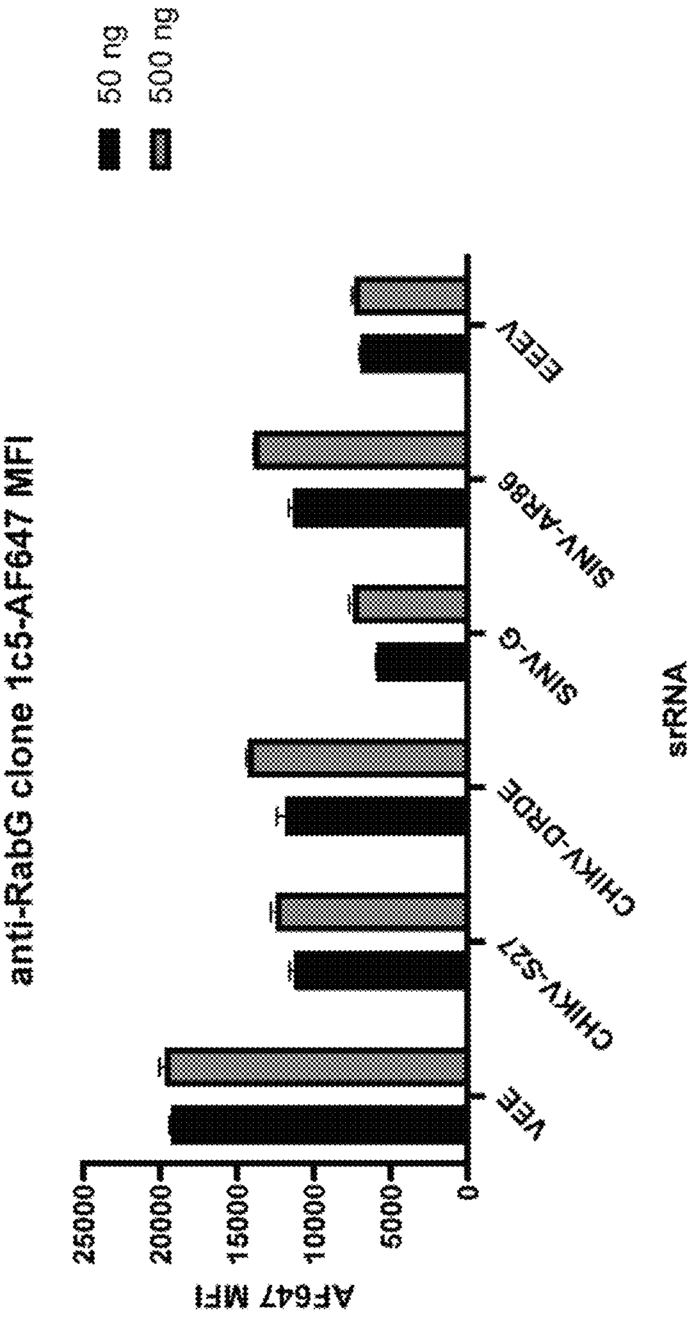
FIG. 2 is a bar chart that shows relative expression of rabies virus glycoprotein (RABV-G) from different srRNA vectors. srRNA encoding the RABV-G gene was transfected at 50 or 500 ng into 7.7E5 BHK-21 cells by nucleofection and 15 hours later cells were collected and stained with an AF647-conjugated anti-RabG antibody (1c5). The mean fluorescence intensity (MFI) of transfected cells was determined by flow cytometry (FC).

Protein expression: RNA was transformed by electroporation into BHK-21 or Vero cells (e.g., 4D-Nucleofector™, Lonza). At 15-22 hours following transformation, the cells were fixed and permeabilized (eBioscience™ Foxp3/Transcription Factor Staining Buffer Set, Invitrogen) and stained using an AF647-conjugated anti-RABV-G antibody (1c5). The mean fluorescence intensity (MFI) of AF647 was used as the readout of RABV-G expression. Results are shown in FIG. 2.

Example 3

In Vivo Evaluation of Modified Alphaviral Vectors

This Example describes the results of in vivo experiments performed to evaluate the srRNA constructs described herein.

In these experiments, synthetic srRNA constructs derived from various alphavirus strains were designed and subsequently evaluated.

Mice and injections. BALB/c mice were purchased from Charles River Labs, Envigo, or Jackson Laboratories. On day of dosing, 0.15 or 1.5 μg of material was injected intramuscularly either into one or split into both quadricep muscles. Vectors were LNP-formulated. Animals were monitored for body weight and other general observations throughout the course of the study. For immunogenicity studies, animals were dosed on Day 0 only or Day 0 and Day 21.

LNP formulation. srRNA was formulated in lipid nanoparticles using a microfluidics mixer and analyzed for particle size, polydispersity using dynamic light scattering and encapsulation efficiency. Lipids were suspended in ethanol. RNA was suspended in 250 mM NaOAc pH 4.0 at a concentration of 82 ug/ml, and was mixed at a flow rate of 3:1 (aqueous:organic).

Figure 3:
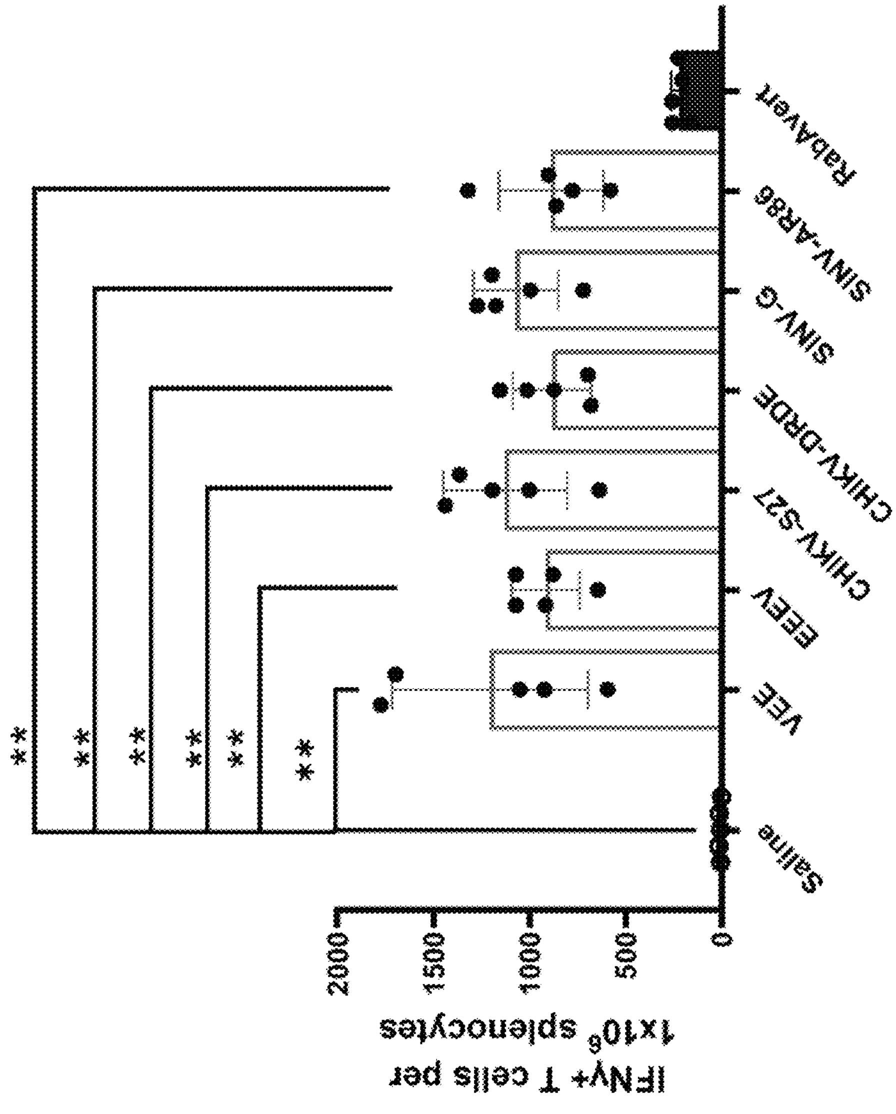
FIG. 3 shows srRNA-based rabies vaccines can generate T cell responses in vivo (ELISpot). T cell responses as measured by IFNγ ELISpot 14 days after a single dose of srRNA-RABV-G (0.15 ug) are shown.

ELISpot. To measure the magnitude of RABV-G-specific T cell responses, IFNγ ELISpot analysis was performed using Mouse IFNγ ELISpot PLUS Kit (HRP) (MabTech) as per manufacturer's instructions. Results of mouse IFNγ detecting ELISpot assay as measured by spot-forming units corresponding to responder splenic T cells 14 days after intramuscular injection of srRNA encoding RABV-G is shown in FIG. 3. The total T cell responses (plotted as counted spot-forming units per million of cells) are shown the y-axis.

Figure 4:
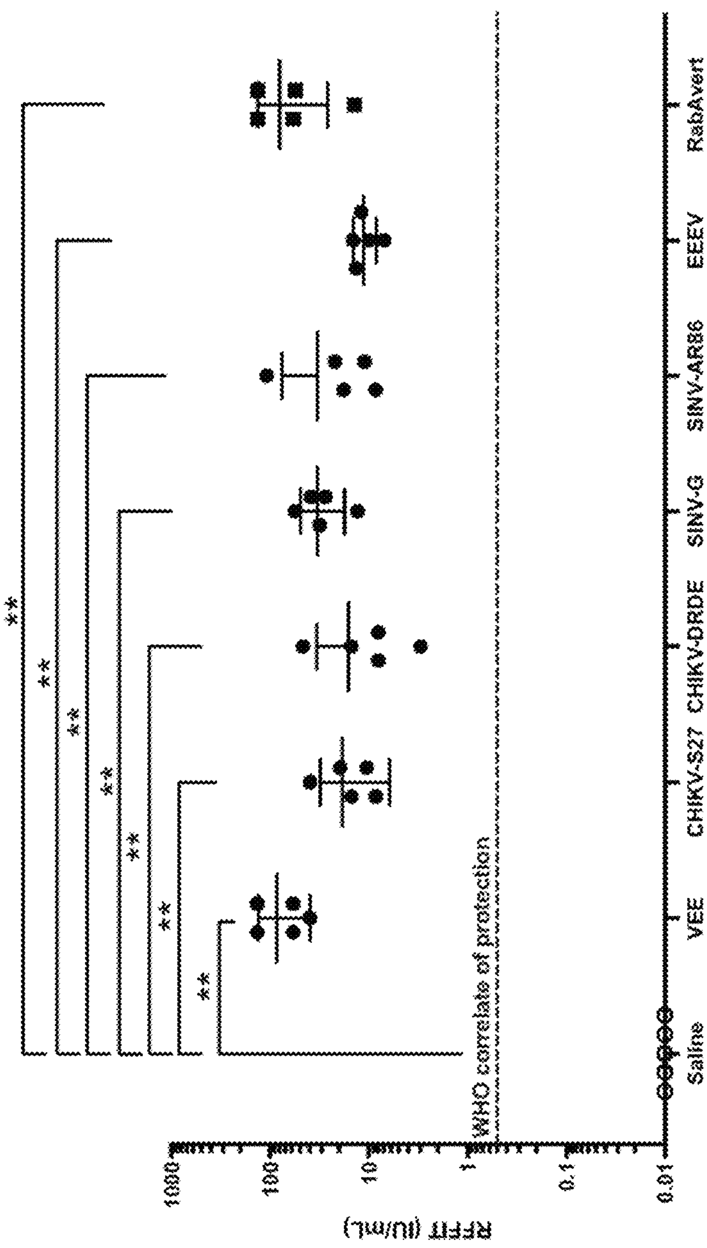
FIG. 4 shows srRNA-based rabies vaccines can generate protective antibody responses in vivo. Neutralizing antibody responses as measured by Rapid Fluorescent Foci Inhibition Test (RFFIT) 14 days after a single dose of srRNA-RABV-G (0.15 ug) are shown. Neutralizing antibody titers of 0.5 IU/ml, considered to be protective, are depicted by the blue line. Statistics are shown (**<0.01; *<0.05).

Neutralizing Antibody Response by Rapid Fluorescent Foci Inhibition Test: To measure neutralizing antibody titers generated by the vaccines, sera was obtained from mice 14 days after intramuscular administration, diluted, mixed, and incubated with a standard amount of rabies virus in multi-chambered slides. After a short incubation, cells that are susceptible to rabies virus infection and replication are added to the serum-virus mixture and incubated overnight (~16-24 hrs) to allow for non-neutralized virus to infect the cells and replicate. The cells are then fixed and stained for rabies virus production using a fluorescent microscope. Up to a total of 20 microscopic fields are read for each serum sample and compared against a slide with a reference control serum-virus mixture. Infected cells are counted for each serum dilution and used to determine the neutralization titer. The final RFFIT result is a calculation of the counts multiplied by the dilution factor of the serum. The results of the RFFIT can be expressed as a serum titer or in International Units (IU) of antibody per milliliter of serum, the latter was done by comparing neutralizing activity of the test serum is compared to that of a reference serum with a known IU concentration (FIG. 4).

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A nucleic acid construct comprising a nucleic acid sequence encoding a modified alphavirus genome or self-replicating RNA (srRNA), wherein the modified alphavirus genome or srRNA comprises no nucleic acid sequence encoding viral structural proteins required for viral particle formation, wherein the nucleic acid sequence encoding the viral structural proteins of the modified alphavirus genome or srRNA has been replaced by a coding sequence for a polypeptide construct comprising an envelope glycoprotein G of a rabies virus (RABV-G), a variant thereof, or an antigenic determinant of either thereof, and wherein the nucleic acid construct comprises the nucleic acid sequence of SEQ ID NO: 2 and SEQ ID NO: 3.

2. The nucleic acid construct of claim 1, wherein the antigenic determinant resides within the N-terminal half of the RABV-G.

3. The nucleic acid construct of claim 1, wherein the antigenic determinant resides within the C-terminal half of the RABV-G.

4. The nucleic acid construct of claim 1, wherein the antigenic determinant comprises antigenic site I, antigenic site II, antigenic site III, antigenic site IV, antigenic site minor A of the RABV-G, or a combination of any thereof.

5. The nucleic acid construct of claim 1, wherein the envelope glycoprotein G is of a virulent rabies virus strain or an avirulent rabies virus strain.

6. The nucleic acid construct of claim 1, wherein the envelope glycoprotein G is of a rabies virus strain selected from a Flury LEP strain, a Flury LEP-C strain, a Flury HEP strain, a 1088 strain, a AT6 strain, a CQ92 strain, a CVS-11 strain, a CVS-26 strain, a CVS-26(G-N204S) strain, a CYN1009D strain, a CYN1026D strain, a CYN1029D strain, a CYN1138D strain, a CYN1140D strain, a CYN1141D strain, a CYN1242H strain, a CYN1243D strain, a CYN1244D strain, a CYN1245D strain, a CYN1247D strain, a CYN1249D strain, a CYN1250D strain, a CYN1251D strain, a CYN1252D strain, a CYN1253D strain, a CYN1255D strain, a CYN1256D strain, a CYN1257D strain, a CYN1259D strain, a CYN1260D strain, a CYN1261D strain, a GX4 strain, a H-08-1320 strain, a H-1413-09 strain, a IP 1586/10 strain, a IP 2990/13 strain, a IP 2991/13 strain, a IP 2992/13 strain, a IP 3176/09 strain, a IP 4005/12 strain, a IP 412/10 strain, a IP 542/10 strain, a IP 7941/09 strain, a J strain, a JX-08-47 strain, a JX08-48 strain, a Kyoto strain, a Kyoto(G-S204N) strain, a N·HL strain, a RC·HL strain, a rHEP5.0-CVSG strain, a RRV ON-99-2 strain, a SAD-B19 strain, a SH06 strain, a SHRBV-18 strain, a SNK-CTN strain, a SRV9 strain, a Street Alabama Dufferin (HCP-SAD) strain, a VRC-RZ2 strain, a ZJ-LA strain, and a ZJ-QZ strain.

7. The nucleic acid construct of claim 6, wherein the envelope glycoprotein G is of a Flury LEP strain.

8. The nucleic acid construct of claim 1, wherein the polypeptide construct comprises a molecular alteration that stabilizes the RABV-G, variant thereof, or antigenic determinant of either thereof.

9. The nucleic acid construct of claim 1, wherein the nucleic acid sequence encoding the polypeptide construct is operably linked to a promoter sequence.

10. The nucleic acid construct of claim 9, wherein the promoter sequence is a 26S subgenomic (sg) promoter.

11. The nucleic acid construct of claim 1, wherein the modified alphavirus genome or srRNA is of an alphavirus belonging to the VEEV/EEEV group, or the SFV group, or the SINV group.

12. The nucleic acid of claim 11, wherein the alphavirus is Venezuelan equine encephalitis virus (VEEV), Eastern equine encephalitis virus (EEEV), Chikungunya virus (CHIKV), Western equine encephalitis virus (WEEV), or Sindbis virus (SINV).

13. The nucleic acid construct of claim 1, wherein the nucleic acid sequence has at least 80%, at least 85%, at least 90%, at least 95%, at least 96%, at least 97%, at least 98%, at least 99%, or 100% sequence identity to a nucleic acid sequence selected from the group consisting of SEQ ID NOS:6-11.

14. An isolated recombinant cell comprising a nucleic acid construct according to claim 1.

15. The recombinant cell of claim 14, wherein the recombinant cell is a mammalian cell or an insect cell.

16. A pharmaceutical composition comprising a pharmaceutically acceptable excipient and a nucleic acid construct of claim 1.

17. The pharmaceutical composition of claim 16, wherein the composition is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof.

18. The pharmaceutical composition of claim 17, wherein the LNP delivery system comprises a cationic lipid, an ionizable cationic lipid, an anionic lipid, or a neutral lipid.

19. The pharmaceutical composition of claim 17, wherein the lipid is present in mass ratio of lipid to RNA from about 100:1 to about 4:1.

20. The pharmaceutical composition of claim 17, wherein the lipid-based nanoparticles have an average diameter of about 25 nm to about 1000 nm.

21. The pharmaceutical composition of claim 17, wherein the composition is formulated as an immunogenic composition or an adjuvant.

22. The pharmaceutical composition of claim 16, wherein the composition is formulated for intramuscular administration.

23. A method for inducing an immune response in a subject in need thereof, the method comprising administering to the subject a composition comprising a nucleic acid construct of claim 1.

24. The method of claim 23, wherein the immune response is a neutralizing antibody response.

25. The method of claim 24, wherein the neutralizing antibody response comprises a neutralizing antibody titer of greater than 0.5 IU/mL.

26. The method of claim 23, wherein the subject is having or suspected of having a rabies infection.

* * * * *

SEQUENCE LISTING

```
<160> NUMBER OF SEQ ID NOS: 11

<210> SEQ ID NO 1
<211> LENGTH: 524
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Unmodified RABV-G

<400> SEQUENCE: 1

Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
        195                 200                 205

Asp Ile Phe Thr Asn Ser Arg Gly Lys Arg Ala Ser Lys Gly Gly Lys
    210                 215                 220

Thr Cys Gly Phe Val Asp Glu Arg Gly Leu Tyr Lys Ser Leu Lys Gly
```

-continued

```
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Gly Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Asp Gly Asp Glu Val Glu
            420                 425                 430

Asp Phe Val Glu Val His Leu Pro Asp Val His Glu Gln Val Ser Gly
        435                 440                 445

Val Glu Leu Gly Leu Pro Asn Trp Gly Lys Tyr Val Leu Met Ile Ala
    450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Ser Leu Gly Glu Thr
                485                 490                 495

Gly Arg Asn Val Ser Val Thr Ser Gln Ser Gly Lys Val Ile Ser Ser
            500                 505                 510

Trp Glu Ser Tyr Lys Ser Gly Gly Glu Thr Arg Leu
        515                 520
```

<210> SEQ ID NO 2
<211> LENGTH: 29
<212> TYPE: DNA
<213> ORGANISM: Artificial Sequence
<220> FEATURE:
<223> OTHER INFORMATION: Synthetic construct

<400> SEQUENCE: 2
ctggagacgt ggaggagaac cctggacct 29

<210> SEQ ID NO 3
<211> LENGTH: 29
<212> TYPE: DNA
<213> ORGANISM: Artificial Sequence
<220> FEATURE:
<223> OTHER INFORMATION: Synthetic construct

<400> SEQUENCE: 3
gaccgctacg ccccaatgac ccgaccagc 29

<210> SEQ ID NO 4
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: T7 RNA polymerase promoter

<400> SEQUENCE: 4
taatacgact cactatag 18

<210> SEQ ID NO 5
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: T7 terminator sequence

<400> SEQUENCE: 5
aacccctctc taaacggagg ggtttttt 29

<210> SEQ ID NO 6
<211> LENGTH: 9321
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: VEEV RABV-G srRNA construct

<400> SEQUENCE: 6
gauaggcggc gcaugagaga agcccagacc aauuaccuac ccaaaaugga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
agugcgcccg cccgcagaau guauucuaag cacaaguauc auuguaucug uccgaugaga 300
ugugcggaag auccggacag auuguauaag uaugcaacua agcugaagaa aaacuguaag 360
gaaauaacug auaaggaauu ggacaagaaa augaaggagc ucgccgccgu caugagcgac 420
ccugaccugg aaacugagac uaugugccuc cacgacgacg agucgugucg cuacgaaggg 480
caagucgcug uuuaccagga uguauacgcg guugacggac cgacaagucu cuaucaccaa 540
gccaauaagg gaguuagagu cgccuacugg auaggcuuug acaccacccc uuuuauguuu 600
aagaacuugg cuggagcaua uccaucauac ucuaccaacu gggccgacga aaccguguua 660
acggcucgua acauaggccu augcagcucu gacguuaugg agcggucacg uagagggaug 720
uccauucuua gaaagaagua uuugaaacca uccaacaaug uucuauucuc uguuggcucg 780
accaucuacc acgagaagag ggacuuacug aggagcuggc accugccguc uguauuucac 840
uuacguggca agcaaaauua cacaugucgg ugugagacua uaguuaguug cgacggguac 900
gucguuaaaa gaauagcuau caguccaggc cuguauggga agccuucagg cuaugcugcu 960
acgaugcacc gcgagggauu cuugugcugc aaagugacag acacauugaa cggggagagg 1020
gucucuuuuc ccgugugcac guaugugcca gcuacauugu gugaccaaau gacuggcaua 1080

-continued

```
cuggcaacag augucagugc ggacgacgcg caaaaacugc ugguugggcu caaccagcgu   1140
auagucguca acggucgcac ccagagaaac accaauacca ugaaaaauua ccuuuugccc   1200
guaguggccc aggcauuugc uaggugggca aaggaauaua aggaagauca agaagaugaa   1260
aggccacuag gacuacgaga uagacaguua gucaugggu guuguugggc uuuuagaagg   1320
cacaagauaa caucuauuua uaagcgcccg gauacccaaa ccaucaucaa agugaacagc   1380
gauuuccacu cauucgugcu gcccaggaua ggcaguaaca cauuggagau cgggcugaga   1440
acaagaauca ggaaaauguu agaggagcac aaggagccgu caccucucau uaccgccgag   1500
gacguacaag aagcuaagug cgcagccgau gaggcuaagg aggugcguga agccgaggag   1560
uugcgcgcag cucuaccacc uuuggcagcu gauguugagg agcccacucu ggaagccgau   1620
gucgacuuga uguuacaaga ggcuggggcc ggcucagugg agacaccucg uggcuugaua   1680
aagguuacca gcuacgaugg cgaggacaag aucggcucuu acgcugugcu uucuccgcag   1740
gcuguacuca agagugaaaa auuaucuugc auccacccuc ucgcugaaca agucauagug   1800
auaacacacu cuggccgaaa agggcguuau gccguggaac cauaccaugg uaaaguagug   1860
gugccagagg gacaugcaau acccguccag gacuuucaag cucugaguga aagugccacc   1920
auuguguaca acgaacguga guucguaaac agguaccugc accauauugc cacacaugga   1980
ggagcgcuga acacugauga agaauauuac aaaacuguca agcccagcga gcacgacggc   2040
gaauaccugu acgacaucga caggaaacag ugcgucaaga aagaacuggu cacugggcua   2100
gggcucacag gcgagcuggu ggauccuccc uuccaugaau ucgccuacga gagucugaga   2160
acacgaccag ccgcuccuua ccaaguacca accauagggg uguauggcgu gccaggauca   2220
ggcaagucug gcaucauuaa aagcgcaguc accaaaaaag aucuagugu gagcgccaag   2280
aaagaaaacu gugcagaaau uauaagggac gucaagaaaa ugaaagggcu ggacgucaau   2340
gccagaacug uggacucagu gcucuugaau ggaugcaaac accccguaga gacccuguau   2400
auugacgaag cuuuugcuug ucaugcaggu acucucagag cgcucauagc cauuauaaga   2460
ccuaaaaagg cagugcucug cggggauccc aaacagugcg guuuuuuaa caugaugugc   2520
cugaaagugc auuuuaacca cgagauuugc acacaagucu uccacaaaag caucucucgc   2580
cguugcacua aaucugugac uucggucguc ucaaccuugu uuuacgacaa aaaaaugaga   2640
acgacgaauc cgaaagagac uaagauugug auugacacua ccggcaguac caaaccuaag   2700
caggacgauc ucauucucac uuguuucaga gggugggguga agcaguugca aauagauuac   2760
aaaggcaacg aaauaaugac ggcagcugcc ucucaagggc ugacccguaa agguguguau   2820
gccguucggu acaaggugaa ugaaaauccu cuguacgcac ccaccucuga acaugugaac   2880
guccuacuga cccgcacgga ggaccgcauc guguggaaaa cacuagccgg cgacccaugg   2940
auaaaaacac ugacugccaa guacccuggg aauuucacug ccacgauaga ggaguggcaa   3000
gcagagcaug augccaucau gaggcacauc uuggagagac cggacccuac cgacgucuuc   3060
cagaauaagg caaacgugug uugggccaag gcuuuagugc cggugcugaa gaccgcuggc   3120
auagacauga ccacugaaca auggaacacu guggauuauu uugaaacgga caaagcucac   3180
ucagcagaga uaguauugaa ccaacuaugc gugagguucu uuggacucga ucuggacucc   3240
ggucuauuuu cugcacccac uguuccguua uccauuagga auaaucacug ggauaacucc   3300
ccgucgccua acauguacgg gcugaauaaa gaaguggucc gucagcucuc ucgcagguac   3360
ccacaacugc cucgggcagu ugccacugga agagucuaug acaugaacac ugguacacug   3420
```

-continued

```
cgcaauuaug auccgcgcau aaaccuagua ccuguaaaca gaagacugcc ucaugcuuua   3480
guccuccacc auaaugaaca cccacagagu gacuuuucuu cauucgucag caaauugaag   3540
ggcagaacug uccugguggu cggggaaaag uuguccgucc caggcaaaau gguugacugg   3600
uugucagacc ggccugaggc uaccuucaga gcucggcugg auuuaggcau cccaggugau   3660
gugcccaaau augacauaau auuuguuaau gugaggaccc cauauaaaua ccaucacuau   3720
cagcagugug aagaccaugc cauuaagcuu agcauguuga ccaagaaagc uugucugcau   3780
cugaaucccg gcggaaccug ugucagcaua gguuaugguu acgcugacag ggccagcgaa   3840
agcaucauug gugcuauagc gcggcaguuc aaguuuuccc ggguaugcaa accgaaaucc   3900
ucacuugaag agacggaagu ucuguuugua uucauugggu acgaucgcaa ggcccguacg   3960
cacaauccuu acaagcuuuc aucaaccuug accaacauuu auacagguuc cagacuccac   4020
gaagccggau gugcacccuc auaucaugug gugcgagggg auauugccac ggccaccgaa   4080
ggagugauua uaaaugcugc uaacagcaaa ggacaaccug gcggaggggu gugcggagcg   4140
cuguauaaga aauucccgga aagcuucgau uuacagccga ucgaaguagg aaaagcgcga   4200
cuggucaaag gugcagcuaa acauaucauu caugccguag gaccaaacuu caacaaaguu   4260
ucggagguug aaggugacaa acaguuggca gaggcuuaug aguccaucgc uaagauuguc   4320
aacgauaaca auuacaaguc aguagcgauu ccacuguugu ccaccggcau cuuuuccggg   4380
aacaaagauc gacuaaccca aucauugaac cauuugcuga cagcuuuaga caccacugau   4440
gcagauguag ccauauacug cagggacaag aaaugggaaa ugacucucaa ggaagcagug   4500
gcuaggagag aagcagugga ggagauaugc auauccgacg acucuucagu gacagaaccu   4560
gaugcagagc uggugagggu gcauccgaag aguucuuugg cuggaaggaa gggcuacagc   4620
acaagcgaug gcaaaacuuu cucauauuug gaagggacca aguuucacca ggcggccaag   4680
gauauagcag aaauuaaugc caugugggcc guugcaacgg aggccaauga gcagguaugc   4740
auguauaucc ucggagaaag caugagcagu auuaggucga aaugccccgu cgaagagucg   4800
gaagccucca caccaccuag cacgcugccu ugcuugugca uccaugccau gacuccagaa   4860
agaguacagc gccuaaaagc cucacgucca gaacaaauua cugugugcuc auccuuucca   4920
uugccgaagu auagaaucac uggugugcag aagauccaau gcucccagcc uauauuguuc   4980
ucaccgaaag ugccugcgua uauucaucca aggaaguauc ucguggaaac accaccggua   5040
gacgagacuc cggagccauc ggcagagaac caauccacag aggggacacc ugaacaacca   5100
ccacuuauaa ccgaggauga gaccaggacu agaacgccug agccgaucau caucgaagag   5160
gaagaagagg auagcauaag uuugcuguca gauggcccga cccaccaggu gcugcaaguc   5220
gaggcagaca uucacgggcc gcccucugua ucuagcucau ccugguccau uccucaugca   5280
uccgacuuug auguggacag uuuauccaua cuugacaccc uggagggagc uagcgugacc   5340
agcggggcaa cgucagccga gacuaacucu uacuucgcaa agaguaugga guuucuggcg   5400
cgaccggugc cugcgccucg aacaguauuc aggaacccuc cacaucccgc uccgcgcaca   5460
agaacaccgu cacuugcacc cagcagggcc ugcucgagaa ccagccuagu uuccaccccg   5520
ccaggcguga auagggugau cacuagagag gagcucgagg cgcuuacccc gucacgcacu   5580
ccuagcaggu cggucucgag aaccagccug gucuccaacc cgccaggcgu aaauagggug   5640
auuacaagag aggaguuuga ggcguucgua gcacaacaac aaugacgguu ugaugcgggu   5700
gcauacaucu uuuccuccga caccggucaa gggcauuuac aacaaaaauc aguaaggcaa   5760
acggugcuau ccgaaguggu guuggagagg accgaauugg agauuucgua ugccccgcgc   5820
```

cucgaccaag aaaaagaaga auuacuacgc aagaaauuac aguuaaaucc cacaccugcu 5880
aacagaagca gauaccaguc caggaaggug gagaacauga aagccauaac agcuagacgu 5940
auucugcaag gccuagggca uuauuugaag gcagaaggaa aaguggagug cuaccgaacc 6000
cugcauccug uuccuuugua uucaucuagu gugaaccgug ccuuuucaag ccccaagguc 6060
gcaguggaag ccuguaacgc cauguugaaa gagaacuuuc cgacuguggc uucuuacugu 6120
auuauuccag aguacgaugc cuauuuggac augguugacg gagcuucaug cugcuuagac 6180
acugccaguu uuugcccugc aaagcugcgc agcuuuccaa agaaacacuc cuauuuggaa 6240
cccacaauac gaucggcagu gccuucagcg auccagaaca cgcuccagaa cguccuggca 6300
gcugccacaa aaagaaauug caaugucacg caaaugagag aauugcccgu auuggauucg 6360
gcggccuuua auguggaaug cuucaagaaa uaugcgugua auaaugaaua uugggaaacg 6420
uuuaaagaaa accccaucag gcuuacugaa gaaaacgugg uaaauuacau uaccaaauua 6480
aaaggaccaa aagcugcugc ucuuuuugcg aagacacaua auuugaauau guugcaggac 6540
auaccaaugg acagguuugu aauggacuua aagagagacg ugaaagugac uccaggaaca 6600
aaacauacug aagaacggcc caagguacag gugauccagg cugccgaucc gcuagcaaca 6660
gcguaucugu gcggaaucca ccgagagcug guuaggagau uaaaugcggu ccugcuuccg 6720
aacauucaua cacuguuuga uaugucggcu gaagacuuug acgcuauuau agccgagcac 6780
uuccagccug ggauuguguu ucuggaaacu gacaucgcgu cguuugauaa aagugaggac 6840
gacgccaugg cucugaccgc guuaaugauu cuggaagacu uaggugugga cgcagagcug 6900
uugacgcuga uugaggcggc uuucggcgaa auuucaucaa uacauuugcc cacuaaaacu 6960
aaauuuaaau ucggagccau gaugaaaucu ggaauguucc ucacacuguu ugugaacaca 7020
gucauuaaca uuguaaucgc aagcagagug uugagagaac ggcuaaccgg aucaccaugu 7080
gcagcauuca uuggagauga caauaucgug aaaggaguca aaucggacaa auuaauggca 7140
gacaggugcg ccaccugguu gaauauggaa gucaagauua uagaugcugu gguggggcgag 7200
aaagcgccuu auuucugugg aggguuuauu uugugugacu ccgugaccgg cacagcgugc 7260
cguguggcag acccccuaaa aaggcuguuu aagcuuggca aaccucuggc agcagacgau 7320
gaacaugaug augacaggag aagggcauug caugaagagu caacacgcug gaaccgagug 7380
gguauucuuu cagagcugug caaggcagua gaaucaaggu augaaaccgu aggaacuucc 7440
aucauaguua uggccaugac uacucuagcu agcaguguua aaucauucag cuaccugaga 7500
ggggccccua uaacucucua cggcuaaccu gaauggacua cgacauaguc uaguccgcca 7560
agaucuggag acguggagga gaacccugga ccuauggugc cucaggugcu gcuguuugug 7620
ccucugcugg gcuucagccu gugcuucggc aaguucccca ucuacacaau ccccgacaag 7680
cucggcccuu ggagccccau cgauauccac caccugagcu gccccaacaa ccugguggug 7740
gaagaugagg gcugcaccaa ccugagcgag uucagcuaca uggaacugaa agugggcuac 7800
aucagcgcca ucaaagugaa cggcuucacc uguaccggcg uggucacaga ggccgagaca 7860
uacaccaacu ucgugggcua cgugaccacc accuucaagc ggaagcacuu cagacccaca 7920
ccugacgccu guagagccgc cuacaacugg aaaauggccg gcgaucccag auacgaggaa 7980
agccugcaca accccuaucc ugacuaccac uggcugcgga ccgugaaaac caccaaagag 8040
agccugguca ucaucagccc cagcgugacc gaccuggauc cuuacgauaa gagccugcac 8100
ucccgggugu ucccuggcgg aaauugcucu ggcaucaccg uguccagcac cuacugcagc 8160
accaaccacg acuacaccau cuggaugccc gagaaccuga gacugggcac cagcugcgac 8220
aucuucacca acagcagagg aaagcgggcc agcaaaggcg gcaagaccug uggcuuugug 8280
gacgagagag gccuguacaa gucucugaag ggcgccugca agcugaagcu gugcggaguu 8340
cugggacuga gacugaugga uggcaccugg gucgccaugc agaccagcga cgagacaaag 8400 uggugugccuc cuggccagcu ggucaaccug cacgacuuua gauccgacga gaucgagcau 8460
cugguggucg aggaacuggu caagaaacgg gaagagugcc uggacgcccu ggaauccauc 8520
augaccacca agagcguguc cuuccggcgg cugucucacc ugagaaaacu ggugccuggc 8580
uuuggcaagg ccuauaccau cuucaacaag acccugaugg aagccgacgc ucacuacaag 8640
ucugugcgga ccuggaacga gaucaucccc agcaagggcu gccugagagu uggcggaaga 8700
ugucacccuc acgugaacgg cguguucuuc aacggcauca uccugggcuc ugacggccac 8760
gugcugaucc cugaaaugca gucuagccug cuccagcagc auauggaacu gcuggaaagc 8820
agcgugaucc cucugaugca cccucuggcc gauccuagca ccguguucaa ggauggcgac 8880
gaggucgagg acuucgugga agugcaucug cccgacgugc acgagcaagu gucuggcguu 8940
gaacugggcc ugccuaacug gggcaaauau gugcugauga ucgcuggggc ccugaucgcc 9000
cugaugcuga ucaucuuccu gaugaccugc ugucggagag ugaacagacc cgagagcaca 9060
cagagcagcc ugggagagac aggcagaaac guguccguga caagccagag cggcaaagug 9120
aucagcagcu gggaguccua caagagcggc ggagagacaa gacugugacc gcuacgcccc 9180
aaugacccga ccagcuaagu aacgauacag cagcaauugg caagcugcuu acauagaacu 9240
cgcggcgauu ggcaugccgc uuuaaaauuu uuauuuuauu uuucuuuucu uuuccgaauc 9300
ggauuuuguu uuuaauauuu c 9321

<210> SEQ ID NO 7
<211> LENGTH: 9710
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: CHIKV-S27 RABV-G srRNA construct

<400> SEQUENCE: 7
gauggcugcg ugagacacac guagccuacc aguuucuuac ugcucuacuc ugcaaagcaa 60
gagauuaaga acccaucaug gauccugugu acguggacau agacgcugac agcgccuuuu 120
ugaaggcccu gcaacgugcg uaccccaugu uugaggugga accuaggcag gucacaccga 180
augaccaugc uaaugcuaga gcguucucgc aucuagcuau aaaacuaaua gagcaggaaa 240
uugaucccga cucaaccauc cuggauauug guagugcgcc agcaaggagg augaugucgg 300
acaggaagua ccacugcguu ugcccgaugc gcagugcaga agaucccgag agacucgcca 360
auuaugcgag aaagcuagca ucugccgcag gaaaaguccu ggacagaaac aucucuggaa 420
agaucgggga cuuacaagca guaauggccg ugccagacac ggagacgcca acauucugcu 480
uacacacaga uguaucaugu agacagagag cagacgucgc gauauaccaa gacgucuaug 540
cuguacacgc acccacgucg cuauaccacc aggcgauuaa aggggguccga uuggcguacu 600 ggguagggguu ugacacaacc ccguucaugu acaaugccau ggcgggugcc uaccccucau 660
acucgacaaa uugggcagau gagcagguac ugaaggcuaa gaacauagga uuauguucaa 720
cagaccugac ggaagguaga cgaggcaaau ugucuauuau gagaggaaaa aagcuagaac 780

-continued

```
cgugcgaccg ugugcuguuc ucaguagggu caacgcucua cccggaaagc cguaagcuac    840
uuaagagcug gcaccuacca ucgguguucc auuuaaaggg caagcucagc uucacaugcc    900
gcugugauac agugguuucg ugcgaaggcu acgucguuaa gagaauaacg augagcccag    960
gccuuuacgg aaaaaccaca ggguaugcgg uaacccacca cgcagacgga uuccugaugu   1020
gcaagaccac cgacacgguu gacggcgaaa gagugucauu cucggugugc acguacgugc   1080
cggcgaccau uugugaucaa augaccggca uccuugcuac agaagucacg ccggaggaug   1140
cacagaagcu guuggugggg cugaaccaga gaauaguggu uaacggcaga acgcaacgga   1200
auacgaacac caugaaaaac uauaugauuc ccguggucgc ccaagccuuc aguaaguggg   1260
caaaggagug ccggaaagac auggaagaug aaaaacuccu gggggucaga gaaagaacac   1320
ugaccugcug cugucuaugg gcauuuaaga agcagaaaac acacacgguc uacaagaggc   1380
cugauaccca gucaauucag aagguucagg ccgaguuuga cagcuuugug guaccgagcc   1440
uguggucguc cggguuguca aucccguuga ggacuagaau caaaugguug uuaagcaagg   1500
ugccaaaaac cgaccugacc ccauacagcg gggacgccca agaagcccgg gacgcagaaa   1560
aagaagcaga ggaagaacga gaagcagaac ugacucuuga agcccuacca ccccuucagg   1620
cagcacagga agauguucag gucgaaaucg acguggaaca gcuugaggac agagcgggug   1680
caggaauaau agagacuccg agaggagcua ucaaaguuac ugcccaacca acagaccacg   1740
ucgugggaga guacuugguu cuuuccccgc agaccguacu acguagccaa aagcuuagcc   1800
ugauucacgc uuuggcggag caagugaaga cgugcacgca cagcggacga gcagggaggu   1860
augcggucga agcguacgac ggcagagucc uagugcccuc aggcuacgca aucucgccug   1920
aagacuucca gagccuaagc gaaagcgcaa cgauggugua caacgaaaga gaguucguaa   1980
acagaaagcu acaccauauu gcgaugcaug gaccagcccu gaacaccgac gaagagucgu   2040
augagcuggu gagggcagag aggacagaac acgaguacgu cuacgacgug gaccagagaa   2100
gaugcuguaa gaaggaagaa gcugcaggac ugguacuggu gggcgacuug acuaauccgc   2160
ccuaccacga auucgcauau gaagggcuaa aaauccgccc ugccugccca uacaaaauug   2220
cagucauagg agucuucgga guaccaggau cuggcaaguc agcuauuauc aagaaccuag   2280
uuaccaggca agaccuggug acuagcggaa agaaagaaaa cugccaagaa aucaccaccg   2340
acgugaugag acagagaggu cuagagauau cugcacguac gguugacucg cugcucuuga   2400
auggauguaa cagaccaguc gacguguugu acguagacga ggcguuugcg ugccacucug   2460
gaacguuacu ugcauugauc gccuugguga gaccaagaca gaaaguugua cuuuguggug   2520
acccgaagca gugcggcuuc uucaauauga ugcagaugaa agucaacuau aaucacaaca   2580
ucugcaccca aguguaccac aaaaguaucu ccaggcggug uacacugccu gugacugcca   2640
uugugucauc guugcauuac gaaggcaaaa ugcgcacuac gaaugaguac aacaagccga   2700
uuguagugga cacuacaggc ucaacaaaac cugacccugg agaucucgug uuaacgugcu   2760
ucagaggaug gguuaaacaa cugcaaauug acuaucgugg acacgagguc augacagcag   2820
ccgcauccca aggguuaacc agaaaaggag uuuacgcagu uaggcaaaaa guuaacgaaa   2880
acccgcuuua ugcaucaacg ucagagcacg ucaacguacu ccuaacgcgu acggaaggua   2940
aacugguaug gaagacacuc uccggugacc cguggauaaa gacgcugcag aacccaccga   3000
aaggaaacuu caaagcaacu auuaaggagu gggaggugga gcaugcauca auaauggcgg   3060
gcaucugcag ucaccaaaug accuuugaua cauuccaaaa caaagccaac guuuguuggg   3120
cuaagaguuu gguccuauc cucgaaacag cggggauaaa acuaaacgac aggcaguggu   3180
```

```
cccagauaau ucaagccuuc aaagaagaca aagcauauuc acccgaagua gcccugaaug   3240
aaauaugcac gcgcauguau ggggguggauc uagacagcgg gcuauuuucu aaaccguugg   3300
ugucugugua uuacgcggau aaccacuggg auaauaggcc uggagggaag auguucggau   3360
ucaaccccga ggcagcaucc auucuagaaa gaaaguaucc auuuacaaaa gggaagugga   3420
acaucaacaa gcagaucugc gugacuacca ggaggauaga agacuucaac ccuaccacca   3480
acauuauacc ggccaacagg agacuaccac acucauuagu ggccgaacac cgcccaguaa   3540
aaggggaaag aauggaaugg cugguuaaca agauaaacgg ccaccacgug cuccugguca   3600
guggcuguag ccuugcacug ccuacuaaga gagucacuug gguagcgcca cuaggugucc   3660
gcggagcgga cuauacauac aaccuagagu ugggucugcc agcaacgcuu gguagguaug   3720
accuagnggu cauaaacauc cacacaccuu uucgcauaca ccauuaucaa cagugcguag   3780
accacgcaau gaaacugcaa augcucgggg gugacucauu gagacugcuc aaaccgggug   3840
gcucucuauu gaucagagca uaugguuacg cagauagaac cagugaacga gucaucugcg   3900
uauugggacg caaguuuaga ucaucuagag cguugaaacc accaugugc accagcaaca   3960
cugagauguu uuuucuauuc agcaacuuug acaauggcag aaggaauuuc acaacucaug   4020
ucaugaacaa ucaacugaau gcagccuuug uaggacaggc cacccgagca ggaugugcac   4080
cgucguaccg gguaaaacgc auggauaucg cgaagaacga ugaagagugc guagucaacg   4140
ccgccaaccc ucgcggguua ccaggugacg guguuugcaa ggcaguauac aaaaaauggc   4200
cggaguccuu uaagaacagu gcaacaccag ugggaaccgc aaaaacaguc augugcggua   4260
cguauccagu aauccacgcc guuggaccaa acuucucuaa uuauucggag ucugaagggg   4320
accgagaauu ggcggcugcc uaucgagaag ucgcaaagga gguaacuaga cugggaguaa   4380
auaguguagc uauaccucuc cucuccacag guguauacuc aggagggaaa gacaggcuga   4440
cccagucacu gaaccaccuc uuuacagcca uggacucgac ggaugcagac guggucaucu   4500
acugccgcga caaagaaugg gagaagaaaa uaucugaggc cauacagaug cggacccaag   4560
uggagcugcu ggaugagcac aucuccauag acugcgaugu uguucgcgug cacccugaca   4620
gcagcuuggc aggcagaaaa ggauacagca ccacggaagg cgcacuguac ucauaucuag   4680
aagggacccg uuuucaccaa acggcagugg auauggcaga gauauauacu auguggccaa   4740
agcaaacaga ggccaacgag caaguuugcc uauaugcccu gggggaaagu auugaaucga   4800
ucaggcagaa augcccggug gaugaugcag augcaucauc ucccccgaaa acugucccgu   4860
gccucugccg uuacgccaug acaccagaac gcguuacccg acuucgcaug aaccauguca   4920
caagcauaau uguguguucu ucguuucccc uuccaaagua caaaauagaa ggagugcaaa   4980
aagucaaaug cuccaaggua augcuauuug accacaacgu gccaucgcgc guaaguccaa   5040
gggaauacag accuucccag gagucuguac aggaagcgag uacgaccacg ucacugacgc   5100
auagccaauu cgaucuaagc guugacggca agauacugcc cgucccguca gaccuggaug   5160
cugacgcccc agcccuagaa ccagcccuug acgacggggc gauacacacg uugccaucug   5220
caaccggaaa ccuugcggcc gugucugacu ggguaaugag caccguaccu gucgcgccgc   5280
ccagaagaag gcgagggaga aaccugacug ugacaugcga cgagagagaa gggaauauaa   5340
cacccauggc uagcguccga uucuuuaggg cagagcugug uccagucgua caagaaacag   5400
cggagacgcg ugacacagcu augucucuuc aggcaccgcc gaguaccgcc acggaacuga   5460
gucacccgcc gaucuccuuc ggugcaccaa gcgagacguu ccccaucaca uuugggggacu   5520
```

-continued

```
ucaacgaagg agaaaucgaa agcuugucuu cugagcuacu aacuuucgga gacuuccuac   5580
ccggagaagu ggaugauuug acagauagcg acugguccac gugcucagac acggacgacg   5640
aguuacgacu agacagggca gguggguaua uauucucguc ggacacuggu ccaggucauu   5700
uacaacagaa gucaguacgc cagucagugc ugccggugaa cacccuggag gaaguccacg   5760
aggagaagug uuacccaccu aagcuggaug aagcaaagga gcaacuacua cuuaagaaac   5820
uccaggagag ugcauccaug gccaacagaa gcagguauca gucgcgcaaa guagaaaaca   5880
ugaaagcaac aaucauccag agacuaaaga gaggcuguag auuauacuua augucagaga   5940
ccccaaaagu cccuaccuac cggaccacau auccggcgcc uguguacucg ccuccgauua   6000
acguccgacu guccaacccc gaguccgcag uggcagcaug caaugaguuc uuggcuagaa   6060
acuauccaac uguuucauca uaccaaauca ccgacgagua ugaugcauau cuagacaugg   6120
uggacggguc ggagaguugu cuggaccgag cgacauucaa uccgucaaaa cuuaggagcu   6180
acccaaaaca gcacgcuuac cacgcgcccu ccaucagaag cgcuguaccg uccccauucc   6240
agaacacacu acagaaugua cuggcagcag ccacgaaaag aaacugcaac gucacacaga   6300
ugagggaauu acccacuuug gacucagcag uauucaacgu ggaguguuuc aaaaaauucg   6360
caugcaacca agaauacugg gaagaauuug cugccagccc uaucaggaua acaacugaga   6420
auuuaacaac cuauguuacu aaacuaaagg ggccaaaagc agcagcgcua uuugcaaaaa   6480
cccauaaucu gcugccacug caggaagugc caauggauag guucacagua gacaugaaaa   6540
gggaugugaa ggugacuccu gguacaaagc acacagagga aagaccuaag guacagguua   6600
uacaggcggc ugaacccuug gcaacagcau accuaugugg gauucacaga gagcugguua   6660
ggaggcugaa cgccguccuc cuacccaaug uacauacacu auuugacaug ucugccgagg   6720
auuucgaugc caucauagcc gcacacuuua agccaggaga cacuguuuua gaaacggaca   6780
uagccuccuu ugauaagagc caagaugauu cacuugcgcu uacugcuuua augcuguuag   6840
aggauuuagg gguggaucac ucccuguugg acuugauaga ggcugcuuuc ggagagauuu   6900
ccagcuguca ucuaccgaca gguacgcgcu ucaaguucgg cgccaugaug aaaucuggua   6960
uguuccuaac ucuguucguc aacacacugc uaaauaucac caucgccagc cgagugcugg   7020
aagaucgucu gacaaaaucc gcgugcgcag ccuucaucgg cgacgacaac auaauacaug   7080
gagucgucuc cgaugaauug auggcagcca gaugcgccac uuggaugaac auggaaguga   7140
agaucauaga ugcaguugua ucccagaaag ccccuuacuu uuguggaggg uuuauacugc   7200
acgauaucgu gacaggaaca gcuugcagag uggcagaccc gcuaaaaagg cuauuuaaac   7260
ugggcaaacc gcuagcggca ggugacgaac aagaugagga uagaagacga gcgcuggcug   7320
acgaagugg u cagauggcaa cgaacagggc uaauugauga guuggagaaa gcgguauacu   7380
cuagguauga agugcagggu auaucaguug ugguaauguc cauggccacc uuugcaagcu   7440
ccagauccaa cuucgagaag cucagaggac ccgucguaac uuuguacggc gguccuaaau   7500
agguacgcac uacagcuacc uauuuugcag aagccgacag uaaguaccua aacacuaauc   7560
agcuacacug gagacgugga ggagaacccu ggaccuaugg ugccucaggu gcugcuguuu   7620
gugccucugc ugggcuucag ccugugcuuc ggcaaguucc ccaucuacac aauccccgac   7680
aagcucggcc cuuggagccc caucgauauc caccaccuga gcugccccaa caaccuggug   7740
guggaagaug agggcugcac caaccugagc gaguucagcu acauggaacu gaaagugggc   7800
uacaucagcg ccaucaaagu gaacggcuuc accuguaccg gcgugguc ac agaggccgag   7860
acauacacca acuucguggg cuacgugacc accaccuuca agcggaagca cuucagaccc   7920
```

acaccugacg ccuguagagc cgccuacaac uggaaaaugg ccggcgaucc cagauacgag 7980
gaaagccugc acaaccccua uccugacuac cacuggcugc ggaccgugaa aaccaccaaa 8040
gagagccugg ucaucaucag ccccagcgug accgaccugg auccuuacga uaagagccug 8100
cacucccggg uguucccugg cggaaauugc ucuggcauca ccguguccag caccuacugc 8160
agcaccaacc acgacuacac caucuggaug cccgagaacc ugagacuggg caccagcugc 8220
gacaucuuca ccaacagcag aggaaagcgg gccagcaaag gcggcaagac cuguggcuuu 8280
guggacgaga gaggccugua caagucucug aagggcgccu gcaagcugaa gcugugcgga 8340
guucugggac ugagacugau ggauggcacc ugggucgcca ugcagaccag cgacgagaca 8400
aagugguguc cuccuggcca gcuggucaac cugcacgacu uuagauccga cgagaucgag 8460
caucuggugg ucgaggaacu ggucaagaaa cgggaagagu gccuggacgc ccuggaaucc 8520
aucaugacca ccaagagcgu guccuuccgg cggcugucuc accugagaaa acuggugccu 8580
ggcuuuggca aggccuauac caucuucaac aagacccuga uggaagccga cgcucacuac 8640
aagucugugc ggaccuggaa cgagaucauc cccagcaagg gcugccugag aguuggcgga 8700
agaugucacc cucacgugaa cggcguguuc uucaacggca ucauccuggg cucugacggc 8760
cacgugcuga ucccugaaau gcagucuagc cugcuccagc agcauaugga acugcuggaa 8820
agcagcguga ucccucugau gcacccucug gccgauccua gcaccguguu caaggauggc 8880
gacgaggucg aggacuucgu ggaagugcau cugcccgacg ugcacgagca agugucuggc 8940
guugaacugg gccugccuaa cuggggcaaa uaugugcuga ugaucgcugg ggcccugauc 9000
gcccugaugc ugaucaucuu ccugaugacc ugcugucgga gagugaacag acccgagagc 9060
acacagagca gccugggaga gacaggcaga aacguguccg ugacaagcca gagcggcaaa 9120
gugaucagca gcugggaguc cuacaagagc ggcggagaga caagacugug accgcuacgc 9180
cccaaugacc cgaccagcuu gacgacuaag caugaaggua uaugugcccc cuaagagaca 9240
caccguauau agcuaauaau cuguagauca aagggcuaua uaaccccuga auaguaacaa 9300
aauacaaaau cacuaaaaau uauaaaaaaa aaaaaaaaaa aacagaaaaa uauauaaaua 9360
gguauacgug uccccuaaga gacacauugu auguagguga uaaguauaga ucaaagggcc 9420
gaacaacccc ugaauaguaa caaaauauaa aaauuaauaa aaaucauaaa auagaaaaac 9480
cauaaacaga aguaguucaa agggcuauaa aaaccccuga auaguaacaa aacauaaaac 9540
uaauaaaaau caaaugaaua ccauaauugg caaacggaag agauguaggu acuuaagcuu 9600
ccuaaaagca gccgaacuca cuuugagaug uaggcauagc auaccgaacu cuuccacgau 9660
ucuccgaacc cacagggacg uaggagaugu uauuuuguuu uuaauauuuc 9710

<210> SEQ ID NO 8
<211> LENGTH: 9709
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: CHIKV-DRDE RABV-G srRNA construct

<400> SEQUENCE: 8
gauggcugcg ugagacacac guagccuacc aguuucuuac ugcucuacuc ugcaaagcaa 60
gagauuaaua acccaucaug gauccugugu acguggacau agacgcugac agcgccuuuu 120
ugaaggcccu gcaacgugcg uaccccaugu uugaggugga accaaggcag gucacaccga 180

-continued

```
augaccaugc uaaugcuaga gcguucucgc aucuagcuau aaaacuaaua gagcaggaaa    240
uugaccccga cucaaccauc cuggauaucg gcagugcgcc agcaaggagg augaugucgg    300
acaggaagua ccacugcguc ugcccgaugc gcagugcgga agaucccgag agacucgcua    360
auuaugcgag aaagcuagca ucugccgcag gaaaaguccu ggacagaaac aucucuggaa    420
agaucgggga cuuacaagca guaauggccg ugccagacaa ggagacgcca acauucugcu    480
uacacacaga cgucucaugu agacagagag cagacgucgc uauauaccaa gacgucuaug    540
cuguacacgc acccacgucg cuauaccacc aggcgauuaa aggggucoga guggcguacu    600
gguugggguu cgacacaacc ccguucaugu acaaugccau ggcgggugcc uaccccucau    660
acucgacaaa cugggcagau gagcagguac ugaaggcuaa gaacauagga uuauguucaa    720
cagaccugac ggaagguaga cgaggcaagu ugucuauuau gagagggaaa aagcuaaaac    780
cgugcgaccg ugugcuguuc ucaguagggu caacgcucua cccggaaagc cgcaagcuac    840
uuaagagcug gcaccugcca ucgguguucc auuuaaaggg caaacucagc uucacaugcc    900
gcugugauac agugguuucg ugugagggcu acgucguuaa gagaauaacg augagcccag    960
gccuuuaugg aaaaaccaca ggguaugcgg uaacccacca cgcagacgga uuccugcugu   1020
gcaagacuac cgacacgguu gacggcgaaa gagugucauu cucggugugc acauacgugc   1080
cggcgaccau uugugaucaa augaccggca uccuugcuac agaagucacg ccggaggaug   1140
cacagaagcu guuggugggg cugaaccaga gaauaguggu uaacggcaga acgcaacgga   1200
auaugaacac caugaaaaau uaucugcuuc ccguggucgc ccaagccuuc aguaaguggg   1260
caaaggagug ccggaaagac auggaagaug aaaaacuccu gggggucaga gaaagaacac   1320
ugaccugcug cugucuaugg gcauucaaga agcagaaaac acacacgguc uacaagaggc   1380
cugauaccca gucaauucag aagguucagg ccgaguuuga cagcuuugug guaccgaguc   1440
uguggucguc cggguuguca aucccuuuga ggacuagaau caaaugguug uuaagcaagg   1500
ugccaaaaac cgaccugauc ccauacagcg gagacgcccg agaagcccgg gacgcagaaa   1560
aagaagcaga ggaagaacga gaagcagaac ugacucgcga agcccuacca ccucuacagg   1620
cagcacagga agauguucag gucgaaaucg acguggaaca gcuugaggac agagcgggcg   1680
caggaauaau agagacuccg agaggagcua ucaaaguuac ugcccaacca acagaccacg   1740
ucgugggaga guaccuggua cucuccccgc agaccguacu acguagccag aagcucaguc   1800
ugauucacgc uuuggcggag caagugaaga cgugcacgca caacggacga gcagggaggu   1860
augcggucga agcguacgac ggccgagucc uagugcccuc aggcuaugca aucucgccug   1920
aagacuucca gagucuaagc gaaagcgcga cgauggugua uaacgaaaga gaguucguaa   1980
acagaaagcu acaccauauu gcgaugcacg gaccagcccu gaacaccgac gaagagucgu   2040
augagcuggu gagggcagag aggacagaac acgaguacgu cuacgacgug gaucagagaa   2100
gaugcuguaa gaaggaagaa gccgcaggac ugguacuggu gggcgacuug acuaauccgc   2160
ccuaccacga auucgcauau gaagggcuaa aaauccgccc ugccugccca uacaaaauug   2220
cagucauagg agucuucgga guaccgggau cuggcaaguc agcuauuauc aagaaccuag   2280
uuaccaggca ggaccuggug acuagcggaa agaaagaaaa cugccaagaa aucaccaccg   2340
acgugaugag acagagaggu cuagagauau cugcacguac gguugacucg cugcucuuga   2400
auggaugcaa cagaccaguc gacguguugu acguagacga ggcguuugcg ugccacucug   2460
gaacgcuacu ugcuuugauc gccuugguga gaccaaggca gaaaguugua cuuugugug   2520
```

```
acccgaagca gugcggcuuc uucaauauga ugcagaugaa agucaacuau aaucacaaca   2580
ucugcaccca aguguaccac aaaaguaucu ccaggcggug uacacugccu gugaccgcca   2640
uugugucauc guugcauuac gaaggcaaaa ugcgcacuac gaaugaguac aacaagccga   2700
ucguagugga cacuacaggc ucaacaaaac cugacccugg agaccucgug uuaacgugcu   2760
ucagagggug gguuaaacaa cugcaaauug acuaucgugg auacgagguc augacagcag   2820
ccgcauccca aggguuaacc agaaaaggag uuuacgcagu uagacaaaaa guuaaugaaa   2880
acccgcucua ugcaucaacg ucagagcacg ucaacguacu ccuaacgcgu acggaaggua   2940
aacugguaug gaagacacuu uccggcgacc cguggauaaa gacgcugcag aacccaccga   3000
aaggaaacuu caaagcaacu auuaaggagu gggaggugga gcaugcauca auaauggcgg   3060
gcaucugcag ucaccaaaug accuucgaua cauuccaaaa uaaagccaac guuuguuggg   3120
cuaagagcuu gguccccuauc cucgaaacag cggggauaaa acuaaaugau aggcaguggu   3180
cucagauaau ucaagccuuc aaagaagaca aagcauacuc accugaagua gcccugaaug   3240
aaauauguac gcgcauguau gggguggauc uagacagcgg gcuauuuucu aaaccguugg   3300
ugucugugua uuacgcggau aaccacuggg auaauaggcc uggagggaaa auguucggau   3360
uuaaccccga ggcagcaucc auucuagaaa gaaaguaucc auucacaaaa gggaagugga   3420
acaucaacaa gcagaucugc gugacuacca ggaggauaga agacuuuaac ccuaccacca   3480
acaucauacc ggccaacagg agacuaccac acucauuagu ggccgaacac cgcccaguaa   3540
aaggggaaag aauggaaugg cugguuaaca agauaaacgg ccaccacgug cuccugguca   3600
guggcuauaa ccuugcacug ccuacuaaga gagucacuug gguagcgccg uuagguguccc  3660
gcggagcgga cuacacauac aaccuagagu ugggucugcc agcaacgcuu gguagguaug   3720
accuuguggu cauaaacauc cacacaccuu uucgcauaca ccauuaccaa cagugcgucg   3780
accacgcaau gaaacugcaa augcucgggg gugacucauu gagacugcuc aaaccgggcg   3840
gcucucuauu gaucagagca uaugguuacg cagauagaac cagugaacga gucaucugcg   3900
uauugggacg caaguuuaga ucgucuagag cguugaaacc accaugug uc accagcaaca   3960
cugagauguu uuuccuauuc agcaacuuug acaauggcag aaggaauuuc acaacucaug   4020
ucaugaacaa ucaacugaau gcagccuucg uaggacaggu cacccgagca ggaugugcac   4080
cgucguaccg gguaaaacgc auggacaucg cgaagaacga ugaagagugc guagucaacg   4140
ccgcuaaccc ucgcggguua ccgggugacg guguuugcaa ggcaguauac aaaaaauggc   4200
cggaguccuu uaagaacagu gcaacaccag ugggaaccgc aaaaacaguu augugcggua   4260
cguauccagu aauccacgcu guuggaccaa acuucucuaa uuauucggag ucugaagggg   4320
accgggaauu ggcagcugcc uaucgagaag ucgcaaagga aguaacuagg cugggaguaa   4380
auaguguagc uauaccucuc cucuccacag guguauacuc aggagggaaa gacaggcuga   4440
cccagucacu gaaccaccuc uuuacagcca uggacucgac ggaugcagac guggucaucu   4500
acugccgcga caaagaaugg gagaagaaaa uaucugaggc cauacagaug cggacccaag   4560
uagagcugcu ggaugagcac aucuccauag acugcgauau uguucgcgug cacccugaca   4620
gcagcuuggc aggcagaaaa ggauacagca ccacggaagg cgcacuguac ucauaucuag   4680
aagggacccg uuuucaucag acggcugugg auauggcgga gauacauacu auguggccaa   4740
agcaaacaga ggccaaugag caagucugcc uauaugcccu gggggaaagu auugaaucga   4800
ucaggcagaa augcccggug gaugaugcag acgcaucauc uccccccaaa acugucccgu   4860
gccuuugccg uuacgcuaug acuccagaac gcgucacccg gcuucgcaug aaccacguca   4920
```

-continued

```
caagcauaau ugugugguucu ucguuucccc ucccaaagua caaaauagaa ggagugcaaa   4980
aagucaaaug cucuaaggua augcuauuug accacaacgu gccaucgcgc guaaguccaa   5040
gggaauauag aucuucccag gagucugcac aggaggcgag uacaaucacg ucacugacgc   5100
auagucaauu cgaccuaagc guugauggcg agauacugcc cgucccguca gaccuggaug   5160
cugacgcccc agcccuagaa ccagcacuag acgacggggc gacacacacg cugccaucca   5220
caaccggaaa ccuugcggcc gugucugacu ggguaaugag caccguaccu gucgcgccgc   5280
ccagaagaag gcgagggaga aaccugacug ugacauguga cgagagagaa gggaauauaa   5340
cacccauggc uagcguccga uucuuuaggg cagagcugug uccggucgua caagaaacag   5400
cggagacgcg ugacacagca augucucuuc aggcaccacc gaguaccgcc acggaaccga   5460
aucauccgcc gaucuccuuc ggagcaucaa gcgagacguu ccccauuaca uuuggggacu   5520
ucaacgaagg agaaaucgaa agcuugucuu cugagcuacu aacuuucgga gacuucuuac   5580
caggagaagu ggaugacuug acagacagcg acugguccac gugcucagac acggacgacg   5640
aguuaugacu agacagggca ggugggguaua uauucucguc ggacaccggu ccaggucauu   5700
uacaacagaa gucaguacgc cagucagugc ugccggugaa cacccuggag gaaguccacg   5760
aggagaagug uuacccaccu aagcuggaug aagcaaagga gcaacuauua cuuaagaaac   5820
uccaggagag ugcauccaug gccaacagaa gcagguauca gucgcgcaaa guagaaaaca   5880
ugaaagcagc aaucauccag agacuaaaga gaggcuguag acuauacuua augucagaga   5940
ccccaaaagu cccuacuuac cggacuacau auccggcgcc uguguacucg ccuccgauca   6000
acguccgauu guccaauccc gaguccgcag uggcagcaug caaugaguuc uuagcuagaa   6060
acuauccaac ugucucauca uaccaaauua ccgacgagua ugaugcauau cuagacaugg   6120
uggacggguc ggagaguugc cuggaccgag cgacauucaa uccgucaaaa cucaggagcu   6180
acccgaaaca gcacgcuuac cacgcgcccu ccaucagaag cgcuguaccg uccccauucc   6240
agaacacacu acagaaugua cuggcagcag ccacgaaaag aaacugcaac gucacacaga   6300
ugagggaauu acccacuuug gacucagcag uauucaacgu ggaguguuuc aaaaaguucg   6360
caugcaacca agaauacugg gaagaauuug cugccagccc uauuaggaua acaacugaga   6420
auuuagcaac cuauguuacu aaacuaaaag ggccaaaagc agcagcgcua uucgcaaaaa   6480
cccauaaucu acugccacua caggaaguac caauggauag guucacagua gauaugaaaa   6540
gggacgugaa ggugacuccu gguacaaagc auacagagga aagaccuaag gugcagguua   6600
uacaggcggc ugaacccuug gcgacagcau accuaugugg gauucacaga gagcugguua   6660
ggaggcugaa cgccguccuc cuacccaaug uacauacacu auuugacaug ucugccgagg   6720
auuucgaugc caucauagcc gcacacuuua agccaggaga cacuguuuug gaaacggaca   6780
uagccuccuu ugauaagagc caagaugauu cacuugcgcu uacugcuuug augcuguuag   6840
aggauuuagg gguggaucac ucccugcugg acuugauaga ggcugcuuuc ggagagauuu   6900
ccagcuguca ccuaccgaca gguacgcgcu ucaaguucgg cgccaugaug aaaucaggua   6960
uguuccuaac ucuguucguc aacacauugu uaaacaucac caucgccagc cgagugcugg   7020
aagaucgucu gacaaaaucc gcgugcgcgg ccuucaucgg cgacgacaac auaauacaug   7080
gagucgucuc cgaugaauug auggcagcca gaugugccac uuggaugaac auggaaguga   7140
agaucauaga ugcaguugua uccuugaaag ccccuuacuu uuguggaggg uuuauacugc   7200
acgauacugu gacaggaaca gcuugcagag uggcagaccc gcuaaaaagg cuuuuuaaac   7260
```

-continued

```
ugggcaaacc gcuagcggca ggugacgaac aagaugaaga uagaagacga gcgcuggcug   7320
acgaagugau cagauggcaa cgaacagggc uaauugauga gcuggagaaa gcgguauacu   7380
cuagguacga agugcagggu auaucaguug ugguaauguc cauggccacc uuugcaagcu   7440
ccagauccaa cuucgagaag cucagaggac ccgucauaac uuuguacggc gguccuaaau   7500
agguacgcac uacagcuacc uauuuugcag aagccgacag caaguaucua aacacuaauc   7560
agcuacacug gagacgugga ggagaacccu ggaccuaugg ugccucaggu gcugcuguuu   7620
gugccucugc ugggcuucag ccugugcuuc ggcaaguucc ccaucuacac aaucccccgac   7680
aagcucggcc cuuggagccc caucgauauc caccaccuga gcugccccaa caaccuggug   7740
guggaagaug agggcugcac caaccugagc gaguucagcu acauggaacu gaaagugggc   7800
uacaucagcg ccaucaaagu gaacggcuuc accuguaccg gcgugguucac agaggccgag   7860
acauacacca acuucguggg cuacgugacc accaccuuca agcggaagca cuucagaccc   7920
acaccugacg ccuguagagc cgccuacaac uggaaaaugg ccggcgaucc cagauacgag   7980
gaaagccugc acaaccccua uccugacuac cacuggcugc ggaccgugaa aaccaccaaa   8040
gagagccugg ucaucaucag ccccagcgug accgaccugg auccuuacga uaagagccug   8100
cacucccggg uguucccugg cggaaauugc ucuggcauca ccgugucccag caccuacugc   8160
agcaccaacc acgacuacac caucuggaug cccgagaacc ugagacuggg caccagcugc   8220
gacaucuuca ccaacagcag aggaaagcgg gccagcaaag gcggcaagac cuguggcuuu   8280
guggacgaga gaggccugua caagucucug aagggcgccu gcaagcugaa gcugugcgga   8340
guucugggac ugagacugau ggauggcacc ugggucgcca ugcagaccag cgacgagaca   8400
aaguggugcc cuccuggcca gcuggucaac cugcacgacu uuagauccga cgagaucgag   8460
caucuggugg ucgaggaacu ggucaagaaa cgggaagagu gccuggacgc ccuggaaucc   8520
aucaugacca ccaagagcgu guccuucccgg cggcugucuc accugagaaa acuggugccu   8580
ggcuuuggca aggccuauac caucuucaac aagacccuga uggaagccga cgcucacuac   8640
aagucugugc ggaccuggaa cgagaucauc cccagcaagg gcugccugag aguuggcgga   8700
agaugucacc cucacgugaa cggcguguuc uucaacggca ucauccuggg cucugacggc   8760
cacgugcuga ucccugaaau gcagucuagc cugcuccagc agcauaugga acugcuggaa   8820
agcagcguga ucccucugau gcacccucug gccgauccua gcaccguguu caaggauggc   8880
gacgaggucg aggacuucgu ggaagugcau cugcccgacg ugcacgagca agugucuggc   8940
guugaacugg gccugccuaa cuggggcaaa uaugugcuga ugaucgcugg ggcccugauc   9000
gcccugaugc ugaucaucuu ccugaugacc ugcugucgga gagugaacag acccgagagc   9060
acacagagca gccugggaga gacaggcaga aacguguccg ugacaagcca gagcggcaaa   9120
gugaucagca gcugggaguc cuacaagagc ggcggagaga caagacugug accgcuacgc   9180
cccaaugacc cgaccagcuu gacgacuaag caugaaggua uaugugucccc cuaagagaca   9240
caccguauau agcuaauaau cuguagauca aagggcuaua uaaccccuga auaguaacaa   9300
aauacaaaau cacuaaaaau uauaaaaaaa aaaaaaaaaa acagaaaaau auauaaauag   9360
guauacgugu ccccuaagag acacauugua uguaggugau aaguauagau caaagggccg   9420
aacaaccccu gaauaguaac aaaauauaaa aauuaauaaa aaucauaaaa uagaaaaacc   9480
auaaacagaa guaguucaaa gggcuauaaa aaccccugaa uaguaacaaa acauaaaacu   9540
aauaaaaauc aaaugaauac cauaauuggc aaacggaaga gauguaggua cuuaagcuuc   9600
cuaaaagcag ccgaacucac uuugagaugu aggcauagca uaccgaacuc uuccacgauu   9660
```

cuccgaaccc acagggacgu aggagauguu auuuuguuuu uaauauuuc 9709

<210> SEQ ID NO 9
<211> LENGTH: 9714
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: SINV-G RABV-G srRNA construct

<400> SEQUENCE: 9
gauuggcggc guaguacaca cuauugaauc aaacagccga ccaauugcac uaccaucaca 60
auggagaagc caguaguuaa cguagacgua gacccgcaga guccguuugu cgugcaacug 120
caaaagagcu ucccgcaauu ugagguagua gcacagcagg ucacuccaaa ugaccaugcu 180
aaugccagag cauuuucgca ucuggccagu aaacuaaucg agcuggaggu uccuaccaca 240
gcgacgauuu uggacauagg cagcgcaccg gcucguagaa uguuuuccga gcaccaguac 300
cauugcguuu gccccaugcg uaguccagaa gacccggacc gcaugaugaa auaugccagc 360
aaacuggcgg aaaaagcaug caagauuacg aauaagaacu ugcaugagaa gaucaaggac 420
cuccggaccg uacuugauac accggaugcu gaaacgccau cacucugcuu ccacaacgau 480
guuaccugca acacgcgugc cgaguacucc gucaugcagg acguguacau caacgcaccc 540
ggaacuauuu accaucaggc uaugaaaggc gugcggaccc uguacuggau uggcuucgau 600
accacccagu ucauguucuc ggcuauggca gguucguacc cugcguacaa caccaacugg 660
gccgacgaaa aaguccucga agcgcguaac aucggacucu gcagcacaaa gcugagugaa 720
ggcaggacag gaaaguuguc gauaaugagg aagaaggagu ugaagcccgg gucacggguu 780
uauuucuccg uuggaucgac acuuuaccca gaacacagag ccagcuugca gagcuggcau 840
cuuccaucgg uguuccaccu gaaaggaaag cagucguaca cuugccgcug ugauacagug 900
gugagcugcg aaggcuacgu agugaagaaa aucaccauca gucccgggau cacgggagaa 960
accgugggau acgcgguuac aaacaauagc gagggcuucu ugcuaugcaa aguuaccgau 1020
acaguaaaag gagaacgggu aucguucccc gugugcacgu auaucccggc caccauaugc 1080
gaucagauga ccggcauaau ggccacggau aucucaccug acgaugcaca aaaacuucug 1140
guugggcuca accagcgaau cgucauuaac gguaagacua acaggaacac caauaccaug 1200
caaaauuacc uucugccaau cauugcacaa ggguucagca aaugggccaa ggagcgcaaa 1260
gaagaccuug acaaugaaaa aaugcugggu accagagagc gcaagcuuac auauggcugc 1320
uugugggcgu uucgcacuaa gaaagugcac ucguucuauc gcccaccugg aacgcagacc 1380
aucguaaaag ucccagccuc uuuuagcgcu uuccccaugu cauccguaug gacuaccucu 1440
uugcccaugu cgcugaggca gaagauaaaa uuggcauuac aaccaaagaa ggaggaaaaa 1500
cugcugcaag ucccggagga auuagucaug gaggccaagg cugcuuucga ggaugcucag 1560
gaggaaucca gagcggagaa gcuccgagaa gcacucccac cauuaguggc agacaaaggu 1620
aucgaggcag ccgcggaagu ugucugcgaa guggaggggc uccaggcgga caucggagca 1680
gcacucgucg aaaccccgcg cggucaugua aggauaaaac cucaagcaaa ugaccguaug 1740
aucggacagu acaucguugu cucgccaacc ucugugcuga agaacgcuaa acucgcacca 1800
gcacacccgc uagcagacca gguuaagauc auaacgcacu ccggaagauc aggaaggugu 1860
gcagucgaac cauacgacgc uaaaguacug augccagcag gaagugccgu accauggcca 1920
gaauucuuag cacugaguga gagcgccacg cuaguguaca acgaaagaga guuugugaac 1980
cgcaagcugu accauauugc caugcacggu cccgcuaaga auacagaaga ggagcaguac 2040
aagguuacaa aggcagagcu cgcagaaaca gaguacgugu uugacgugga caagaagcga 2100
ugcgucaaga aggaagaagc cucaggacuu guccucucgg gagaacugac caacccgccc 2160
uaucacgaac uagcucuuga gggacugaag acucgacccg cgguccccgua caagguugaa 2220
acaauaggag ugauaggcac accaggaucg ggcaagucgg cuaucaucaa gucaacuguc 2280
acggcacgug aucuuguuac cagcggaaag aaagaaaacu gccgcgaaau ugaggccgau 2340
gugcuacggc ugaggggcau gcagaucacg ucgaagacag uggauucggu uaugcucaac 2400
ggaugccaca aagccguaga agugcuguau guugacgaag cguucgcgug ccacgcagga 2460
gcacuacuug ccuugauugc aaucgucaga ccccguaaga agguagugcu augcggagac 2520
ccuaagcaau gcggauucuu caacaugaug caacuaaagg uauauuucaa ccacccggaa 2580
aaagacauau guaccaagac auucuacaag uuuaucuccc gacguugcac acagccaguc 2640
acggcuauug uaucgacacu gcauuacgau ggaaaaauga aaaccacaaa cccgugcaag 2700
aagaacaucg aaaucgacau uacaggggcc acgaagccga agccagggga caucauccug 2760
acaugcuucc gcggguggu uaagcaacug caaaucgacu aucccggaca ugagguaaug 2820
acagccgcgg ccucacaagg gcuaaccaga aaaggaguau augccguccg gcaaaaaguc 2880
aaugaaaacc cgcuguacgc gaucacauca gagcaugugu acgugcugcu cacccgcacu 2940
gaggacaggc uaguauggaa aacuuuacag ggcgacccau ggauuaagca gcucacuaac 3000
guaccaaaag gaaauuuuca agccaccauc gaggacuggg aagcugaaca caagggaaua 3060
auugcugcga uaaacagucc cgcuccccgu accaauccgu ucagcugcaa gacuaacguu 3120
ugcugggcga aagcacugga accgauacug gccacggccg guaucguacu uaccgguugc 3180
caguggagcg agcuguuccc acaguuugca gaugacaaac cacacucggc caucuacgcc 3240
cuggacguaa ucugcauuaa guuuuucggc auggacuuga caagcggacu guuuuccaaa 3300
cagagcaucc cguuaacgua ccauccugcc gauucagcga ggccaguagc ucauugggac 3360
aacagcccag gaacccgcaa guaugguac gaucacgccg uugccgccga acucucccgu 3420
agauuuccgg uguuccagcu agcugggaaa ggcacacagc uugauuugca gacgggcaga 3480
acuagaguua ucuccgcaca gcauaacuug gucccaguga accgcaaucu cccgcacgcc 3540
uuaguccccg agcacaagga gaaacaaccc ggcccgguca aaaaauucuu gagccaguuc 3600
aaacaccacu ccguacuugu ggucucagag gaaaaaaaug aagcuccccca caagagaauc 3660
gaauggaucg ccccgauugg cauagccggc gcugauaaga acuacaaccu ggcuuucggg 3720
uuuccgccgc aggcacggua cgaccuggug uuuaucaaua uuggaacuaa auacagaaac 3780
caucacuuuc agcagugcga agaccaugcg gcgaccuuga aaacccucuc gcguucggcc 3840
cugaacugcc uuaaccccgg aggcacccuc guggugaagu ccuacgguua cgccgaccgc 3900
aauagugagg acguagucac cgcucuugcc agaaaauuug ucagaguguc ugcagcgagg 3960
ccagagugcg ucucaagcaa uacagaaaug uaccugaucu uccgacaacu agacaacagc 4020
cgcacacgac aauucacccc gcaucaucug aauuguguga uuucguccgu guacgagggu 4080
acaagagacg gaguuggagc cgcaccguca uaccgcacua aaagggagaa cauugcugau 4140
ugucaagagg aagcaguugu caaugcagcc aauccgcugg gcagaccagg cgaaggaguc 4200
ugccgugcca ucuauaaacg uuggccgaac aguuucaccg auucagccac agagaccggc 4260

-continued

```
accgcaaaac ugacugugug ccaaggaaag aaagugaucc acgcgguugg cccugauuuc   4320
cggaaacacc cagaggcaga agcccugaaa uugcugcaaa acgccuacca ugcaguggca   4380
gacuuaguaa augaacauaa uaucaagucu gucgccaucc cacugcuauc uacaggcauu   4440
uacgcagccg gaaaagaccg ccuugaagua ucacuuaacu gcuugacaac cgcgcuagau   4500
agaacugaug cggacguaac caucuacugc cuggauaaga aguggaagga aagaaucgac   4560
gcggugcucc aacuuaagga gucuguaaca gagcugaagg augaggauau ggagaucgac   4620
gacgaguuag uauggaucca uccggacagu ugccugaagg gaagaaaggg auucaguacu   4680
acaaaaggaa aguuguauuc guacuuugaa ggcaccaaau uccaucaagc agcaaaagau   4740
auggcggaga uaaagguccu guucccaaau gaccaggaaa gcaacgagca acugugugcc   4800
uacauauugg gggagaccau ggaagcaauc cgcgaaaaau gcccggucga ccacaacccg   4860
ucgucuagcc cgccaaaaac gcugccgugc cucugcaugu augccaugac gccagaaagg   4920
guccacagac ucagaagcaa caacgucaaa gaaguuacag uaugcuccuc cacccccccuu   4980
ccaaaguaca aaaucaagaa cguucagaag guucagugca caaaaguagu ccuguuuaac   5040
ccgcauaccc cugcauucgu ucccgcccgu aaguacauag aagcgccaga acagccugca   5100
gcuccgccug cacaggccga ggaggccccc gaaguugcag caacaccaac accaccugca   5160
gcugauaaca ccucgcuuga ugucacggac aucucacugg acauggaaga caguagcgaa   5220
ggcucacucu uuucgagcuu uagcggaucg gacaacucua uuaccaguau ggacaguugg   5280
ucgucaggac cuaguucacu agagauagua gaccgaaggc agguguggu ggcugacguc   5340
caugccgucc aagagccugc cccuguucca ccgccaaggc uaaagaagau ggcccgccug   5400
gcagcggcaa gaaugcagga ggagccaacu ccaccggcaa gcaccagcuc ugcggacgag   5460
ucccuucacc uuucuuuugg ugggguaucc auguccuucg gaucccuuuu cgacggagag   5520
auggcccgcu uggcagcggc acaacccccg gcaaguacau gcccuacgga ugugccuaug   5580
ucuuucggau cguuuuccga cggagagauu gaggagcuga gccgcagagu aaccgagucu   5640
gagcccgucc uguuugggguc auuugaaccg ggcgaagaga acucaauuau aucgucccga   5700
ucagccguau cuuuuccacc acgcaagcag agacguagac gcaggagcag gaggaccgaa   5760
uacugacuaa ccgggguagg uggguacaua uuuucgacgg acacaggccc ugggcacuug   5820
caaaagaagu ccguucugca gaaccagcuu acagaaccga ccuuggagcg caauguucug   5880
gaaagaaucu acgccccggu gcucgacacg ucgaaagagg aacagcucaa acucagguac   5940
cagaugaugc ccaccgaagc caacaaaagc agguaccagu cuagaaaagu agaaaaucag   6000
aaagccauaa ccacugagcg acugcuuuca gggcuacgac uguauaacuc ugccacagau   6060
cagccagaau gcuauaagau caccuacccg aaaccaucgu auuccagcag uguaccggcg   6120
aacuacucug acccaaaguu ugcuguagcu guuugcaaca acuaucugca ugagaauuac   6180
ccgacgguag caucuuauca gaucaccgac gaguacgaug cuuacuugga uaugguagac   6240
gggacagucg cuugccuaga uacugcaacu uuuugccccg ccaagcuuag aaguuacccg   6300
aaaagacacg aguauagagc cccaaacauc cgcagugcgg uuccaucagc gaugcagaac   6360
acguugcaaa acgugcucau ugccgcgacu aaaagaaacu gcaacgucac acaaaugcgu   6420
gaauugccaa cacuggacuc agcgacauuc aacguugaau gcuuucgaaa auaugcaugu   6480
aaugacgagu auugggagga guuugcccga aagccaauua ggaucacuac ugaguucguu   6540
accgcauacg uggccagacu gaaaggcccu aaggccgccg cacuguucgc aaagacgcau   6600
aauuuggucc cauugcaaga agugccuaug gauagguucg ucauggacau gaaaagagac   6660
```

gugaaaguua caccuggcac gaaacacaca gaagaaagac cgaaaguaca agugauacaa 6720
gccgcagaac cccuggcgac cgcuuaccug ugcgggaucc accgggaguu agugcgcagg 6780
cuuacagccg ucuugcuacc caacauucac acgcuuuuug acaugucggc ggaggacuuu 6840
gaugcaauca uagcagaaca cuucaagcaa ggugacccgg uacuggagac ggauaucgcc 6900
ucguucgaca aaagccaaga cgacgcuaug gcguuaacug gccugaugau cuuggaagac 6960
cugggugugg accaaccacu acucgacuug aucgagugcg ccuuuggaga aauaucaucc 7020
acccaucugc ccacggguac ccguuucaaa uucggggcga ugaugaaauc cggaauguuc 7080
cucacgcucu uugucaacac aguucugaau gucguuaucg ccagcagagu auuggaggag 7140
cggcuuaaaa cguccaaaug ugcagcauuu aucggcgacg acaacaucau acacggagua 7200
guaucugaca aagaaauggc ugagaggugu gccaccuggc ucaacaugga gguuaagauc 7260
auugacgcag ucaucggcga gagaccgccu uacuucugcg guggauucau cuugcaagau 7320
ucgguuaccu ccacagcgug ucgcguggcg gaccccuuga aaaggcuguu uaaguugggu 7380
aaaccgcucc cagccgacga cgagcaagac gaagacagaa gacgcgcucu gcuagaugaa 7440
acaaaggcgu gguuuagagu agguauaaca gacaccuuag caguggccgu ggcaacucgg 7500
uaugagguag acaacaucac accuguccug cuggcauuga gaacuuuugc ccagagcaaa 7560
agagcauuuc aagccaucag aggggaaaua aagcaucucu acgguggucc uaaauaguca 7620
gcauagcaca uuucaucuga cuaauaccac aacaccacca ccaugaauag aggauucuuu 7680
aacaugcucg gccgccgccc cuucccggcc cccacugcca uguggaggcc gcggagaagg 7740
aggcaggcgg ccccgggaag cggagcuacu aacuucagcc ugcugaagca ggcuggagac 7800
guggaggaga acccuggacc uauggugccu caggugcugc uguuugugcc ucugcugggc 7860
uucagccugu gcuucggcaa guuccccauc uacacaaucc ccgacaagcu cggcccuugg 7920
agccccaucg auauccacca ccugagcugc cccaacaacc ugguggugga agaugagggc 7980
ugcaccaacc ugagcgaguu cagcuacaug gaacugaaag ugggcuacau cagcgccauc 8040
aaagugaacg gcuucaccug uaccggcgug gucacagagg ccgagacaua caccaacuuc 8100
gugggcuacg ugaccaccac cuucaagcgg aagcacuuca gacccacacc ugacgccugu 8160
agagccgccu acaacuggaa aauggccggc gaucccagau acgaggaaag ccugcacaac 8220
cccuauccug acuaccacug gcugcggacc gugaaaacca ccaaagagag ccuggucauc 8280
aucagcccca gcgugaccga ccuggauccu uacgauaaga gccugcacuc ccgggguguuc 8340
ccuggcggaa auugcucugg caucaccgug uccagcaccu acugcagcac caaccacgac 8400
uacaccaucu ggaugcccga gaaccugaga cugggcacca gcugcgacau cuucaccaac 8460
agcagaggaa agcgggccag caaaggcggc aagaccugug gcuuugugga cgagagaggc 8520
cuguacaagu cucugaaggg cgccugcaag cugaagcugu gcggaguucu gggacugaga 8580
cugauggaug gcaccugggu cgccaugcag accagcgacg agacaaagug guguccuccu 8640
ggccagcugg ucaaccugca cgacuuuaga uccgacgaga ucgagcaucu gguggucgag 8700
gaacugguca agaaacggga agagugccug gacgcccugg aauccaucau gaccaccaag 8760
agcguguccu uccggcggcu gucucaccug agaaaacugg ugccuggcuu uggcaaggcc 8820
uauaccaucu ucaacaagac ccugauggaa gccgacgcuc acuacaaguc ugugcggacc 8880
uggaacgaga ucauccccag caagggcugc cugagaguug gcggaagaug ucacccucac 8940
gugaacggcg uguucuucaa cggcaucauc cugggcucug acggccacgu gcugaucccu 9000

```
gaaaugcagu cuagccugcu ccagcagcau auggaacugc uggaaagcag cgugaucccu   9060

cugaugcacc cucuggccga uccuagcacc guguucaagg auggcgacga ggucgaggac   9120

uucguggaag ugcaucugcc cgacgugcac gagcaagugu cuggcguuga acugggccug   9180

ccuaacuggg gcaaauaugu gcugaugauc gcuggggccc ugaucgcccu gaugcugauc   9240

aucuuccuga ugaccugcug ucggagagug aacagacccg agagcacaca gagcagccug   9300

ggagagacag gcagaaacgu guccgugaca agccagagcg gcaaagugau cagcagcugg   9360

gaguccuaca agagcggcgg agagacaaga cugugaccgc uacgccccaa ugacccgacc   9420

agcaaaacuc gauguacuuc cgaggaacug augugcauaa ugcaucaggc ugguauauua   9480

gauccccgcu uaccgcgggc aauauagcaa caccaaaacu cgacguauuu ccgaggaagc   9540

gcagugcaua augcugcgca guguugccaa auaaucacua uauuaaccau uuauucagcg   9600

gacgccaaaa cucaauguau uucugaggaa gcauggugca uaaugccaug cagcgucugc   9660

auaacuuuuu auuauuucuu uuauuaauca acaaaauuuu guuuuuaaca uuuc         9714
```

<210> SEQ ID NO 10
<211> LENGTH: 9660
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: SINV-AR86 RABV-G srRNA construct

<400> SEQUENCE: 10

```
gauuggcggc guaguacaca cuauugaauc aaacagccga ccaauugcac uaccaucaca     60

auggagaagc caguaguuaa cguagacgua gacccucaga guccguuugu cgugcaacug    120

caaaagagcu ucccgcaauu ugagguagua gcacagcagg ucacuccaaa ugaccaugcu    180

aaugccagag cauuuucgca ucuggccagu aaacuaaucg agcuggaggu uccuaccaca    240

gcgacgauuu uggacauagg cagcgcaccg gcucguagaa uguuuuccga gcaccaguac    300

cauugcguuu gccccaugcg uaguccagaa gacccggacc gcaugaugaa auaugccagc    360

aaacuggcgg aaaaagcaug uaagauuaca aacaagaacu ugcaugagaa gaucaaggac    420

cuccggaccg uacuugauac accggaugcu gaaacgccau cacucugcuu ccacaacgau    480

guuaccugca acacgcgugc cgaguacucc gucaugcagg acguguacau caacgcuccc    540

ggaacuauuu accaccaggc uaugaaaggc gugcggaccc uguacuggau uggcuucgac    600

accacccagu ucauguucuc ggcuauggca gguucguacc cugcauacaa caccaacugg    660

gccgacgaaa aaguccuuga agcgcguaac aucggacucu gcagcacaaa gcugagugaa    720

ggcaggacag gaaaguuguc gauaaugagg aagaaggagu ugaagcccgg gucacggguu    780

uauuucuccg uuggaucgac acuuuaccca gaacacagag ccagcuugca gagcuggcau    840

cuuccaucgg uguuccacuu gaaaggaaag cagucguaca cuugccgcug ugauacagug    900

gugagcugcg aaggcuacgu agugaagaaa aucaccauca gucccgggau cacgggagaa    960

accgugggau acgcgguuac aaacaauagc gagggcuucu ugcuaugcaa aguuaccgau   1020

acaguaaaag gagaacgggu aucguucccc gugugcacgu auaucccggc caccauaugc   1080

gaucagauga ccggcauaau ggccacggau aucucaccug acgaugcaca aaaacuucug   1140

guugggcuca accagcgaau cgucauuaac gguaagacua acaggaacac caauaccaug   1200

caaaauuacc uucugccaau cauugcacaa ggguucagca aaugggccaa ggagcgcaaa   1260
```

-continued

```
gaagaucuug acaaugaaaa aaugcugggc accagagagc gcaagcuuac auauggcugc   1320
uuguggggcgu uucgcacuaa gaaagugcac ucguucuauc gcccaccugg aacgcagacc   1380
aucguaaaag ucccagccuc uuuuagcgcu uuccccaugu cauccguaug gacuaccucu   1440
uugcccaugu cgcugaggca gaagaugaaa uuggcauuac aaccaaagaa ggaggaaaaa   1500
cugcugcaag ucccggagga auuaguuaug gaggccaagg cugcuuucga ggaugcucag   1560
gaggaaucca gagcggagaa gcuccgagaa gcacucccac cauuaguggc agacaaaggu   1620
aucgaggcag cugcggaagu ugucugcgaa guggaggggc uccaggcgga caccggagca   1680
gcacucgucg aaaccccgcg cggucaugua aggauaaauac cucaagcaaa ugaccguaug   1740
aucggacagu acaucguugu cucgccaacc ucugugcuga agaacgcuaa acucgcacca   1800
gcacacccgc uagcagacca gguuaagauc auaacgcacu ccggaagauc aggaagguau   1860
gcagucgaac cauacgacgc uaaaguacug augccagcag gaagugccgu accauggcca   1920
gaauucuuag cacugaguga gagcgccacg cuaguguaca acgaaagaga guuugugaac   1980
cgcaagcugu accauauugc caugcacggu cccgcuaaga auacagaaga ggagcaguac   2040
aagguuacaa aggcagagcu cgcagaaaca gaguacgugu uugacgugga caagaagcga   2100
ugcgucaaga aggaagaagc cucaggacuu guccucucgg gagaacugac caacccgccc   2160
uaucacgaac uagcucuuga gggacugaag acucgacccg cggucccgua caagguugaa   2220
acaauaggag ugauaggcac accaggaucg ggcaagucgg cuaucaucaa gucaacuguc   2280
acggcacgug aucuuguuac cagcggaaag aaagaaaacu gccgcgaaau ugaggccgau   2340
gugcuacggc ugaggggcau gcagaucacg ucgaagacag uggauucggu uaugcucaac   2400
ggaugccaca aagccguaga agugcuguau guugacgaag cguucgcgug ccacgcagga   2460
gcacuacuug ccuugauugc aaucgucaga ccccguaaga agguagugcu augcggagac   2520
ccuaagcaau gcggauucuu caacaugaug caacuaaagg uauauuucaa ccacccggaa   2580
aaagacauau guaccaagac auucuacaag uuuaucuccc gacguugcac acagccaguc   2640
acggcuauug uaucgacacu gcauuacgau ggaaaaaauga aaaccacaaa cccgugcaag   2700
aagaacaucg aaaucgacau uacaggggcc acgaagccga agccagggga caucauccug   2760
acaugcuucc gcgggugggu uaagcaacug caaaucgacu aucccggaca ugagguaaug   2820
acagccgcgg ccucacaagg gcuaaccaga aaaggaguau augccguccg gcaaaaaguc   2880
aaugaaaacc cgcuguacgc gaucacauca gagcauguga acgugcugcu cacccgcacu   2940
gaggacaggc uaguauggaa aacuuuacag ggcgacccau ggauuaagca gcucacuaac   3000
guaccaaaag gaaauuuuca agccaccauc gaggacuggg aagcugaaca caagggaaua   3060
auugcugcga uaaacagucc cgcuccccgu accaauccgu ucagcugcaa gacuaacguu   3120
ugcugggcga aagcacugga accgauacug gccacggccg guaucguacu uaccgguugc   3180
caguggagcg agcuguuccc acaguuugca gaugacaaac cacacucggc caucuacgcc   3240
cuggacguaa ucugcauuaa guuuuucggc auggacuuga caagcggacu guuuuccaaa   3300
cagagcaucc cguuaacgua ccauccugcc gauucagcga ggccaguagc ucauugggac   3360
aacagcccag gaacccgcaa guaugguac gaucacgccg uugccgccga acucuccccgu   3420
agauuuccgg uguuccagcu agcugggaaa ggcacacagc uugauuugca gacgggcaga   3480
acuagaguua ucuccgcaca gcauaacuug gucccaguga accgcaaucu cccgcacgcc   3540
uuaguccccg agcacaagga gaaacaaccc ggcccgguca aaaaauucuu gagccaguuc   3600
aaacaccacu ccguacuugu ggucucagag gaaaaaaaug aagcucccca caagagaauc   3660
```

```
gaauggaucg ccccgauugg cauagccggc gcugauaaga acuacaaccu ggcuuucggg   3720
uuuccgccgc aggcacggua cgaccuggug uuuaucaaua uuggaacuaa auacagaaac   3780
caucacuuuc agcagugcga agaccaugcg gcgaccuuga aaacccucuc gcguucggcc   3840
cugaacugcc uuaaccccgg aggcacccuc guggugaagu ccuacgguua cgccgaccgc   3900
aauagugagg acguagucac cgcucuugcc agaaaauuug ucagaguguc ugcagcgagg   3960
ccagagugcg ucucaagcaa uacagaaaug uaccugaucu uccgacaacu agacaacagc   4020
cgcacacgac aauucacccc gcaucaucug aauuguguga uuucguccgu guacgagggu   4080
acaagagacg gaguuggagc cgcaccgucg uaccguacua aaagggagaa cauugcugau   4140
ugucaagagg aagcaguugu caaugcagcc aauccacugg gcagaccagg agaaggaguc   4200
ugccgugcca ucuauaaacg uuggccgaac aguuucaccg auucagccac agagacaggu   4260
accgcaaaac ugacugugug ccaaggaaag aaagugaucc acgcgguugg cccugauuuc   4320
cggaaacacc cagaggcaga agcccugaaa uugcugcaaa acgccuacca ugcaguggca   4380
gacuuaguaa augaacauaa uaucaagucu gucgccaucc cacugcuauc uacaggcauu   4440
uacgcagccg gaaaagaccg ccuugaggua ucacuuaacu gcuugacaac cgcgcuagac   4500
agaacugaug cggacguaac caucuacugc cuggauaaga aguggaagga aagaaucgac   4560
gcggugcucc aacuuaagga gucuguaacu gagcugaagg augaggauau ggagaucgac   4620
gacgaguuag uauggaucca uccggacagu ugccugaagg gaagaaaggg auucaguacu   4680
acaaaaggaa aguuguauuc guacuuugaa ggcaccaaau uccaucaagc agcaaaagau   4740
auggcggaga uaaagguccu guucccaaau gaccaggaaa gcaacgaaca acugugugcc   4800
uacauauugg gggagaccau ggaagcaauc cgcgaaaaau gcccggucga ccacaacccg   4860
ucgucuagcc cgccaaaaac gcugccgugc cucuguaugu augccaugac gccagaaagg   4920
guccacagac ucagaagcaa uaacgucaaa gaaguuacag uaugcuccuc cacccccccuu   4980
ccaaaguaca aaaucaagaa uguucagaag guucagugca caaaaguagu ccuguuuaac   5040
ccgcauaccc ccgcauucgu ucccgcccgu aaguacauag aagcaccaga acagccugca   5100
gcuccgccug cacaggccga ggaggccccc ggaguuguag cgacaccaac accaccugca   5160
gcugauaaca ccucgcuuga ugucacggac aucucacugg acauggaaga caguagcgaa   5220
ggcucacucu uuucgagcuu uagcggaucg gacaacuacc gaaggcaggu gguggguggcu   5280
gacguccaug ccguccaaga gccugccccu guuccaccgc caaggcuaaa gaagauggcc   5340
cgccuggcag cggcaagaau gcaggaggag ccaacuccac cggcaagcac cagcucugcg   5400
gacgaguccc uucaccuuuc uuuugauggg guaucuauau ccuucggauc ccuuuucgac   5460
ggagagaugg cccgcuuggc agcggcacaa cccccggcaa guacaugccc uacggaugug   5520
ccuaugucuu ucggaucguu uuccgacgga gagauugagg aguugagccg cagaguaacc   5580
gagucggagc ccguccuguu ugggucauuu gaaccgggcg aagugaacuc aauuauaucg   5640
ucccgaucag ccguaucuuu uccaccacgc aagcagagac guagacgcag gagcaggagg   5700
accgaauacu gucuaaccgg gguagguggg uacauauuuu cgacggacac aggcccuggg   5760
cacuugcaaa agaaguccgu ucugcagaac cagcuuacag aaccgaccuu ggagcgcaau   5820
guucuggaaa gaaucuacgc cccggugcuc gacacgucga aagaggaaca gcucaaacuc   5880
agguaccaga ugaugcccac cgaagccaac aaaagcaggu accagucucg aaaaguagaa   5940
aaccagaaag ccauaaccac ugagcgacug cuuucagggc uacgacugua uaacucugcc   6000
```

-continued

```
acagaucagc cagaaugcua uaagaucacc uacccgaaac caucguauuc cagcagugua   6060
ccagcgaacu acucugaccc aaaguuugcu guagcuguuu guaacaacua ucugcaugag   6120
aauuacccga cgguagcauc uuaucagauc accgacgagu acgaugcuua cuuggauaug   6180
guagacggga cagucgcuug ccuagauacu gcaacuuuuu gccccgccaa gcuuagaagu   6240
uacccgaaaa gacacgagua uagagcccca aacauccgca gugcgguucc aucagcgaug   6300
cagaacacgu ugcaaaacgu gcucauugcc gcgacuaaaa gaaacugcaa cgucacacaa   6360
augcgugaac ugccaacacu ggacucagcg acauucaacg uugaaugcuu ucgaaaauau   6420
gcaugcaaug acgaguauug ggaggaguuu gcccgaaagc caauuaggau cacuacugag   6480
uucguuaccg cauacguggc cagacugaaa ggcccuaagg ccgccgcacu guucgcaaag   6540
acgcauaauu uggucccauu gcaagaagug ccuauggaua gauucgucau ggacaugaaa   6600
agagacguga aaguuacacc uggcacgaaa cacacagaag aaagaccgaa aguacaagug   6660
auacaagccg cagaaccccu ggcgaccgcu uaccuaugcg ggauccaccg ggaguuagug   6720
cgcaggcuua cagccguuuu gcuacccaac auucacacgc ucuuugacau gucggcggag   6780
gacuuugaug caaucauagc agaacacuuc aagcaaggug acccgguacu ggagacggau   6840
aucgccucgu ucgacaaaag ccaagacgac gcuauggcgu uaaccggccu gaugaucuug   6900
gaagaccugg guguggacca accacuacuc gacuugaucg agugcgccuu uggagaaaua   6960
ucauccaccc aucugcccac ggguacccgu uucaaauucg gggcgaugau gaaauccgga   7020
auguuccuca cgcucuuugu caacacaguu cugaaugucg uuaucgccag cagaguauug   7080
gaggagcggc uuaaaacguc caaaugugca gcauuuaucg gcgacgacaa cauuauacac   7140
ggaguaguau cugacaaaga aauggcugag aggugugcca ccuggcucaa cauggagguu   7200
aagaucauug acgcagucau cggcgagaga ccaccuuacu ucugcggugg auucaucuug   7260
caagauucgg uuaccuccac agcgugucgc guggcggacc ccuugaaaag gcuguuuaag   7320
uuggguaaac cgcucccagc cgacgaugag caagacgaag acagaagacg cgcucugcua   7380
gaugaaacaa aggcgugguu uagaguaggu auaacagaca ccuuagcagu ggccguggca   7440
acucgguaug agguagacaa caucacaccu guccugcugg cauugagaac uuuugcccag   7500
agcaaaagag cauuucaagc caucagaggg gaaauaaagc aucucuacgg ugguccuaaa   7560
uagucagcau aguacauuuc aucugacuaa uaccacaaca ccaccaccau gaauagagga   7620
uucuuuaaca ugcucggccg ccgccccuuc ccagcccccca cugccaugug gaggccgcgg   7680
agaaggaggc aggcggcccc gggaagcgga gcuacuaacu ucagccugcu gaagcaggcu   7740
ggagacgugg aggagaaccc uggaccuaug gugccucagg ugcugcuguu ugugccucug   7800
cugggcuuca gccugugcuu cggcaaguuc cccaucuaca caauccccga caagcucggc   7860
ccuuggagcc ccaucgauau ccaccaccug agcugcccca acaaccuggu gguggaagau   7920
gagggcugca ccaaccugag cgaguucagc uacauggaac ugaaaguggg cuacaucagc   7980
gccaucaaag ugaacggcuu caccuguacc ggcgugguca cagaggccga gacauacacc   8040
aacuucgugg gcuacgugac caccaccuuc aagcggaagc acuucagacc cacaccugac   8100
gccuguagag ccgccuacaa cuggaaaaug gccggcgauc ccagauacga ggaaagccug   8160
cacaaccccu auccugacua ccacuggcug cggaccguga aaccaccaa agagagccug   8220
gucaucauca gccccagcgu gaccgaccug gauccuuacg auaagagccu gcacucccgg   8280
guguucccug gcggaaauug cucuggcauc accgugucca gcaccuacug cagcaccaac   8340
cacgacuaca ccaucuggau gcccgagaac cugagacugg gcaccagcug cgacaucuuc   8400
```

accaacagca gaggaaagcg ggccagcaaa ggcggcaaga ccuguggcuu uguggacgag 8460
agaggccugu acaagucucu gaagggcgcc ugcaagcuga agcugugcgg aguucuggga 8520
cugagacuga uggauggcac cugggucgcc augcagacca gcgacgagac aaaguggugu 8580
ccuccuggcc agcuggucaa ccugcacgac uuuagauccg acgagaucga gcaucuggug 8640
gucgaggaac uggucaagaa acgggaagag ugccuggacg cccuggaauc caucaugacc 8700
accaagagcg uguccuuccg gcggcugucu caccugagaa aacuggugcc uggcuuuggc 8760
aaggccuaua ccaucuucaa caagacccug auggaagccg acgcucacua caagucugug 8820
cggaccugga acgagaucau ccccagcaag ggcugccuga gaguuggcgg aagaugucac 8880
ccucacguga acggcguguu cuucaacggc aucauccugg gcucugacgg ccacgugcug 8940
aucccugaaa ugcagucuag ccugcuccag cagcauaugg aacugcugga aagcagcgug 9000
aucccucuga ugcacccucu ggccgauccu agcaccgugu ucaaggaugg cgacgagguc 9060
gaggacuucg uggaagugca ucugcccgac gugcacgagc aagugucugg cguugaacug 9120
ggccugccua acuggggcaa auaugugcug augaucgcug gggcccugau cgcccugaug 9180
cugaucaucu uccugaugac cugcugucgg agagugaaca gacccgagag cacacagagc 9240
agccugggag agacaggcag aaacgugucc gugacaagcc agagcggcaa agugaucagc 9300
agcugggagu ccuacaagag cggcggagag acaagacugu gaccgcuacg ccccaaugac 9360
ccgaccagca aaacucgaug uacuuccgag gaacugaugu gcauaaugca ucaggcuggu 9420
auauuagauc cccgcuuacc gcgggcaaua uagcaacacc aaaacucgac guauuuccga 9480
ggaagcgcag ugcauaaugc ugcgcagugu ugccaaauaa ucacuauauu aaccauuuau 9540
ucagcggacg ccaaaacuca auguauuucu gaggaagcau ggugcauaau gccaugcagc 9600
gucugcauaa cuuuuuauua uuucuuuuau uaaucaacaa aauuuuguuu uuaacauuuc 9660

<210> SEQ ID NO 11
<211> LENGTH: 9588
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: EEEV RABV-G srRNA construct

<400> SEQUENCE: 11
gauaggguac gguguagagg caaccacccu auuuccaccu auccaaaaug gagaaaguuc 60
auguugacuu agacgcagac agcccauucg ucaagucacu gcaaagaugc uuuccacauu 120
uugagauaga agcaacgcag gucacugaca augaccaugc uaaugcuagg gcguuuucgc 180
accuagcuac uaagcucauu gagggagaag uggauacaga ccaggugauc cuggauauug 240
ggagcgcgcc uguaaggcac acgcauucca aacauaagua ccacugcauu ugcccaauga 300
aaagcgcaga agacccugac agacucuacc gcuaugcaga caagcuuaga aaaagugaug 360
ucacugacaa auguauugcc ucuaaggccg cggaccugcu aacaguaaug ucgacgccug 420
acacugagac acccucguua ugcaugcaca cugacucaac uugccgguac cacggcuccg 480
uggccguaua ucaggaugua uaugcagugc augcaccgac uuccauuuac uaccaggcgc 540
ugaaaggugu acgaacuauc uauuggaucg gguuugauac uacaccguuc auguacaaga 600
acauggcagg cgccuacccu acauacaaca caaauugggc cgaugaaagu guguuggaag 660
ccagaaauau agggcugggu aguucagacu ugcacgaaaa gaguuucgga aaaguaucca 720

-continued

```
uuaugaggaa gaagaaauua caacccacua auaaaguaau auuuucugug gggucaacua    780
uuuauacuga agagagaaua cuguuacgca guuggcaucu accuaauguc uuucaucuaa    840
aagguaaaac uagcuuuaca ggcagaugua acaccaucgu cagcugcgaa gguuacguug    900
ucaagaagau uacgcucagu ccugggauuu acgggaaagu ggauaaucuu gcuucgacca    960
ugcaccgaga gggauucuua aguugcaagg uuacagacac guuaagaggg gagagggucu   1020
cuuuccccgu auguacguac gugccagcga cacugugcga ccagaugacc gggauacugg   1080
cgacugacgu cagugucgau gacgcccaga agcugcuggu ugggcucaac cagcgaauug   1140
ucgucaaugg cagaacacaa cguaacacaa auaccaugca gaauuaucua uuaccagugg   1200
ucgcccaggc guucucgcgg ugggcgcggg aacaccgcgc agaccuggag gacgaaaaag   1260
ggcuaggggu acgggaacgu ucccuaguca ugggcugcug cugggcuuuc aaaacucaca   1320
agaucacauc cauuuacaag agaccuggga cucaaacuau caagaaggug cccgccguau   1380
ucaauuccuu cgucauccca caaccaacca gcuaugggcu ugauauagga uugcgucgcc   1440
gaauuaagau gcuauucgac gcaaagaagg cacccgcucc aauuauuacu gaggccgacg   1500
ucgcacaccu uaaaggccug caggaugaag cugaagccgu ggcugaggcu gaagccgugc   1560
gugcagcacu accuccacuu cugccggagg ucgauaagga gaccguagag gccgauaucg   1620
accugaucau gcaggaggca ggagcaggca gcguggagac accuagacga cacaucaagg   1680
ucacgacgua uccaggagaa gaaaugaucg gcucguacgc agugcucuca ccacaagcgg   1740
uccuuaacag cgagaagcua gcuugcauuc acccguuagc ugagcaagug cucgugauga   1800
cucacaaagg gcgcgcagga cgauacaagg uagagccaua ccacgguaga guuaucgucc   1860
cuagugguac agcuauacca auccccgauu uccaggcucu gagugaaagu gcaaccauag   1920
uauuuaacga acgggaguuc guuaaccguu acuuacacca cauugccguu aacggagggg   1980
cauugaauac agaugaagag uacuacaagg uugugaaaag cacugagaca gacucugagu   2040
acguauuuga caucgacgca aagaagugcg ugaagaaagg ggaugccgga ccaaugugcc   2100
uggucggcga guuaguagac ccgccauucc acgaauuugc guacgagagu uuaaaaacac   2160
guccugcugc accacacaaa gugccuacua ucggagucua uggaguccca gguuccggaa   2220
agucugguau aaucaaaagc gcuguuacca agcgugaucu gguggucagu gcaaagaaag   2280
aaaauugcau ggaaaucauu aaagacguca aacguaugcg cggcauggac aucgccgccc   2340
gcacagugga uucggugcug cuaaaugggg uaaaacacuc cgucgacaca cuguacauag   2400
acgaggcauu cgcuugccau gcagggaccc ugcuagcacu uaucgccauc gucaagccaa   2460
agaaaguugu auugugugga gauccgaaac aaugcggcuu cuuuaacaug augugucuaa   2520
aaguacauuu uaaccacgag auaugcacag aaguguauca caagaguauu ucucggcgau   2580
gcacuaagac agugacaucc auuguuucua cccuguucua ugauaaacgg augagaacug   2640
ucaacccaug caaugauaag aucauaauag auaccaccag uacuaccaaa ccuuuaaagg   2700
augacauaau auuaaccugc uuuagagggu ggguuaagca acugcagauu gacuacaaga   2760
accacgagau caugaccgca gcggccucac aggggcuuac uagaaaaggg guauacgcag   2820
ugcgcuacaa ggucaaugag aacccacuau acgcacagac aucugagcau gugaauguau   2880
uacuuacacg cacagaaaaa cguauaguau ggaagacuuu ggccggugac ccuuggauca   2940
agacguugac agcaucguau ccggguaauu ucaccgccac acuggaagaa uggcaagcug   3000
agcaugacgc uaucauggcg aaaauacuug agacaccagc uagcagcgac guuuuccaaa   3060
```

-continued auaaagugaa caucugcugg gccaaagcgc uagaaccugu guuggccacc gccaauauua 3120
cgcugacccg cucgcagugg gagacuauuc cagcguucaa ggaugacaaa gcguauucgc 3180
cugagauggc cuuaaacuuu uucugcacca gauucuuugg ugucgacauc gacagcgggu 3240
uguucuccgc gccaacuguu ccgcugacuu acaccaauga acacugggau aauagcccag 3300
guccaaacau guauggguug ugcaugcgca cugcuaaaga acuugcacgu cgguauccuu 3360
guauucugaa agccguggau acagguagag uggcugacgu ucgcacagac acuaucaaag 3420
acuauaaccc gcuaauaaau gugguacccc uuaauagaag acucccacac ucguugguug 3480
ucacacacag auacacuggg aacggugauu acucccagcu agugacuaag augaccggaa 3540
aaaccguacu cguagugggu acaccuauga acauaccagg aaagagaguu gagacauuag 3600
gcccaagccc acaauguaca uauaaagcgg aauuggaccu gggcauuccu gccgcuuuag 3660
gcaaauauga caucaucuuu auuaacguga ggacucccua ccgacaccac cacuaccaac 3720
agugcgagga ccaugcgauc caccacagca ugcuuaccag aaaagcagug gaccauuuga 3780
acaaaggcgg uacgugcauc gcauugggcu augggacugc ggacagagcc accgagaaca 3840
uuaucucugc agucgcccgc ucauucaggu ucucacgugu gugccagccg aagugugccu 3900
gggaaaacac ugaggucgcg uucguguuuu ucggcaagga caacggcaac caucuccaag 3960
aucaagauag gcugaguguu guguuaaaca acauauacca agggucaacu caacaugaag 4020
cuggcagagc accugcguau agaguggugc gcggcgacau aacaaagagc aaugaugagg 4080
uuauuguuaa cgcggcgaac aacaaagggc aaccuggugg cggugugugu ggcgcccuuu 4140
acaggaagug gccuggagcu uuugacaagc agccgguagc aacugguaaa gcgcaccucg 4200
ucaagcauuc uccgaacguc auccaugccg uuggcccuaa uuuuucuagg cuaucagaaa 4260
acgaaggaga ccagaaauug ucugaagugu acauggacau ugccagaauu aucaacaacg 4320
agagguuuac uaaagucucc auuccguugu uaucuaccgg cauuuacgca gguggduaagg 4380 acaggguuau gcaaucgcug aaccauuuau ucacagccau ggauacuacc gacgcagaca 4440
ucaccauuua cugucuagau aagcaauggg agucaagaau aaaggaagcu aucacccgga 4500
aggaaagugu ugaagaacuu acugaggaug acagaccagu ugacauugaa cugguacggg 4560
ugcacccguu gagcagcuug gcagguagac cugguuauuc aaccaccgag ggcaaggugu 4620
auucguaccu agaggggacu agguuucacc aaacugccaa agacauagcu gaaauuuacg 4680
cuauguggcc uaacaagcaa gaagcaaacg agcagauuug cuuauaugug uugggagaga 4740
guaugaacag cauccgcucu aaguguccag uugaagaguc ggaggccucu ucccccccuc 4800
acaccauccc gugucugugc aacuaugcaa ugacugcaga gcgaguuuac agauuacgua 4860
uggcgaagaa ugaacaauuc gcaguuuguu cguccuuuca guuaccgaaa uacaggauua 4920 caggggguuca gaaaauucaa ugcaguaaac cugugauauu cuccggcacu guaccaccgg 4980
ccauacaucc aagaaaauuc gcaucuguga caguggaaga cacuccggug guccaaccug 5040
aaagguuggu gccuaggcga ccugcaccgc cugugcccgu accugcaaga auccccagcc 5100
cuccauguac aucgaccaac ggaucgacga ccaguauaca aucacugggg gaggaucaaa 5160
gcgcaucugc uucuagcgga gcugaaaucu cuguagacca gguuucgcua uggagcauac 5220
ccagcgcuac uggguucgau gugcguaccu ccucaucguu gagucuagag cagucuaccu 5280
uuccgacaau gguugucgaa gcagagauuc acgccaguca aggaucacug uggaguauac 5340
ccaguaucac cggaucugaa acccgcguuc cgucaccucc aagucagggu agcagacauu 5400
ccaccccauc uguaagugcu ucacacacgu ccguggacuu aaucacguuu gacagcguug 5460

```
cagagauuuu ggaagauuuc agucguucgc cguuucaauu uuugucugaa aucaaaccua   5520
ucccugcacc ucguacccga guuaauaaca ugagccgcag cgcagacacg aucaaaccaa   5580
uuccaaagcc gcguaaaugc caggugaagu acacgcagcc accuggcguc gccagggcca   5640
uaucggcagc ggaauuugac gaguuugugc ggaggcacuc gaauugacgg uacgaagcgg   5700
gcgcguacau uuucucaucc gagacaggac aagggcaccu gcaacaaaaa uccacgcggc   5760
aaugcaaacu ccaguaucca auccuggagc guuccgucca ugagaaauuu uacgccccgc   5820
gccucgaucu cgagcgugag aagcuguugc agaagaaacu acaauugugu gcuucugaag   5880
guaaucggag cagguaucag ucucguaaag uagagaacau gaaggcaauc accguugagc   5940
gucuacugca ggggauaggc ucauaucucu cugcagaacc gcaaccaguu gaaugcuaca   6000
aagucaccua uccugcuccc auguauucaa guacugcaag caacagcuuu ucaucagcag   6060
aaguggccgu caaagucugc aaccuaguac ugcaagagaa uuuucccacc guagccagcu   6120
auaacauaac ggaugaguau gaugccuauc uugacauggu ggacggagca uccugcuguu   6180
uagauacugc cacuuuuugc ccagcuaaau ugaggagcuu uccaaagaag cacaguuauu   6240
ugcggccuga gauacgauca gcagugccau caccgauuca aaacacgcuc cagaauguac   6300
uagcagcagc cacgaaacgg aauugcaaug ucacucaaau gagggaacuu ccaguguugg   6360
auucagcugc cuucaacgug gaguguuuca aaaaguacgc cuguaacgau gaguacuggg   6420
acuucuacaa gacaaacccg auaagacuca ccgcagaaaa uguuacucag uauguuacua   6480
aguuaaaggg acccaaagca gcugcccuuu uugcgaaaac gcauaacuua cagccauugc   6540
augagauacc aauggauaga uucgugaugg accuuaaacg ggaugucaag gucacacccg   6600
ggacaaaaca uacugaagaa agaccaaaag uucaggugau acaggcagcu gauccacuug   6660
caaccgccua ccuauguggu auacaucgag agcuugugcg cagguugaac gcagugcugc   6720
uaccgaauau ccacacuuug uuugacaugu cugcagaaga uuuugaugcu aucauugccg   6780
aacacuuuca auucggcgac gcgguguuag agacagacau agcuucuuuu gauaaaagcg   6840
aggacgaugc uaucgccaug uccgcucuaa ugauucuuga agaccuagga guugaucagg   6900
cacuguuaaa ccuaauugag gcagccuuug ggaacauaac aucugugcac uuaccaacag   6960
gcacccgauu uaaguucggg gcaaugauga aaucugggau guuuuugaca cucuuuauca   7020
auaccguugu caauaucaug aucgcuagcc gcgugcuccg cgagcggcug accacuuccc   7080
ccugcgcagc auuuaucggc gacgacaaca ucgugaaagg gguuacaucu gacgcgcuga   7140
uggcagagcg gugcgccacg ugguugaaca uggaagugaa gaucaucgau gcaguagucg   7200
gaguaaaggc accguacuuu ugcggagggu ucaucguagu cgaucagauu acaggaacug   7260
cgugcagagu cgccgacccc cugaagagac uguuuaagcu agguaagccg cuuccacugg   7320
acgaugacca agacgucgac aggcgcagag cucugcauga ugaagcggca cguuggaaca   7380
gaauuggcau caccgaagaa cuggugaaag caguugaauc acgcuacgag gugaacuacg   7440
ugucacuaau caucacagcg uugaccacau uagcaucuuc aguuagcaac uuuaaacaca   7500
uaagagguca ccccauaacc cucuacggcu gaccuaaaua gguugugcau uaguaccuaa   7560
ccuauuuaua uuauauugcu aucuaaauau cagagcugga gacguggagg agaacccugg   7620
accuauggug ccucaggugc ugcuguuugu gccucugcug ggcuucagcc ugugcuucgg   7680
caaguucccc aucuacacaa uccccgacaa gcucggcccu uggagcccca ucgauaucca   7740
ccaccugagc ugccccaaca accugguggu ggaagaugag ggcugcacca accugagcga   7800
```

-continued

```
guucagcuac auggaacuga aagugggcua caucagcgcc aucaaaguga acggcuucac   7860
cuguaccggc gugguCacag aggccgagac auacaccaac uucgugggcu acgugaccac   7920
caccuucaag cggaagcacu ucagacccac accugacgcc uguagagccg ccuacaacug   7980
gaaaauggcc ggcgauccca gauacgagga aagccugcac aaccccuauc cugacuacca   8040
cuggcugcgg accgugaaaa ccaccaaaga gagccugguc aucaucagcc ccagcgugac   8100
cgaccuggau ccuuacgaua agagccugca cucccgggug uucccuggcg gaaauugcuc   8160
uggcaucacc guguccagca ccuacugcag caccaaccac gacuacacca ucuggaugcc   8220
cgagaaccug agacugggca ccagcugcga caucuucacc aacagcagag gaaagcgggc   8280
cagcaaaggc ggcaagaccu guggcuuugu ggacgagaga ggccuguaca agucucugaa   8340
gggcgccugc aagcugaagc ugugcggagu ucugggacug agacugaugg auggcaccug   8400
ggucgccaug cagaccagcg acgagacaaa guggcguccu ccuggccagc uggucaaccu   8460
gcacgacuuu agauccgacg agaucgagca ucugguggucd gaggaacugg ucaagaaacg   8520
ggaagagugc cuggacgccc uggaauccau caugaccacc aagagcgugu ccuuccggcg   8580
gcugucucac cugagaaaac uggugccugg cuuuggcaag gccuauacca ucuucaacaa   8640
gacccugaug gaagccgacg cucacuacaa gucugugcgg accuggaacg agaucauccc   8700
cagcaagggc ugccugagag uuggcggaag augucacccu cacgugaacg gcguguucuu   8760
caacggcauc auccugggcu cugacggcca cgugcugauc ccugaaaugc agucuagccu   8820
gcuccagcag cauauggaac ugcuggaaag cagcgugauc ccucugaugc acccucuggc   8880
cgauccuagc accguguuca aggauggcga cgaggucgag gacuucgugg aagugcaucu   8940
gcccgacgug cacgagcaag ugucuggcgu ugaacugggc cugccuaacu ggggcaaaua   9000
ugugcugaug aucgcugggg cccugaucgc ccugaugcug aucaucuucc ugaugaccug   9060
cugucggaga gugaacagac ccgagagcac acagagcagc cugggagaga caggcagaaa   9120
cguguccgug acaagccaga gcggcaaagu gaucagcagc ugggaguccu acaagagcgg   9180
cggagagaca agacugugac cgcuacgccc caaugacccg accagcuaac aucuugucaa   9240
ccacauaaca cuacaggcag uguauaaggc ugucuuacua aacacuaaau ucacccuagu   9300
ucgauguacu uccgagcuau ggugacggug gugcauaaug ccgccgaugc agugcauaag   9360
gcugcuauau uaccaaauua uaacacuaag ggcagugcau aaugcugcuc cuaaguaauu   9420
uuauacacac uuuauaauca ggcauaauug ccguauauac aauuacacua cagguaauau   9480
accgccucuu auaaacacua caggcagcgc auaaugcugu cuuuuauauc aauuuacaaa   9540
aucauauuaa uuuuuucuuu uauguuuuua uuuuguuuuu aauauuuc                 9588
```